(12) United States Patent
Tasaka et al.

(10) Patent No.: US 6,573,289 B1
(45) Date of Patent: Jun. 3, 2003

(54) NAPHTHALENE DERIVATIVES, THEIR PRODUCTION AND USE

(75) Inventors: Akihiro Tasaka, Suita (JP); Akio Ojida, Nishinomiya (JP); Tomohiro Kaku, Nishinomiya (JP); Masami Kusaka, Kobe (JP); Masuo Yamaoka, Kobe (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/673,591

(22) PCT Filed: Apr. 22, 1999

(86) PCT No.: PCT/JP99/02143

§ 371 (c)(1),
(2), (4) Date: Oct. 18, 2000

(87) PCT Pub. No.: WO99/54309

PCT Pub. Date: Oct. 28, 1999

(30) Foreign Application Priority Data

Apr. 23, 1998 (JP) ............................ 10-113801

(51) Int. Cl.$^7$ ................... A61K 31/415; C07D 233/64; A61P 43/00
(52) U.S. Cl. ................. 514/399; 548/333.5; 548/341.5
(58) Field of Search .............. 548/333.5, 341.5; 514/399

(56) References Cited

U.S. PATENT DOCUMENTS

| | | |
|---|---|---|
| 3,759,934 A | 9/1973 | Houlihan |
| 4,734,406 A | 3/1988 | Lau et al. |

FOREIGN PATENT DOCUMENTS

| | | | |
|---|---|---|---|
| EP | 098690 A | | 1/1984 |
| EP | 273647 A | | 7/1988 |
| EP | 721943 A | | 7/1996 |
| EP | 778276 A | | 6/1997 |
| EP | 820989 A | | 1/1998 |
| FR | 2617478 | * | 1/1989 |
| NL | 6609596 | * | 1/1967 |
| WO | WO 92/16527 | | 10/1992 |
| WO | WO 95/01967 A | | 1/1995 |
| WO | WO 95/01968 A | | 1/1995 |
| WO | 200078727 | * | 12/2000 |
| WO | 2001030763 | * | 5/2001 |

OTHER PUBLICATIONS

Adam, et al, J. Org. Chem, 1997, 6(2), 7841–7843.*
Regel, et al, Justus Liebigs Ann., 1977, (1), 145–158.*
Asingner, et al, Montash Chem., 1975, 106(6), 1461–8.*
Murray, et al, J. Het. Chem., 1990, 27(2), 1933–40.*
Silverman, Richard, 1993, The organic Chemistry of Drug Design and Drug Action, 352–354.*
Arnoldi et al. "Synthesis, Fungicidal Activity and Structure–Activity Relationships . . . " Pest Sci. vol. 14, p. 576–86 (1983).
C. M. Shafer et al. "Monosubstituted Oxazoles. 1. Synthesis of 5–Substituted Oxazoles by Directed Alkylation" J. Org. Chem. vol. 63, No. 3, pp. 551–555 (1998).

* cited by examiner

Primary Examiner—Joseph K. McKane
Assistant Examiner—Andrea D. Small
(74) Attorney, Agent, or Firm—Mark Chao; Elaine M. Ramesh

(57) ABSTRACT

A composition containing a compound of the formula:

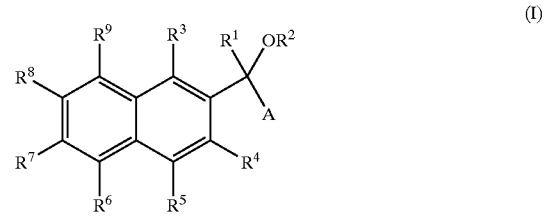

(I)

wherein A is a nitrogen-containing heterocyclic group which may be substituted, $R^1$ is a hydrogen atom, hydrocarbon group which may be substituted, or monocyclic aromatic heterocyclic group which may be substituted, $R^2$ is a hydrogen atom or a lower alkyl group which may be substituted, $R^3$, $R^4$, $R^5$, $R^6$, $R^7$, $R^8$ and $R^9$ are independently a hydrogen atom, a hydrocarbon group which may be substituted, a hydroxy group which may be substituted, a thiol group which may be substituted, an amino group which may be substituted, an acyl group or a halogen atom, a salt thereof or a prodrug thereof has steroid $C_{17,20}$-lyase inhibitory activity, and is useful for preventing and treating for example, primary cancer of malignant tumor, its metastasis and recurrence thereof.

35 Claims, No Drawings

NAPHTHALENE DERIVATIVES, THEIR PRODUCTION AND USE

This application is a 371 of PCT/JP99/02143, filed on Apr. 22, 1999.

TECHNICAL FIELD

The present invention relates to a medicine, especially to novel naphthalene derivatives having steroid $C_{17,20}$-lyase inhibitory activity, or its production and pharmaceutical compositions containing the same.

BACKGROUND ART

It is known that, in the biosynthesis of androgen in vivo, steroid $C_{17,20}$-lyase acts at the final stage. That is, steroid $C_{17,20}$-lyase converts 17-hydroxypregnenolone and 17-hydroxyprogesterone derived from cholesterol to dehydroepiandrosterone and androstenedione, respectively. Therefore, a medicine having steroid $C_{17,20}$-lyase inhibitory activity suppress the formation of androgen and estrogen which is produced from androgen, and is useful for preventing and treating diseases whose exacerbation factor is androgen or estrogen. As the disease whose exacerbation factor is androgen or estrogen, there may be mentioned, for example, prostate cancer, prostatic hypertrophy, virilism, irsutism, male pattern alopecia, precocious puberty, breast cancer, uterine cancer, mastopathy, uterus myoma, endometriosis, adenomyosis of uterus, polycystic ovary syndrome, etc.

It has been already known that some steroid type compounds and some non-steroid type compounds inhibit steroid $C_{17,20}$-lyase. The steroid type compounds are disclosed in, for example, WO 92/15404, WO 93/20097, EP-A 288053, EP-A 413270, etc. As non-steroid type compounds, for example, (1H-imidazol-1-yl)methyl-substituted benzimidazole derivatives are shown in Japanese Published Unexamined Patent Application No.85975/1989, carbazole derivatives are shown in WO94/27989 and WO96/14090, azole derivatives are shown in WO95/09157, and 1H-benzimidazole derivatives are shown in U.S. Pat. No. 5,491,161.

Heretofore, steroid $C_{17,20}$-lyase inhibitors which can actually be used as medicine have not been known. Thus, the early development of steroid $C_{17,20}$-lyase inhibitors which are useful as medicine has been expected.

DISCLOSURE OF INVENTION

The present inventors have done extensive studies so as to find superior steroid $C_{17,20}$-lyase inhibitors, and found that a compound having the formula (I) which has a naphthalene ring structure having nitrogen-containing heterocyclic groups through substituted methylene chain at 2-position unexpectedly has superior steroid $C_{17,20}$-lyase inhibiting activity because of its specific structure and that the compound has less toxicity and has good properties as a medicine. The present invention has been accomplished by these findings.

Thus the present invention relates to
(1) A compound of the formula:

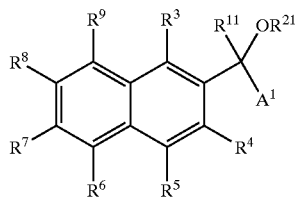

(I')

wherein $A^1$ is an imidazolyl group, a thiazolyl group, an oxazolyl group or a pyridyl group, each of which may be substituted; $R^{11}$ is a hydrogen atom, a hydrocarbon group which may be substituted; or a monocyclic aromatic heterocyclic group which may be substituted; $R^{21}$ is a hydrogen atom or a lower alkyl group which may be substituted; $R^3$, $R^4$, $R^5$, $R^6$, $R^7$, $R^8$ and $R^9$ are independently a hydrogen atom, a hydrocarbon group which may be substituted, a hydroxy group which may be substituted, a thiol group which may be substituted, an amino group which may be substituted, an acyl group or a halogen atom, provided (1) that $R^{11}$ is a saturated hydrocarbon group which may be substituted when $A^1$ is an oxazolyl group which may be substituted or a thiazolyl group which may be substituted, (2) that $R^7$ is a hydroxy group which may be substituted or a lower alkyl group when $A^1$ is a pyridyl group and $R^{11}$ or $R^{21}$ is a hydrogen atom and (3) that $R^{21}$ is a lower alkyl group which may be substituted when $R^{11}$ is a hydrogen atom, a salt thereof;

(2) A compound as shown in the above item (1), wherein $R^3$, $R^4$, $R^5$, $R^6$, $R^7$, $R^8$ and $R^9$ are independently a hydrogen atom, a hydrocarbon group which may be substituted, a hydroxy group which may be substituted, an amino group which may be substituted, an acyl group or a halogen atom;

(3) A compound as shown in the above item (1), wherein $R^3$, $R^4$, $R^5$, $R^6$, $R^7$, $R^8$ and $R^9$ are independently a hydrogen atom, a hydrocarbon group which may be substituted, a hydroxy group which may be substituted or an acyl group;

(4) A compound as shown in the above item (1), wherein $R^3$, $R^4$, $R^5$, $R^6$, $R^7$, $R^8$ and $R^9$ are independently a hydrogen atom, a hydrocarbon group which may be substituted, a hydroxy group which may be substituted, or a halogen atom;

(5) A compound as shown in the above item (1), wherein $A^1$ is a 4- or 5-imidazolyl group which may be substituted or a 3- or 4-pyridyl group which may be substituted;

(6) A compound as shown in the above item (1), wherein $A^1$ is a 4- or 5-imidazolyl group which may be substituted with ① a $C_{1-4}$alkyl group unsubstituted or substituted with a $C_{1-4}$alkanoyl, carboxyl, or a $C_{1-4}$alkoxy-carbonyl, ② a $C_{1-3}$alkoxy group, ③ a $C_{1-6}$alkanoyl ④ $C_{1-4}$alkylsulfonyl, ⑤ carbamoyl, a mono- or di-$C_{1-10}$alkyl carbamoyl group, a mono- or di-$C_{6-14}$arylcarbamoyl group or a mono- or di-$C_{7-16}$aralkylcarbamoyl group, or ⑥ sulfamoyl, a mono- or di-$C_{1-10}$alkyl sulfamoyl group, a mono- or di-$C_{6-14}$arylsulfamoyl group, or a mono- or di-$C_{7-16}$aralkyl sulfamoyl group;

(7) A compound as shown in the above item (1), wherein $A^1$ is a 3- or 4-pyridyl group which may be substituted with ① a $C_{1-4}$alkyl group unsubstituted or substituted with a $C_{1-4}$alkanoyl, carboxyl, or a $C_{1-4}$alkoxy-carbonyl, ② a $C_{1-3}$alkoxy group, ③ a $C_{1-6}$alkanoyl ④ $C_{1-4}$alkylsulfonyl, ⑤ carbamoyl, a mono- or di-$C_{1-10}$alkyl carbamoyl group, a mono- or di-$C_{6-14}$arylcarbamoyl group or a mono- or di-$C_{7-16}$aralkylcarbamoyl group, or ⑥ sulfamoyl, a mono- or di-$C_{1-10}$alkyl sulfamoyl group, a mono- or di-$C_{6-14}$arylsulfamoyl group, or a mono- or di-$C_{7-16}$aralkyl sulfamoyl group;

(8) A compound as shown in the above item (1), wherein $A^1$ is a thiazolyl group which may be substituted;

(9) A compound as shown in the above item (1), wherein $R^{21}$ is a hydrogen atom or a lower alkyl group;

(10) A compound as shown in the above item (1), wherein $R^{21}$ is a hydrogen atom;

(11) A compound as shown in the above item (1), wherein one to three groups of $R^3$, $R^4$, $R^5$, $R^6$, $R^7$, $R^8$ and $R^9$ are independently a hydrocarbon group which may be substituted, a hydroxy group which may be substituted, an amino group which may be substituted, an acyl group or a halogen atom;

(12) A compound as shown in the above item (1), wherein one to three groups of $R^3$, $R^4$, $R^5$, $R^6$, $R^7$, $R^8$ and $R^9$ are independently a $C_{1-6}$alkyl group which may be substituted, a hydroxy group which may be substituted or a $C_{1-6}$acyl group;

(13) A compound as shown in the above item (1), wherein $R^{11}$ is a hydrogen atom, a lower alkyl group which may be substituted, a phenyl group which may be substituted or a pyridyl group which may be substituted;

(14) A compound as shown in the above item (1), wherein $R^{11}$ is a hydrogen atom, a lower alkenyl group, a cyclic alkyl group, a phenyl group, a pyridyl group, or a lower alkyl group which may be substituted with halogen atom(s);

(15) A compound as shown in the above item (1), wherein $R^{11}$ is an $C_{1-6}$alkyl group and $R^{21}$ is a hydrogen atom;

(16) A compound as shown in the above item (1), wherein $R^{11}$ is an isopropyl group and $R^{21}$ is a hydrogen atom;

(17) A compound as shown in the above item (1), wherein $R^7$ is a hydroxy group which may be substituted or a lower alkyl group;

(18) A compound as shown in the above item (1), wherein $R^7$ is (1) a hydroxy group which may be substituted with a lower alkanoyl group, a lower alkanoyloxy-lower alkyl group, a lower alkyl group, a lower alkoxy-lower alkyl group, a lower alkyl group which may have one to 4 halogen atoms (e.g. fluorine atoms), or a benzyl group, (2) a halogen atom, (3) a lower alkyl group which may be substituted with a hydroxy group, (4) a lower alkynyl group, (5) a lower alkanoyl group, (6) an amino group which may be substituted with a lower alkanoyl group, a lower alkylaminocarbonyl group or a lower alkylsulfonyl group, or (7) a lower alkylthio group;

(19) A compound as shown in the above item (1), wherein $R^7$ is a lower alkyl group, a lower alkoxy group or a lower alkanoylamino group;

(20) A compound as shown in the above item (1), wherein $R^7$ is a methoxy group;

(21) A compound as shown in the above item (1), wherein $R^8$ is a hydrogen atom, a lower alkyl group or a lower alkoxy group;

(22) A compound as shown in the above item (1), wherein $R^8$ is a hydrogen atom or a lower alkoxy group;

(23) A compound as shown in the above item (1), wherein $R^6$ is (1) a hydrogen atom (2) a halogen atom (3) a lower alkoxy group or (4) a lower alkyl group which may be substituted with a hydroxy group;

(24) A compound as shown in the above item (1), wherein $R^6$ is a hydrogen atom or a lower alkyl group;

(25) A compound as shown in the above item (1), wherein one of $R^6$, $R^7$ and $R^8$ is a lower alkyl group or a lower alkoxy group;

(26) A compound as shown in the above item (1), wherein each of $R^3$, $R^4$, $R^5$ and $R^9$ is a hydrogen atom;

(27) A prodrug of a compound shown in the above item (1);

(28) A compound as shown in the above item (1), which is 1-(1H-imidazol-4-yl-1-(6-methoxynaphthalen-2-yl)-2-methyl-1-propanol, 1-(6,7-dimethoxynaphthalen-2-yl)-1-(1H-imidazol-4-yl)-2-methyl-1-propanol, 1-(6-methoxy-5-methylnaphthalen-2-yl)-1-(1H-imidazol-4-yl)-2-methyl-1-propanol, N-{6-[1-hydroxy-1-(1H-imidazol-4-yl)-2-methylpropyl]naphthalen-2-yl}acetamide or 1-(6-ethylnaphthalen-2-yl)-1-(1H-imidazol-4-yl)-2-methyl-1-propanol or a salt thereof;

(29) A pharmaceutical composition containing a compound shown in the above item (1) or prodrug shown in the above item (27);

(30) A steroid $C_{17,20}$-lyase inhibitory composition containing a compound of the formula:

(I)

wherein A is a nitrogen-containing heterocyclic group which may be substituted, $R^1$ is a hydrogen atom, hydrocarbon group which may be substituted, or monocyclic aromatic heterocyclic group which may be substituted, $R^2$ is a hydrogen atom or a lower alkyl group which may be substituted, $R^3$, $R^4$, $R^5$, $R^6$, $R^7$, $R^8$ and $R^9$ are independently a hydrogen atom, a hydrocarbon group which may be substituted, a hydroxy group which may be substituted, a thiol group which may be substituted, an amino group which may be substituted, an acyl group or a halogen atom, a salt thereof or a prodrug thereof;

(31) A composition as shown in the above item (30), which is an antitumor agent;

(32) A composition for an antitumor agent as shown in the above item (1), wherein the antitumor agent is a treating or preventing breast cancer or prostate cancer;

(33) A method for treating or preventing a disease whose exacerbation factor is androgen or estrogen, which comprises administering an effective amount of a compound of the formula (I'), a salt thereof or a prodrug thereof, optionally together with a pharmaceutically acceptable carrier, diluent or excipient, to a patient suffering from the disease;

(34) A method for treating or preventing a disease whose exacerbation factor is androgen or estrogen, which comprises administering an effective amount of a compound of the formula (I), a salt thereof or a prodrug thereof, optionally together with a pharmaceutically acceptable carrier, diluent or excipient, to a patient suffering from the disease;

(35) A method as shown in the above item (34) wherein the diseases whose exacerbation factor is androgen or estrogen is a cancer;

(36) A method as shown in the above item (34), wherein the cancer is breast cancer or prostate cancer;

(37) Use of a compound of the formula (I') a salt thereof or a prodrug thereof for the production of a pharmaceutical composition;

(38) Use of a compound of the formula (I) a salt thereof or a prodrug thereof for the production of a steroid $C_{17,20}$-lyase inhibitory composition;

(39) Use as shown in the above item (38), wherein the composition is for treating or preventing a cancer;

(40) Use as shown in the above item (38), wherein the composition is for treating or preventing of breast cancer or prostate cancer;

(41) A compound of the formula:

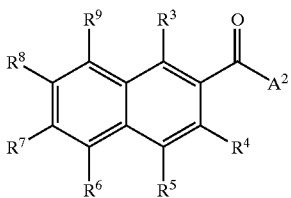

(II')

wherein $A^2$ is an imidazolyl group which may be substituted, $R^3$, $R^4$, $R^5$, $R^6$, $R^7$, $R^8$ and $R^9$ are independently a hydrogen atom, a hydrocarbon group which may be substituted, a hydroxy group which may be substituted, a thiol group which may be substituted, an amino group which may be substituted, an amino group which may be substituted, an acyl group or a halogen atom, or a salt thereof;

(42) A process for producing a compound of the formula:

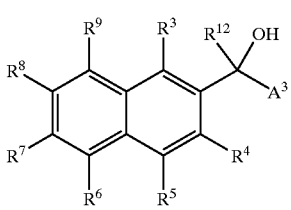

(Ib)

wherein $A^3$ is an imidazolyl group, a thiazolyl group or an oxazolyl group, each of which may be substituted, $R^3$, $R^4$, $R^5$, $R^6$, $R^7$, $R^8$ and $R^9$ are independently a hydrogen atom, a hydrocarbon group which may be substituted, a hydroxy group which may be substituted, a thiol group which may be substituted, an amino group which may be substituted, an acyl group or a halogen atom, and $R^{12}$ is a hydrocarbon group which may be substituted, or a monocyclic aromatic heterocyclic group which may be substituted, or a salt thereof, which comprises reacting a compound of the formula:

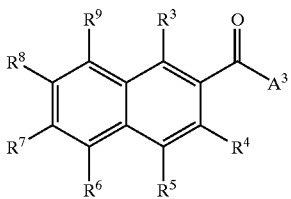

(II)

wherein each symbol has the same meaning as defined above, or a salt thereof with a compound of the formula:

$$R^{12}—M \quad (III)$$

wherein M is a metal or a salt thereof and $R^{12}$ has the same meaning as defined above.

In the above formulas, as the "nitrogen-containing heterocyclic group" in the "nitrogen-containing heterocyclic group which may be substituted" shown by A, there may be mentioned a nitrogen-containing aromatic heterocyclic group, a saturated or unsaturated nitrogen-containing non-aromatic heterocyclic group (a nitrogen-containing aliphatic heterocyclic group) having at least a nitrogen atom as the ring constituting atoms, preferably a nitrogen-containing aromatic heterocyclic group. As the nitrogen-containing aromatic heterocyclic group, there may be mentioned a nitrogen-containing 5- or 6-membered aromatic heterocyclic group such as imidazolyl, pyrrolyl, pyrazolyl, 1,2,3-triazolyl, 1,2,4-triazolyl, tetrazolyl, thiazolyl, isothiazolyl, oxazolyl, isoxazolyl, pyridyl, pyridazinyl, pyrimidinyl, pyrazinyl, 1,3,5-triazinyl, 1,2,4-triazinyl. Among them, imidazolyl, pyridyl, thiazolyl, oxazolyl, etc., are preferable and 4 or 5-imidazolyl group and 3 or 4-pyridyl group are the most preferable.

In the "nitrogen-containing aromatic heterocyclic group which may be substituted" shown by A, one to three substituents may be substituted at any position on the nitrogen-containing aromatic heterocyclic group. As the substituent, there may be mentioned a lower alkyl group which may be substituted, a lower alkoxy group, an acyl group, etc. Examples of the lower alkyl which may be substituted include, an unsubstituted $C_{1-4}$alkyl group such as methyl, ethyl, propyl, etc., and an $C_{1-4}$alkyl group substituted by an $C_{1-4}$alkanoyl such as acetyl, propionyl, etc., carboxyl, a $C_{1-4}$alkoxy-carbonyl (e.g. methoxycarbonyl, ethoxycarbonyl, butoxycarbonyl, etc.), etc. As the lower alkoxy group, there maybe mentioned, for example, a $C_{1-3}$alkoxy group such as methoxy, ethoxy, propoxy, isopropoxy, etc. As the acyl group, there may be mentioned, for example, an alkanoyl group (e.g. such a $C_{1-6}$alkanoyl as formyl, acetyl, propionyl, etc.), an alkylsulfonyl group (e.g. such a $C_{1-4}$alkylsulfonyl as methylsulfonyl, ethylsulfonyl, etc.), a carbamoyl group which may be substituted (e.g. such a mono- or di-$C_{1-10}$alkyl carbamoyl group as methylcarbamoyl, ethylcarbamoyl, dimeothylcarbamoyl, diethylcarbamoyl, etc., such a mono- or di-$C_{6-14}$arylcarbamoyl as phenylcarbamoyl, diphenylcarbamoyl, etc., such a mono- or di-$C_{7-16}$aralkylcarbamoyl group as benzylcarbamoyl, dibenzylcarbamoyl, etc.), a sulfamoyl which may be substituted (e.g. such a mono- or di-$C_{1-10}$alkyl sulfamoyl group as methylsulfamoyl, ethylsulfamoyl, dimethylsulfamoyl, diethylsulfamoyl, etc., such a mono- or di-$C_{6-14}$arylsulfamoyl group as phenylsulfamoyl, diphenylsulfamoyl, etc., such a mono- or di-$C_{7-16}$aralkyl sulfamoyl group as benzylsulfamoyl, dibenzylsulfamoyl, etc.), etc.

The imidazolyl group which may be substituted, the thiazolyl group which may be substituted, the oxazolyl group which may be substituted and the pyridyl group which may be substituted, represented by $A^1$ have the same meaning as the imidazolyl group which may be substituted, the thiazolyl group which may be substituted, the oxazolyl group which may be substituted and the pyridyl group which may be substituted, respectively, each of which may be mentioned in the definition of the nitrogen-containing heterocyclic group which may be substituted represented by A. The preferable examples of $A^1$ are the preferable examples mentioned in the definition of A and included in the definition of $A^1$.

The imidazolyl group which may be substituted represented by $A^2$ has the same meaning as the imidazolyl group which may be substituted which may be mentioned in the definition of the nitrogen-containing heterocyclic group which maybe substituted represented by A. The preferable examples of $A^2$ are the preferable examples mentioned in the definition of A and included in the definition of $A^2$.

The imidazolyl group which may be substituted, the thiazolyl group which may be substituted and the oxazolyl group which may be substituted, represented by $A^3$ have the same meaning as the imidazolyl group which may be substituted, the thiazolyl group which may be substituted and the oxazolyl group which may be substituted, which may be mentioned in the definition of the nitrogen-containing heterocyclic group which may be substituted represented by A. The preferable examples of $A^2$ are the preferable examples mentioned in the definition of A and included in the definition of $A^3$.

Examples of the hydrocarbon group in the definition of "hydrocarbon group which may be substituted" shown by $R^1$ include, for example, an aliphatic hydrocarbon group, a cyclic hydrocarbon group, etc. Examples of the aliphatic hydrocarbon group include, for example, a straight chain or branched aliphatic hydrocarbon group having 1 to 10 carbon atoms such as an alkyl group, an alkenyl group, etc. Among them, an alkyl group is preferable. Examples of the alkyl group include, for example, a $C_{1-10}$alkyl group, such as methyl, ethyl, n-propyl, isopropyl, butyl, isobutyl, sec-butyl, tert-butyl, n-pentyl, isopentyl, neopentyl, n-hexyl, isohexyl, etc. Among them, a $C_{1-6}$alkyl group (for example, methyl, ethyl, n-propyl, isopropyl, n-butyl, sec-butyl, tert-butyl, etc.) is preferable. Examples of the alkenyl group include, for example, a $C_{2-10}$alkenyl group such as vinyl, 1-propenyl, allyl, isopropenyl, 1-butenyl, 2-butenyl, 3-butenyl, isobutenyl, sec-butenyl, etc. Among them, a $C_{2-6}$alkenyl group (for example, vinyl, 1-propenyl, allyl, etc.) is preferable. Examples of the alkynyl group include, for example, a $C_{2-10}$alkynyl group such as ethynyl, 1-propynyl, propargyl, etc. is preferable. Among them, a $C_{2-6}$alkynyl group (for example, ethynyl, etc.) is preferable.

Examples of the cyclic hydrocarbon group are one having 3 to 18 carbon atoms and include, for example, an aliphatic cyclic hydrocarbon group, an aromatic hydrocarbon group, etc. Examples of the aliphatic cyclic hydrocarbon group include, for example, a monocyclic or condensed polycyclic group consisting of 3 to 10 carbon atoms. Examples of the embodiment include a cycloalkyl group, a cycloalkenyl group, a bi- or tri-cyclic condensed ring formed by condensing one of them with a $C_{6-14}$aryl group (for example, benzene, etc.), etc. Examples of the cycloalkyl group include, for example, a $C_{3-6}$cycloalkyl group such as cyclopropyl, cyclobutyl, cyclopentyl, cyclohexyl, etc. Examples of the cycloalkenyl group include, for example, a $C_{3-6}$cycloalkenyl group such as cyclopropenyl, cyclobutenyl, cyclopentehyl, cyclohexenyl, etc.

Examples of the aromatic hydrocarbon group include a monocyclic aromatic hydrocarbon group, a condensed polycyclic aromatic hydrocarbon group, etc., each of which is constituted with 6 to 18 carbon atoms. Examples of the embodiment include a $C_{6-14}$aryl group such as phenyl, 1-naphthyl, 2-naphthyl, 2-indenyl, 2-anthryl, etc. Among them, a $C_{6-10}$aryl group (for example, phenyl, etc.) is preferable. Examples of the substituent which substitutes on the aliphatic hydrocarbon group in the definition of "hydrocarbon group which may be substituted" are not limited but include, for example, a halogen atom, a hydroxy group, an alkoxy group, an acyloxy group, an alkylthio group, an acylamino group, a carboxyl group, an alkoxycarbonyl group, an oxo group, an alkylcarbonyl group, a cycloalkyl group, an aryl group, an aromatic heterocyclic group, etc. These substituents may substitute on the aliphatic hydrocarbon group in a chemically acceptable range. The number of the substituent is usually 1 to 5 and preferably 1 to 3. When the number of substituents is more than two, the substituents may be the same or different from each other.

Examples of the substituent which substitutes on the cyclic hydrocarbon group in the definition of "hydrocarbon group which may be substituted" are not limited but include, for example, a halogen atom, a hydroxy group, an alkoxy group, an acyloxy group, an alkylthio group, an alkylsulfonyl group, a mono- or dialkylamino group, an acylamino group, a carboxyl group, an alkoxycarbonyl group, an alkynylcarbonyl group, an alkyl group, a cycloalkyl group, an aryl group, an aromatic heterocyclic group, etc.

These substituents may substitute on the aliphatic hydrocarbon group in a chemically acceptable range. The number of the substituents is usually 1 to 5 and preferably 1 to 3. When the number of substituents is more than two, the substituents may be the same or different from each other.

Examples of the halogen atom include fluorine, chlorine, bromine, iodine.

Examples of the alkoxy group include, for example, a $C_{1-10}$alkoxy group such as methoxy, ethoxy, propoxy, isopropoxy, butoxy, isobutoxy, sec-butoxy, pentyloxy, hexyloxy, etc. Examples of the acyloxy group include, for example, formyloxy, a $C_{1-10}$alkyl-carbonyloxy (for example, acetoxy, propionyloxy, etc.), etc. Examples of the alkylthio group include, for example, a $C_{1-10}$alkylthio group such as methylthio, ethylthio, propylthio, isopropylthio, etc. Examples of the alkylsulfonyl group include, for example, a $C_{1-10}$alkylsulfonyl group such as methylsulfonyl, ethylsulfonyl, propylsulfonyl, etc. Examples of the acyl amino group include, for example, formylamino, diformylamino, a mono- or di-$C_{1-10}$alkyl-carbonylamino (for example, acetylamino, propionylamino, butyrylamino, diacetylamino, etc.), etc. Examples of the alkoxycarbonyl group include, for example, a $C_{1-10}$alkoxycarbonyl group such as methoxycarbonyl, ethoxycarbonyl, propoxycarbonyl, isopropoxycarbonyl, butoxycarbonyl, etc. Examples of the alkylcarbonyl group include, for example, a $C_{1-10}$alkylcarbonyl group such as acetyl, propionyl, butyryl, valeryl, etc. Examples of the alkynylcarbonyl group include for example, a $C_{3-10}$alkynylcarbonyl group, such as acetylenylcarbonyl, 1-propynylcarbonyl, 2-propynylcarbonyl, etc.

Examples of the cycloalkyl group include, for example, a $C_{3-10}$cycloalkyl group such as cyclopropyl, cyclobutyl, cyclopentyl, cyclohexyl, etc. Examples of the aryl group include, for example, a $C_{6-14}$aryl group such as phenyl, 1-naphthyl, 2-naphthyl, etc. Examples of the aromatic heterocyclic group include, for example, a mono- to tri-cyclic aromatic heterocyclic group containing one or two kinds of hetero atoms and preferably 1 to 4 hetero atoms selected from the group consisting of nitrogen, oxygen and sulfur. Examples of the embodiment include, for example, thienyl, pyridyl, furyl, pyrazinyl, pyrimidinyl, imidazolyl, pyrazolyl, thiazolyl, isothiazolyl, oxazolyl, isoxazolyl, pyridazinyl, tetrazolyl, quinolyl, indolyl, isoindolyl, etc. Examples of the alkyl group include, for example, a $C_{1-10}$alkyl group such as methyl, ethyl, propyl, isopropyl, butyl, sec-butyl, tert-butyl, pentyl, etc.

Examples of the substituent which substitutes on the hydrocarbon group mentioned above also include the following substituents, the number of the substituents is 1 to 5, preferably 1 to 3. Examples of the substituents include, for example, a halogen atom (for example, fluorine, chlorine, bromine, etc.), a hydroxy group, $C_{1-6}$alkoxy group (for example, methoxy, ethoxy, propoxy, isopropoxy, etc.), etc.

Examples of the monocyclic aromatic heterocyclic group in the definition of "monocyclic aromatic heterocyclic group which may be substituted" shown by $R^1$ include, for example, 2-thienyl, 3-thienyl, 2-pyridyl, 3-pyridyl, 4-pyridyl, 2-furyl, 3-furyl, pyrazinyl, 2-pyrimidinyl, 3-pyrrolyl, 1-imidazolyl, 2-imidazolyl, 4-imidazolyl, 5-imidazolyl, 1-pyrazolyl, 2-thiazolyl, 4-thiazolyl, 5-thiazolyl, 3-isothiazolyl, 4-isothiazolyl, 2-oxazolyl, 4-oxazolyl, 5-oxazolyl, 3-isoxazolyl, 3-pyridazinyl, etc. Among them, 2-pyridyl, 3-pyridyl, 4-pyridyl, 1-imidazolyl, 4-imidazolyl, etc., are preferable.

The substituent of "monocyclic aromatic heterocyclic group which may be substituted" in the definition $R^1$ may substitute at the substitutable position of the monocyclic aromatic heterocyclic group. The number of the substituents is 1 to 3. Examples of the substituents include an alkyl group which may be substituted by 1 to 5 halogen atoms (e.g. fluorine, chlorine, bromine, iodine) (e.g. such a $C_{1-4}$alkyl as methyl, ethyl, propyl, etc., such a $C_{1-4}$alkyl substituted by halogen as 2,2,2-trifluoroethyl, 2,2,3,3,3-pentafluoropropyl, etc.), a $C_{1-3}$alkyl group such as methyl, ethyl, propyl, isopropyl, etc., a $C_{1-3}$alkoxy group such as methoxy, ethoxy, propoxy, isopropoxy, etc., a halogen atom such as a chlorine atom, a fluorine atom, etc., a hydroxy group, an amino group, a nitro group, etc.

The preferable Examples of $R^1$ include a hydrogen atom, a lower($C_{1-4}$)alkyl group which may be substituted, a lower ($C_{1-14}$)alkenyl group, a cyclic($C_{3-6}$)alkyl group, a phenyl group which may be substituted and a pyridyl group which may be substituted each of which is mentioned above. Among them, a hydrogen atom, a lower($C_{1-4}$)alkenyl group, a cyclic($C_{3-6}$)alkyl group, a phenyl group, a pyridyl group and a lower($C_{1-14}$)alkyl group which may be substituted with halogen(s) are the most preferable.

The saturated hydrocarbon group which may be substituted and the monocyclic aromatic heterocyclic group which may be substituted represented by $R^{11}$ have the same meaning as the hydrocarbon group which may be substituted and the monocyclic aromatic heterocyclic group which may be substituted, mentioned in the definition of $R^1$ and included in the definition of $R^{11}$. The preferable examples of $R^{11}$ are the preferable examples mentioned in the definition of $R^1$ and included in the definition of $R^{11}$.

The saturated hydrocarbon group which may be substituted and the monocyclic aromatic heterocyclic group which may be substituted represented by $R^{12}$ have the same meaning as those mentioned in the definition of $R^1$.

Examples of the lower alkyl group shown by $R^2$ include a straight chain or cyclic $C_{1-6}$alkyl group (e.g. methyl, ethyl, propyl, isopropyl, cyclopropyl, butyl, isobutyl, sec-butyl, tert-butyl, pentyl, cyclopentyl, hexyl, etc.) which may be substituted. The $C_{1-6}$alkyl group may be substituted by 1 to 5 substituents at any position. Examples of the substituents include, for example, a halogen (e.g. fluorine, chlorine, bromine, etc.), a $C_{1-4}$alkoxy group (e.g. methoxy, ethoxy, propoxy, etc.), etc.

Preferable examples of $R^2$ include a hydrogen atom and a non-substituted lower($C_{1-6}$)alkyl group among the lower alkyl group mentioned above, and a hydrogen atom is the most preferable.

The lower alkyl group which may be substituted represented by $R^{21}$ has the same meaning as that mentioned in the definition of $R^2$.

The preferable examples of $R^{21}$ are the preferable examples mentioned in the definition of $R^{21}$ and an included in the definition of $R^{21}$.

Examples of the hydroxy group which may be substituted shown by $R^3, R^4, R^5, R^6, R^7, R^8, R^9$ include an unsubstituted hydroxy group, a lower alkoxy (e.g. a $C_{1-4}$alkoxy group such as methoxy, ethoxy, propoxy, etc.), a lower alkanoyloxy (e.g. a $C_{1-4}$alkanoyloxy such as acetyloxy, propionyloxy, etc.), a carbamoyloxy which may be substituted (e.g. unsubstituted carbamoyloxy, methylcarbamoyloxy, ethylcarbamoyloxy, dimethylcarbamoyloxy, diethylcarbamoyloxy, methylethylcarbamoyloxy, etc., a carbamoyloxy substituted by 1 or 2 $C_{1-4}$alkyl group), etc.

Examples of the thiol group which may be substituted shown by $R^3, R^4, R^5, R^6, R^7, R^8, R^9$ include unsubstituted thiol group, a lower alkylthio (e.g. a $C_{1-4}$alkylthio group such as methylthio, ethylthio, propylthio, etc.), a lower alkanoylthio (e.g. a $C_{1-4}$alkanoylthio such as acetylthio, propionylthio, etc.), etc.

Examples of the amino group which may be substituted shown by $R^3, R^4, R^5, R^6, R^7, R^8, R^9$ include an unsubstituted amino group, a lower alkylamino (e.g. a $C_{1-4}$alkyl amino group such as methylamino, ethylamino, propylamino, etc.), a di-lower alkylamino (e.g. a di-$C_{1-4}$alkylamino such as dimethylamino, diethylamino, etc.), a $C_{1-4}$alkanoylamino (e.g. acetamide, propionamide, etc.), etc.

Examples of the acyl group represented by $R^3, R^4, R^5, R^6, R^7, R^8$ or $R^9$ include, for example, an alkanoyl group (e.g. formyl, a $C_{1-6}$alkanoyl such as acetyl, propionyl, etc.), an alkylsulfonyl group (e.g. $C_{1-4}$alkylsulfonyl such as methylsulfonyl, ethylsulfonyl, etc.), a carbamoyl group (mono- or di-$C_{1-10}$alkyl carbamoyl group such as methylcarbamoyl, ethylcarbamoyl, dimethylcarbamoyl, diethylcarbamoyl, etc., a mono- di-$C_{6-14}$arylcarbamoyl group such as phenylcarbamoyl, diphenylcarbamoyl, etc., a mono- di-$C_{7-16}$aralkyl carbamoyl group such as benzylcarbamoyl, dibenzylcarbamoyl, etc.), a sulfamoyl group which may be substituted (a mono- or di-$C_{1-10}$alkylsulfamoyl group such as methylsulfamoyl, ethylsulfamoyl, dimethylsulfamoyl, diethylsulfamoyl, etc., a mono- or di-$C_{6-14}$arylsulfamoyl group such as phenylsulfamoyl, diphenylsulfamoyl, etc., a mono- or di-$C_{7-16}$aralkyl sulfamoyl group such as benzylsulfamoyl, dibenzylsulfamoyl, etc.), etc.

Examples of the halogen shown by $R^3, R^4, R^5, R^6, R^7, R^8, R^9$ include fluorine, chlorine, bromine, iodine.

Examples of the hydrocarbon group which may be substituted shown by $R^3, R^4, R^5, R^6, R^7, R^8, R^9$ include the same one as the hydrocarbon group which may be substituted shown by $R^1$. Among them, a lower alkyl group which may be substituted is preferable. Examples of the embodiment include a straight or cyclic $C_{1-6}$alkyl group (e.g. methyl, ethyl, propyl, isopropyl, cyclopropyl, butyl, isobutyl, sec-butyl, tert-butyl, pentyl, cyclopentyl, hexyl, etc.) which may be substituted. The $C_{1-6}$alkyl group may be substituted by 1 to 5 substituents at any position. Examples of the substituent include, for example, a halogen (e.g. fluorine, chlorine, bromine, etc.), a $C_{1-4}$alkoxy group (e.g. methoxy, ethoxy, propoxy, etc.), a hydroxy group, etc. Examples of the lower alkoxy group which may be substituted include methoxy, ethoxy, propoxy, etc. The lower alkoxy group may be substituted by 1 to 5 substituents at any position. Examples of the substituents include, for example, a halogen (e.g. fluorine, chlorine, bromine, etc.), $C_{1-4}$alkoxy group (e.g. methoxy, ethoxy, propoxy, etc.), etc. Preferable example of $R^3, R^4, R^5, R^6, R^7, R^8$ or $R^9$ include, for example, a hydrogen atom, a hydrocarbon group which may be substituted, a hydroxy group which may be substituted, an amino group which may be substituted, a $C_{1-6}$acyl group or a halogen atom each of which is mentioned above, and among them, a hydrogen atom, a hydrocarbon group which may be substituted, a hydroxy group which may be substituted, an acyl group and a halogen atom are more preferable.

As $R^7$, a hydroxy group which may be substituted and a lower alkyl group are preferable, and (1) a hydroxyl group which may be substituted with a lower alkanoyl group, a lower alkanoyloxy-lower alkyl group, a lower alkyl group, a lower alkoxy-lower alkyl group, a lower alkyl group having 1 to 4 fluorine atoms or a benzyl group, (2) a halogen atoms, (3) a lower alkyl group which may be substituted with a hydroxyl group, (4) a lower alkynyl group, (5)a lower alkanoyl group, (6)an amino group which may be substituted with a lower alkanoyl group, a lower alkylaminocarbonyl group or a lower alkylsulfonyl group, or (7) a lower alkylthio group is more preferable. Among them, a lower alkyl group, a lower alkoxy group and a lower alkanoylamino group are more preferable and a methoxy group is the most preferable.

As $R^8$, hydrogen atom, a lower alkyl group and a lower alkoxy are preferable and hydrogen atom and a lower alkoxy are more preferable. As $R^6$, (1) a hydrogen atom, (2) halogen atom, (3) a lower alkoxy group and (4) a lower alkyl group which may be substituted with a hydroxyl group are preferable, and a hydrogen atom and a lower alkyl group are more preferable.

It is preferable that one to three groups selected from the group consisting of $R^3$, $R^4$, $R^5$, $R^6$, $R^7$, $R^8$ and $R^9$ are independently a lower alkyl group which may be substituted, a hydroxyl group which may be substituted, an amino group which may be substituted, an acyl group or a halogen atom.

It is more preferable that one to three groups selected from the group consisting of $R^3$, $R^4$, $R^5$, $R^6$, $R^7$, $R^8$ and $R^9$ are independently a lower alkyl group which may be substituted, a hydroxyl group which may be substituted or a $C_{1-6}$acyl group.

It is preferable that one of $R^6$, $R^7$ and $R^8$ is a lower alkyl group or a lower alkoxy group, and each of $R^3$, $R^4$, $R^5$ and $R^9$ is a hydrogen atom.

Among Compound (I), a compound wherein $R^1$ is a $C_{1-6}$alkyl group and $R^{21}$ is a hydrogen atom is preferable, and a compound wherein $R^{11}$ is an isopropyl group and $R^{21}$ is a hydrogen atom is more preferable.

The preferable examples of the compound shown by the formula (I) include, for example, the compound of the formula

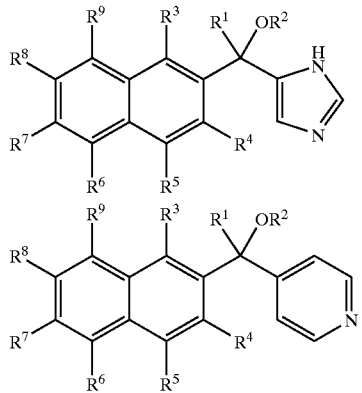

(wherein each of $R^1$, $R^2$, $R^3$, $R^4$, $R^5$, $R^6$, $R^7$, $R^8$ and $R^9$ has the meanings shown above). Preferable examples of the embodiments include, for example, 1-(1H-imidazol-4-yl-1-(6-methoxynaphthalen-2-yl)-2-methyl-1-propanol, 1-(6,7-dimethoxynaphthalen-2-yl)-1-(1H-imidazol-4-yl)-2-methyl-1-propanol, 1-(6-methoxy-5-methylnaphthalen-2-yl)-1-(1H-imidazol-4-yl)-2-methyl-1-propanol, N-{6-[1-hydroxy-1-(1H-imidazol-4-yl)-2-methylpropyl]naphthalen-2-yl}acetamide, 1-(6-ethylnaphthalen-2-yl)-1-(1H-imidazol-4-yl)-2-methyl-1-propanol and salts thereof or prodrugs thereof.

The compound of the formula (I) may be a salt. Examples of the salt include a salt of inorganic acid (for example, a hydrochloric acid salt, a sulfuric acid salt, a hydrobromic acid salt, a phosphoric acid salt, etc.), a salt of an organic acid (for example, an acetic acid salt, a trifluoroacetic acid salt, a succinic acid salt, a maleic acid salt, a fumaric acid salt, a propionic acid salt, a citric acid salt, a tartaric acid salt, a lactic acid salt, an oxalic acid salt, a methane sulfonic acid salt, a p-toluenesulfonic acid salt, etc.), etc., a salt with a base (for example, salt with an alkali metal such as a potassium salt, a sodium salt, a lithium salt, etc., an alkaline earth metal salt such as a calcium salt, a magnesium salt, etc., an ammonium salt, a salt with an organic base such as a trimethylamine salt, a triethyl amine salt, tert-butyldimethylamine salt, a dibenzylmethylamine salt, a benzyldimethylamine salt, a N,N-dimethylaniline salt, a pyridine salt, a quinoline salt, etc.).

The compound shown by (I) or a salt thereof may be a hydrate. Hereinafter these are referred to as Compound (I).

The pro-drug of Compound (I) means a compound which is converted to compound (I) having steroid $C_{17,20}$-lyase inhibitory activity by enzymes, gastric acid, etc. in vivo.

Examples of the pro-drug of a compound (I) include a compound wherein an amino group of Compound (I) is substituted with acyl, alkyl phosphoric acid, etc. (e.g. a compound wherein an amino group of Compound (I) is substituted with eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl, tert-butyl, etc.); a compound wherein an hydroxy group of Compound (I) is substituted with acyl, alkyl, phosphoric acid, boric acid, etc. (e.g. a compound wherein an hydroxy group of Compound (I) is substituted with acetyl, palmitoyl, propanoyl, pivaloyl, succinyl, fumaryl, alanyl, dimethylaminomethylcarbonyl, etc.); a compound wherein a carboxyl group of Compound (I) is modified with ester, amide, etc. (e.g. a compound wherein a carboxyl group of Compound (I) is modified with ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester, methyl amide, etc.); etc. These pro-drugs can be produced by per se known methods.

The pro-drug of Compound (I) may be a compound which is converted into Compound (I) under the physiological conditions as described in "Pharmaceutical Research and Development", Vol. 7 (Drug Design), pages 163–198 published in 1990 by Hirokawa Publishing Co. (Tokyo, Japan).

The compound (I) or a pro-drug thereof may be in the form of any pharmaceutically acceptable salts thereof. Examples of said salts include a salt with inorganic bases (e.g., alkaline metals such as sodium, potassium, etc.; alkaline earth metals such as calcium, magnesium, etc.; transition metal such as zinc, iron, copper, etc.; etc.); organic bases (e.g., organic amines such as trimethylamine, triethylamine, pyridine, picoline, ethanolamine, diethanolamine, triethanolamine, dicyclohexylamine, N,N'-dibenzylethylenediamine, etc.; basic amino acids such as arginine, lysine, ornithine, etc.; etc.); etc., when said compound (I) has an acidic group such as a carboxyl group, etc.; and a salt with inorganic acids ororganic acids (e.g., hydrochloric acid, nitric acid, sulfuric acid, phosphoric acid, carbonic acid, bicarbonic acid, formic acid, acetic acid, propionic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.); acidic amino acids such as aspartic acid, glutamic acid, etc.; etc., when said compound (I) has a basic group such as an amino group, etc.

Also, Compound (I) may behydtated.

Compound (I) may have one or more asymmetric carbons in the molecule. The compound of the present invention may have R-configuration or S-configuration as to the asymmetric carbons.

The "lower" in "a lower alkyl group", "a lower alkoxy group", etc., throughout the present specification means a straight, branched or cyclic ones having 1 to 6 carbon otherwise mentioned.

In the present application, the compounds of the formulas (I'), (Ia), (Ib) and (Ic) are included in the compounds of the formula (I), and the compounds of the formula (II') are included in the compounds of the formula (II). Among the compound shown by the formulas (Ia), (Ib), (Ic), (II), (II'), (III), (IVa), (IVb), (IVc1), (IVc2), (IVd), (IVe1), (IVe2), (IVf), (Vb), (Vd), (VIa), (VIb), (VIc), (VId), (VIe) (VIf), (VIg), (VIIa), (VIIb) and (VIIc), compounds having a basic group or an acidic group can form a salt with acid or a salt with base, respectively. Examples of the salts include the salts of the compound (I) mentioned above. Hereinafter the compound of the formula (Number of formula) and its salt are referred to as Compound (Number of formula). For example, both a compound of formula (IVa) and a salt thereof are referred to as Compound (IVa).

Compound (I) can be produced, for example, by the following process steps.

The starting compound and an intermediate can be used as free form or a salt thereof like Compound (I). The reaction mixture as it is or after isolation by a known method can be used for the following reaction.

[wherein X is a halogen atom, L is a leaving group (e.g. a halogen atom, an alkyl or aryl sulfonyloxy group, etc.), $R^{22}$ is a lower alkyl group which may be substituted, $A^{11}$ is a nitrogen-containing heterocyclic group which may be protected or/and substituted, and each of the other symbols has the same meaning as defined above.]

Examples of the nitrogen-containing heterocyclic group which may be substituted in the definition of "nitrogen-containing heterocyclic group which may be protected or/and substituted shown by $A^{11}$ include the same as that mentioned above, and the protecting group is the same as that mentioned below.

Examples of the metal shown by M include lithium or magnesium, etc. Examples of the salt of metal shown by M include, for example, a metal halide such as magnesium chloride, magnesium bromide, etc.

The compound (IVa) is allowed to react with alkyl lithium or magnesium metal, etc., to give an organometal compound (IVb). The compound (IVb) is allowed to react with an aldehyde (IVe1) or (IVe2) to give a compound (IVc1) or (IVc2), respectively. Examples of the alkyl lithium used include a $C_{1-4}$alkyl lithium such as n-butyl lithium, s-butyl lithium, etc. The alkyl lithium is used in an amount of 1 to 3 moles, preferably 1 to 1.5 moles per one mole of the starting material (IVa). The reaction temperature in case of the reaction with alkyl lithium is in the range of $-100°$ C. to $0°$ C., preferably $-80°$ C. to $-20°$ C. The temperature in case of the reaction with magnesium metal is in the range of $-20°$ C. to $100°$ C., preferably $10°$ C. to $50°$ C. The reaction time

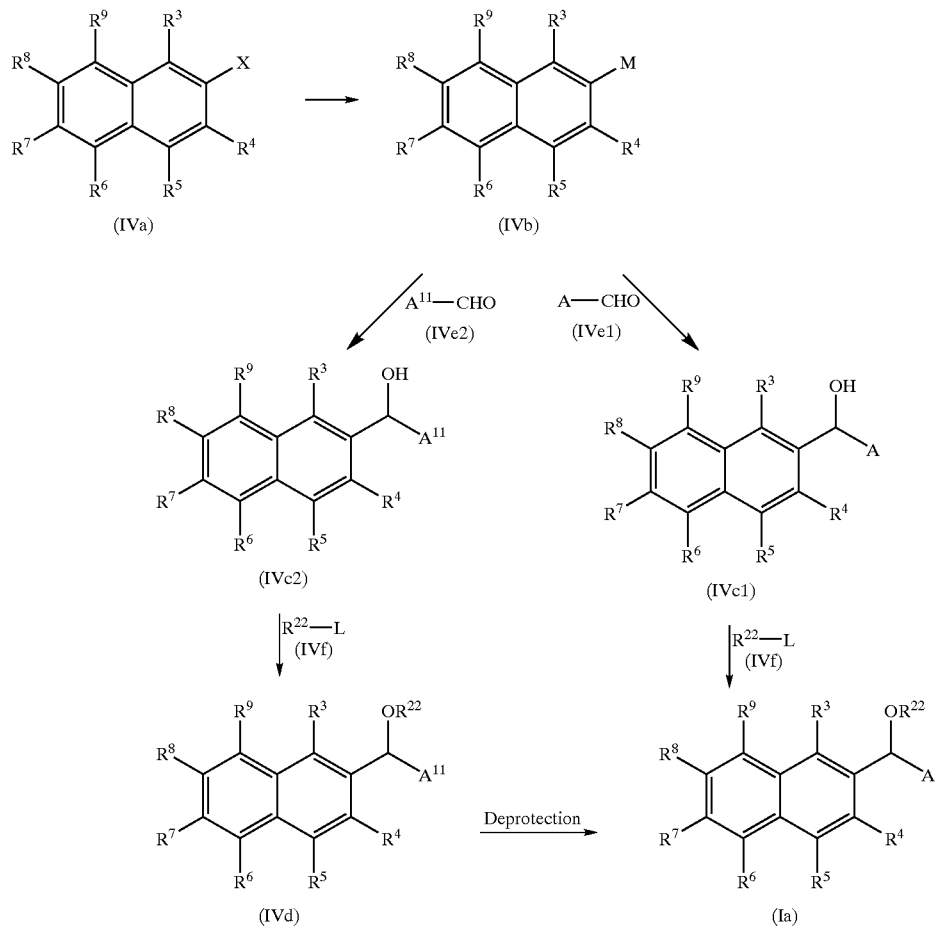

is about 5 min to 20 h. The reaction is usually carried out in the presence of an organic solvent which does not affect to the reaction. Examples of the organic solvent which does not affect to the reaction include, for example, an ether such as diethyl ether, dioxane, tetrahydrofuran (THF), etc., a saturated hydrocarbon such as hexane, pentane, etc., a halogenated hydrocarbon such as dichloromethane, chloroform, etc., an aromatic hydrocarbon such as benzene, toluene, etc. These solvent may be used solely or in combination of two or more in an appropriate ratio. The aldehyde compound (IVe1) or (IVe2) is used in 0.5 to 10 equivalents, preferably 0.5 to 1.5 equivalents to Compound (IVb).

Compound (IVc1) or (IVc2) is allowed to alkylation to give a Compound (IVd) or (Ia), respectively. Examples of the alkylating agents (IVf) used include an alkyl halide (e.g. methyl iodide, ethyl bromide, isopropyl bromide, etc.), an ester of an alkyl or an aryl sulfonic acid (e.g. methyl methanesulfonate, ethyl p-toluenesulfonate, etc.), etc. The alkylating agent can be used in an amount of 1 to 10 equivalents, preferably 1 to 2 equivalents to Compound (IVc1) or Compound (IVc2). The reaction is usually carried out in a basic condition. Examples of the base used include sodium hydride, potassium carbonate, sodium methylate, etc. The reaction is usually carried out in an inert solvent. Examples of the solvent include, for example, dimethylformamide, an ether such as tetrahydrofuran, etc., a halogenated hydrocarbon such as dichloromethane, etc. The reaction time is usually 30 min to 24 h, preferably 30 min to 10 h though it varies depend on the activity and amount of the alkylating agent and kind of the base. The reaction temperature is usually −20° C. to 150° C.

By a similar manner to a known method, Compound (IVd) is subjected to a de-protecting reaction which removes the protecting group of $A^{11}$ to give Compound (Ia). For example, Compound (IVd) wherein $A^{11}$ has a trityl group, that is, the nitrogen-containing heterocyclic group which may be substituted is protected by a trityl group, the compound can be treated under acidic conditions or undergo hydrogenolysis to remove the trityl group. Examples of the acid include an organic acid such as formic acid, acetic acid, etc., an inorganic acid such as hydrochloric acid, etc. The reaction can be carried out in an inert solvent such as an alcohol, an ether (e.g. tetrahydrofuran, etc.), etc. The reaction temperature is usually 0° C. to 100° C.

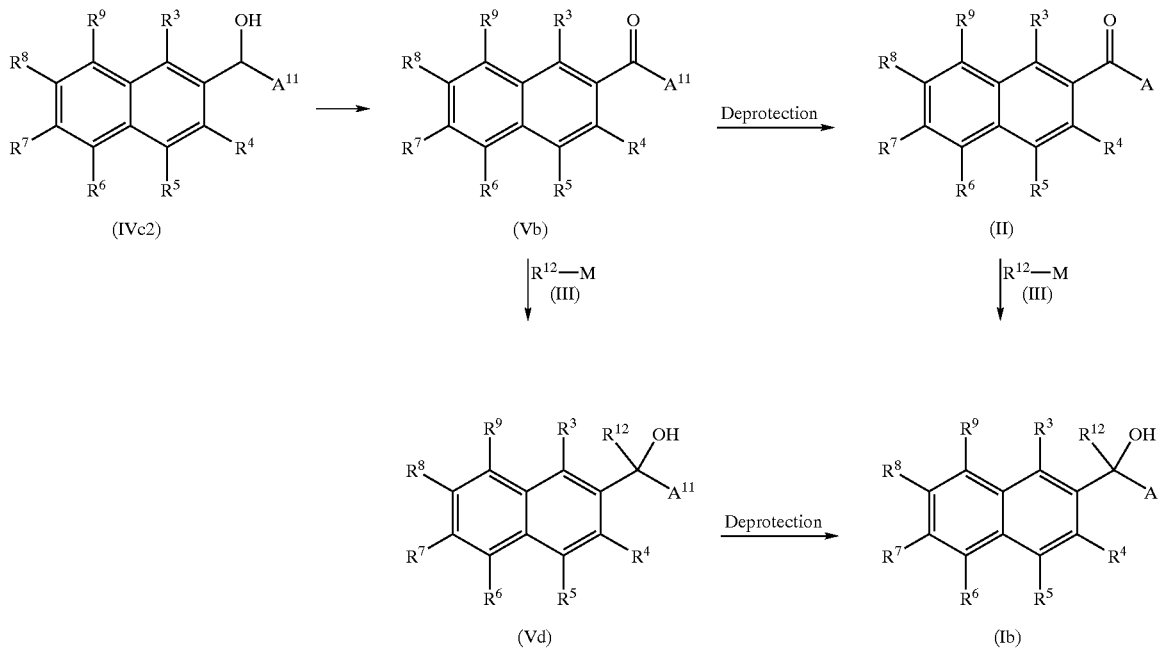

(wherein each symbol has the same meaning as defined above.)

Compound (IVc2) is allowed to usual oxidation reaction to give Compound (Vb). The reaction is carried out by using manganese dioxide, chromic acid, etc., as an oxidizing agent in an inert solvent such as dichloromethane, chloroform, THF, etc. The reaction time is usually 30 min to 48 h, preferably 30 min to 10 h. The reaction temperature is usually 0° C. to 100° C., preferably 20° C. to 70° C.

Compound (Vb) can be converted to Compound (II) by removing the protecting group By a similar manner to a known method. The elimination of the protecting group is carried out by a similar manner to the production of Compound (Ia) from Compound (IVd). Compound (II) is reacted with an organometal reagent (III) (an alkyl lithium reagent such as methyl lithium, etc., a Grignard reagent such as ethyl magnesium bromide, isopropyl magnesium chloride, etc.) to give Compound (Ib). The reaction can be carried out by a per se known manner or, for example, a manner shown in Shin-jikkenkagaku-koza Vol. 14, p512 (Maruzen Co. Japan) or a manner similar to these methods. The organometal reagent (III) is used in an amount of 1 to 10 equivalents, preferably 1 to 3 equivalents to the ketone (II). The reaction temperature is −100° C. to 50° C., preferably −80° C. to 20° C. The reaction time is 5 min to 20 h. The reaction is usually carried out in the presence of an organic solvent which does not affect to the reaction. Examples of the organic solvent which does not affect to the reaction include, for example, an ether such as diethyl ether, dioxane, tetrahydrofuran, etc., a saturated hydrocarbon such as hexane, pentane, etc., a halogenated hydrocarbon such as dichloromethane, chloroform, etc., an aromatic hydrocarbon such as benzene, toluene, etc. These solvent may be used solely or in combination of two or more in an appropriate ratio.

Compound (Ib) can also be produced by reacting Compound (Vb) with Compound (III) to give Compound (Vd), followed by subjecting Compound (Vd) to deprotection reaction.

pound (II). Compound (Vd) wherein the nitrogen-containing heterocyclic group is protected can be converted to Compound (Ib) by removing the protecting group by a similar manner to the production of Compound (Ia).

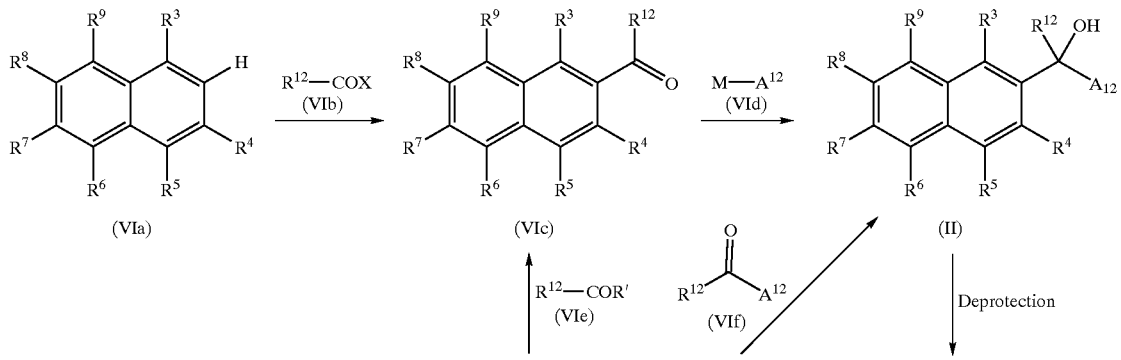

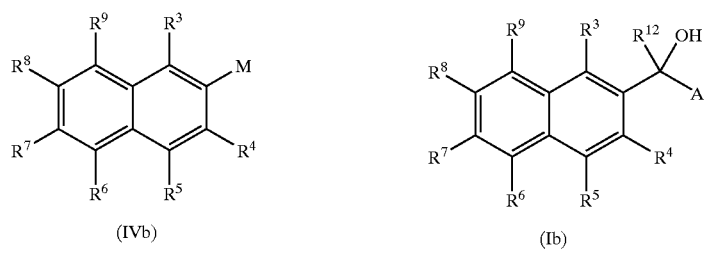

[wherein R' is a group shown by the formula: OR" or by the formula: NR"R'" (wherein each of R" and R'" is a lower alkyl group or a lower alkyloxy group. NR"R'" may be a cyclic amine residue such as a morpholino group, a pyrrolidino group, etc.), $A^{12}$ is a nitrogen-containing heterocyclic group which may be protected or/and substituted, and each of the other symbols has the same meaning as defined above.]

Examples of the nitrogen-containing heterocyclic group which may be protected or/and substituted among the nitrogen-containing heterocyclic group which may be protected or/and substituted shown by $A^{12}$, include the same as that mentioned about $A^{11}$, and that having no protecting group is the same as that mentioned about A.

Compound (VIa) is reacted with (VIb) by known Friedel-Crafts reaction, the manner shown in Shin-jikkenkagaku-koza Vol.14, p511 (Maruzen Co. Japan) or a manner similar to those manner, to give the carbonyl compound (VIc). Compound (VIc) can also be produced by reacting Compound (IVb) with Compound (VIe). The reaction is carried out in an inert solvent such as THF, dichloromethane, etc. Compound (IVb) is used in an amount of 0.2 to 2 equivalents, preferably 0.2 to 1.5 equivalents to Compound (VIe). The reaction temperature is −80° C. to 50° C., preferably −80° C. to 20° C.

Compound (Vd) can be produced by subjecting Compound (VIc) to alkylation reaction by using Compound (VId). The reaction can be carried out by a similar manner to the production of Compound (Ib) from Compound (II).

Compound (Vd) can also be produced by reacting an organometal reagent (IVb) with a ketone (VIf) By a similar manner to the production of Compound (Ib) from Com-

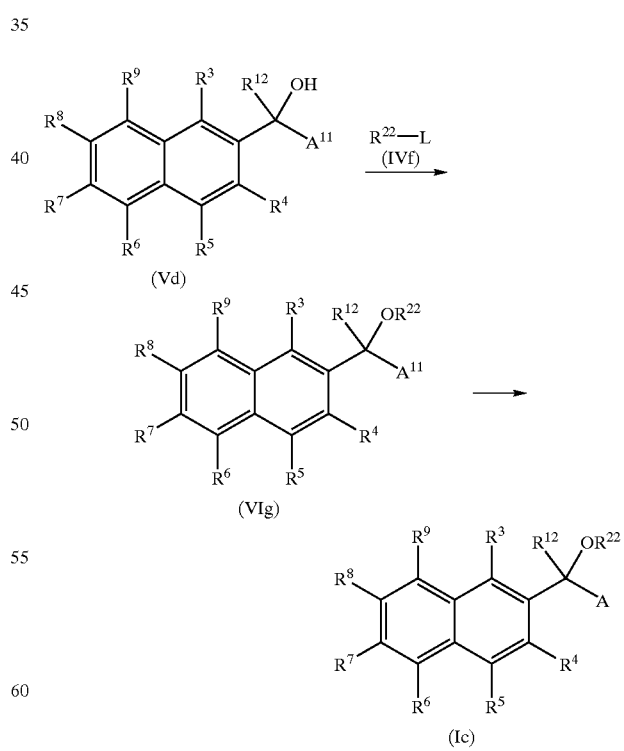

[wherein each symbol has the same meaning as defined above.]

Compound (Ic) can be produced by subjecting Compound (Vd) to alkylation reaction by using Compound (IVf) to give Compound (VIg), followed by removing the protecting group. The alkylation reaction is carried out by a similar manner to the production of Compound (IVd) from Compound (IVc2). The elimination of the protecting group is carried out by a similar manner to the production of Compound (Ia) from Compound (IVd).

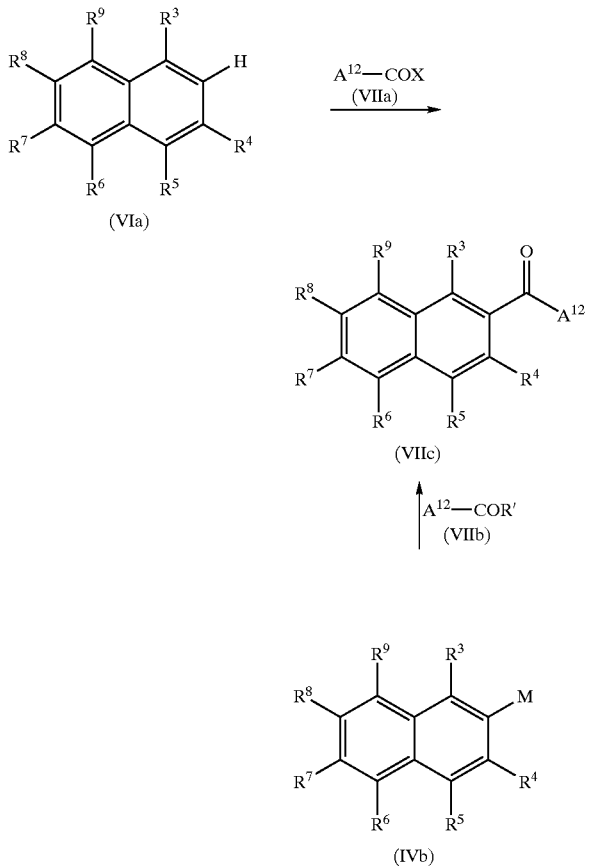

(wherein each symbol has the same meaning as defined above.)

Compound (VIa) is reacted with (VIIa) by a known Friedel-Crafts reaction, the manner shown in Shin-jikkenkagaku-koza Vol. 14, p511 (Maruzen co. Japan) or a manner similar to those manner, to give a carbonyl compound (VIIc). Compound (VIIc) can also be produced by reacting Compound (IVb) with Compound (VIIb). The reaction is carried out in an inert solvent such as THF, dichloromethane, etc. Compound (IVb) is used in an amount of 0.2 to 2 equivalents, preferably 0.2 to 1.5 equivalents to Compound (VIIb). The reaction temperature is usually −80° C. to 50° C., preferably −80° C. to 20° C.

When the desired compound is obtained in free form, the compound may be converted to a salt by a conventional manner. When the desired compound is obtained in a salt, the compound can be converted to free form by a conventional manner. Compound (I) thus obtained can be isolated from the reaction mixture and purified by a known procedure such as phase transfer, concentration, solvent extraction, fractional distillation, crystallization, recrystallization, chromatography, etc. In the above reactions, an amino group, a carboxyl group, a hydroxy group, each of which is not involved in the reaction, in the compound or a salt thereof which is to be reacted may be protected. The protection with a protecting group and deprotection can be carried out by a known manner. Examples of the protecting group of an amino group include, for example, formyl, a $C_{1-6}$alkylcarbonyl (for example, acetyl, propionyl, etc.), a phenyl carbonyl, a $C_{1-6}$alkyl-oxycarbonyl (for example, methoxycarbonyl, ethoxycarbonyl, etc.), phenyloxycarbonyl, a $C_{7-10}$aralkyloxy-carbonyl (for example, a phenyl-$C_{1-4}$alkyloxy-carbonyl such as benzyloxycarbonyl, etc.), trityl, phthaloyl or N,N-dimethylaminomethylene, etc., each of which may be substituted. Examples of the substituent include a halogen atom (for example, fluorine, chlorine, bromine, iodine, etc.), formyl, a $C_{1-6}$alkyl-carbonyl (for example, acetyl, propionyl, valeryl, etc.), nitro, etc. The number of substituent is about 1 to 3.

Examples of the protecting group of a carboxyl group include, for example, a $C_{1-6}$alkyl (for example, methyl, ethyl, propyl, isopropyl, butyl, tert-butyl, etc.), phenyl, trityl or silyl, etc., each of which may be substituted. Examples of the substituent include, a halogen atom (for example, fluorine, chlorine, bromine, iodine, etc.), formyl, a $C_{1-6}$alkyl-carbonyl(for example, acetyl, propionyl, valeryl, etc.), nitro, etc. The number of substituent is about 1 to 3.

Examples of the protecting group of a hydroxy group include, for example, a $C_{1-6}$alkyl (for example, methyl, ethyl, propyl, isopropyl, butyl, tert-butyl, etc.), phenyl, a $C_{7-10}$aralkyl (for example, a phenyl-$C_{1-4}$alkyl such as benzyl, etc.), formyl, a $C_{1-6}$alkyl-carbonyl (for example, acetyl, propionyl, etc.), phenyloxycarbonyl, benzoyl, a ($C_{7-10}$aralkyloxy)carbonyl (for example, a phenyl-$C_{1-4}$alkyloxy-carbonyl such as benzyloxycarbonyl, etc.), pyranyl, furanyl or silyl, etc., each of which may be substituted. Examples of the substituent include a halogen atom (for example, fluorine, chlorine, bromine, iodine, etc.), a $C_{1-6}$alkyl (for example, methyl, ethyl, propyl, etc.), phenyl, a $C_{7-10}$aralkyl (for example, a phenyl-$C_{1-4}$alkyl such as benzyl, etc.), nitro, etc. The number of substituent is about 1 to 4.

The deprotection reaction is carried out by a known manner or a similar manner thereof. Examples of the deprotection reaction include a manner treating with, for example, acid, base, reduction, ultraviolet ray, hydrazine, phenyl hydrazine, sodium N-methyldithiocarbamate, tetrabutylammonium fluoride, palladium acetate, etc.

When Compound (I) is diastereomer, conformer, etc., Compound (I) can be isolated and purified by a isolation procedure or purification procedure mentioned above, if desirable. When Compound (I) is a racemate, (+)-form and (−)-form of Compound (I) can be isolated by a usual optical resolution procedure. When Compound (I) has a basic group, it can be converted to a salt with acid by a known manner.

Compound (I) has superior effect for medicine, and especially has a superior inhibitory activity of steroid $C_{17,20}$-lyase. Compound (I) is less toxic and has little adverse side effect. Compound (I) is useful for the preventing and treating a mammal (for example, humans, bovines, horses, dogs, cats, monkeys, mice, rats, etc., especially humans) suffering from various disease such as (1) primary cancer of malignant tumor (for example, prostate cancer, breast cancer, uterine cancer, ovarian cancer, etc.), and its metastasis and recurrence, (2) various symptoms accompanied with these cancer (for example, pain, cachexia, etc.), (3) prostatichypertrophy, virilism, hirsutism, male pattern alopecia, precocious puberty, endometriosis, uterus myoma, adenomyosis of uterus, mastopathy, polycystic ovary syndrome, etc.

While Compound (I) has a superior effect when used solely, the effect can be promoted by using the compound (I)

in combination with other medicaments and remedies. Examples of the medicament and remedy, include, for example, sex hormones, alkylating agents, antimetabolites, antitumor antibiotics, plant alkaloids, immunotherapies, etc., but not limited to.

Examples of the hormone like agent include, for example, Fosfestrol, Diethylstilbestrol, chlorotrianisene, Medroxyprogesterone acetate, Megestrol acetate, Chlormadinone acetate, Cyproterone acetate, Danazol, Allylestrenol, Gestrinone, Mepartricin, Raloxifene, Ormeloxifene, Levormeloxifene, antiestrogens (for example, Tamoxifen, Toremifene, etc.), the contraceptive pill, Mepitiostane, Testolactone, Aminoglutethimide, LH-RH agonist (for example, Goserelin acetate, Buserelin, Leuprorelin, etc.), LH-RH antagonist (for example, Ganirelix, Cetrorelix, Abarelix, etc.), Droloxifene, Epitiostanol, Ethinylestradiol sulfonate, aromatase inhibitors(for example, Fadrozole, Anastrozole, Letrozole, Exemestane, Vorozole, Formestane, etc.), anti-androgens (for example, Flutamide, Bicalutamide, Nilutamide, etc.), 5α-reductase inhibitors (for example, Finasteride, Epristeride, etc.), adrenocortical hormones (for example, Dexamethasone, Prednisolone, Betamethasone, Triamcinclone, etc.), inhibitors of androgen-synthesis (for example, Abiraterone, etc.), Retinoid and suppressing agents of Retinoid metabolism (for example, Liarozole, etc.), etc.

Examples of the alkylating agents include, for example, Nitrogen mustard, Nitrogen mustard N-oxide hydrochloride, Chlorambucil, Cyclophosphamide, Ifosfamide, Thiotepa, Carboquone, Improsulphan tosilate, Busulfan, Nimustine, Mitobronitol, Melphalan, Dacarbazine, Ranimustine, Estramustine phosphate sodium, Triethylenemelamine, Carmustine, Lomustine, Streptozocin, Pipobroman, Ethoglucid, Carboplatin, Cisplatin, Miboplatin, Nedaplatin, Oxaliplatin, Altretamine, Ambamustine, Dibrospidium chloride, Fotemustine, Prednimustine, Pumitepa, Ribomustin, Temozolomide, Treosulfan, Trofosfamide, Zinostatin stimalamer, Carboquone, Adozelesin, Cystemustine, Bizelesin, etc.

Examples of the antimetabolites include, for example, Mercaptopurine, 6-Mercaptopurine riboside, Thioinosine, Methotrexate, Enocitabine, Cytarabine, Cytarabine ocfosfate, Ancitabine hydrochloride, 5-FU analogues (for example, Fluorouracil, Tegafur, UFT, Doxifluridine, Carmofur, Galocitabine, Emitefur, etc.), Aminopterin, Leucovorin calcium, Tabloid, Butocin, Calcium folinate, Calcium levofolinate, Cladribine, Emitefur, Fludarabine, Gemcitabine, Hydroxycarbamide, Pentostatin, Piritrexim, Idoxuridine, Mitoguazone, Tiazofurin, Ambamustine, etc.

Example of antitumor antibiotics include, for example, Actinomycin D, Actinomycin C, Mitomycin C, Chromomycin A3, Bleomycin hydrochloride, Bleomycin sulfate, Peplomycin sulfate, Daunorubicin hydrochloride, Doxorubicin hydrochloride, Aclarubicin hydrochloride, Pirarubicin hydrochloride, Epirubicin hydrochloride, Neocarzinostatin, Mithramycin, Sarkomycin, Carzinophilin, Mitotane, Zorubicin hydrochloride, Mitoxantrone hydrochloride, Idarubicin hydrochloride, etc.

Examples of the plant alkaloid include, for example, Etoposide, Etoposide Phosphate, Vinblastine sulfate, Vincristine sulfate, Vindesine sulfate, Teniposide, Paclitaxel, Vinorelbine, etc.

Examples of the immunotherapy (BRM) include, for example, Picibanil, Krestin, Sizofiran, Lentinan, Ubenimex, Interferons, Interleukins, Macrophage-colony stimulating factor, granules stimulating factor of spheroid colony, Erythropoietin, Lymphotoxin, BCG vaccine, Corynebacterium parvum, Levamisole, Polysaccharide-K, Procodazol, etc.

Others: L-asparaginase, Aceglatone, Procarbazine hydrochloride, Protoporphyrin, Hematoporphyrin, topoisomerase Iinhibitors (for example, Irinotecan, Topotecan, etc.), topoisomerase Iiinhibitors (for example, Sobuzoxane, etc.), differentiation promoter (for example, Retinoid, Vitamin D, etc.), inhibitor of proliferation factor (for example, Suramin, etc.), Angiogenesis inhibitors, a-broker (for example, Tamsulosin hydrochloride, etc.), Tyrosin kinase inhibitors, etc.

Examples of the other remedies include operation, thermotherapy, radiotherapy, etc. Therapies other than chemotherapies, such as an operation including orchiectomy, thermotherapy, radiotherapy, etc., can be conducted together with the administration of Compound (I).

Examples of the pharmaceutically acceptable carrier include various organic or inorganic carriers which are used as pharmaceutical ingredients. Excipients, lubricants, binders, disintegrators, thickeners can be used for solid preparations; solvents, dispersants, solubilizing agents, suspending agents, isotonic agents, buffer agents, soothing agents, etc., can be used for liquid preparations. If necessary, additives such as preservatives, antioxidants, coloring agents, sweetening agents, etc., can be used. Examples of the preferable excipient include, for example, lactose, saccharose, D-mannitol, starch, crystalline cellulose, light anhydrous silicic acid, etc. Examples of the preferable lubricant include, for example, magnesium stearate, calcium stearate, talc, colloidal silica, etc. Examples of the preferable binder include, for example, crystalline cellulose, saccharose, D-mannitol, dextrin, hydroxypropylcellulose, hydroxypropylmethylcellulose, polyvinyl pyrrolidone, etc. Examples of the preferable disintegrator include, for example, starch, carboxymethylcellulose, carboxymethylcellulose calcium, crosscarmelose sodium, carboxymethyl starch sodium, etc. Examples of the preferable thickener include, for example, natural rubbers, cellulose derivatives, acrylic acid polymers, etc. Examples of the preferable solvent include, for example, water for injection, alcohol, propyleneglycol, Macrogol, sesame oil, corn oil, etc. Examples of the preferable dispersant include, for example, Tween 80, HCO 60, polyethylene glycol, carboxymethylcellulose, sodium alginate, etc. Examples of the preferable solubilizing agent include, for example, polyethylene glycol, propyleneglycol, D-mannitol, benzyl benzoate, ethanol, trisaminomethane, cholesterol, triethanolamine, sodium carbonate, sodium citrate, etc. Examples of the preferable suspending agent include, for example, surfactarits such as stearyl triethanolamine, sodium laurylsulfate, lauryl aminopropionic acid, lecithin, benzalkonium chloride, benzethonium chloride, glycerin monostearate, etc.; for example, hydrophilic polymer such as polyvinylalcohol, polyvinyl pyrrolidone, sodium carboxymethyl cellulose, methylcellulose, hydroxymethylcellulose, hydroxyethylcellulose, hydroxypropylcellulose, etc. Examples of the preferable isotonic agent include, for example, sodium chloride, glycerin, D-mannitol, etc. Examples of the preferable buffer agent include, for example, buffer solution such as phosphoric acid salt, acetic acid salt, carbonate, citric acid salt, etc. Examples of the preferable soothing agent include, for example, benzyl alcohol, etc. Examples of the preferable preservative include, for example, paraoxybenzoates, chlorobutanol, benzyl alcohol, phenethylalcohol, dehydroacetic acid, sorbic acid, etc. Examples of the preferable antioxidant include, for example, sulfurous acid salt, ascorbic acid, etc.

The pharmaceutical preparation of the present invention can be manufactured by a usual manner. The ratio of Compound (I) contained in a pharmaceutical preparation is usually 0.1 to 100% (w/w). Examples of the embodiment of the pharmaceutical preparation are as follows:

(1) tablets, powder, granules, capsules:

These preparations can be prepared by adding, for example, exipients, disintegrators, binders or lubricants, etc., to Compound (I), by compressive molding the mixture and if necessary, by coating for masking of taste, enteric or sustained release.

(2) injections:

These preparations can be prepared by dissolving Compound (I) in aqueous injection together with, for example, dispersants, preservatives, isotonic agents, etc., or by dissolving, dispersing or emulsifying Compound (I) in a vegetable oil such as olive oil, sesame oil, cotton seed oil, corn oil, etc., or propyleneglycol, etc., to give an oily injection.

(3) suppositories:

These preparations can be produced by preparing a liquid composition containing Compound (I), which may be oily, aqueous solid like or aqueous semisolid like. Examples of the oily base used for the composition include, for example, triglycerin ester of long-chain fatty acid (for example, cacao butter, witepsols, etc.), middle-chain fatty acid (for example, miglyols, etc.), vegetable oils (for example, sesame oil, soybean oil, cotton seed oil, etc.), etc. Examples of the aqueous gel base include, for example, natural rubber, cellulose derivative, vinyl polymer, acrylic acid polymer, etc.

The content of Compound (I) in these preparation is usually 0.01 to 50%, though it varies depending upon the kind of pharmaceutical preparation.

The rate of the compound of the present invention in the above pharmaceutical preparation, varies depending upon the compound used, kind of animal to which the compound is administered, number of administration times, etc. The daily dose of the compound of the present invention, for example, for adult humans suffering from solid tumors (a patient suffering from, for example, prostate cancer), is usually about 0.001 to about 500 mg/kg-weight, preferably about 0.1 to about 40 mg/kg-weight, more preferably about 0.5 to about 20 mg/kg-weight. When Compound (I) is non-orally administered or when it is administered in combination with an other anti-cancer agent, Compound (I) is administered in a less amount mentioned above. A dose of Compound (I) actually a administered are decided by a doctor by taking kind of compound, type of pharmaceutical preparation, age of the patient, body weight, sex, degree of disease, administration route, administration term and its interval, etc., into consideration, and the dose may be changed by a doctor.

The pharmaceutical preparation can be administered orally or parenterally. Examples of the parenteral administration route include intravenous, intramuscular, subcutaneous, intranasal, intradermal, instillation, intracerebral, intrarectal, intravaginal and intraperitoneal, etc.

The above mentioned administration term and administration interval varies depending upon the various conditions and decided by a doctor. As the administration, there may be mentioned divided administration, daily administration, intermittent administration, high dose administration therapy in short term, repeat administration, etc. It is preferable to administer the compound, for example, once to some times a day (especially two or three times a day). It is possible to administer the compound once to some times a day when oral administration. It is also possible to the compound as a sustained release preparation. It is also possible to the compound by intravenous drip infusion over a long time

BEST MODE FOR CARRYING OUT THE INVENTION

The present invention is hereinafter described in more detail by means of the following Examples, pharmaceutical preparations and Experimental Examples, but these are merely described as examples and they are not intended to limit the present invention. The meanings of the following abbreviated symbols are as follows.

s: singlet, d: doublet, t: triplet, q: quartet, dd: double doublet, dt: double triplet, m: multiplet, br: broad, J: coupling constant, room temperature: 0~30° C., DMF: dimethylformamide, THF: tetrahydrofuran.

EXAMPLE 1

Production of 1-(1H-Imidazol-4-yl)-1-(6-methoxynaphthalen-2-yl)-2-methyl-1-propanol (i) Production of (6-Methoxynaphthalen-2-yl)-(1-trityl-1H-imidazol-4-yl)methanol 2-Bromo-6-methoxynaphthalene (30 g) was dissolved in THF (400 ml), and the solution was cooled at −78° C. To the solution was added dropwise a solution of n-butyllithium in hexane (1.6 M; 99 ml), and the mixture was stirred at −78° C. for 30 min. To the mixture was slowly added dropwise a solution of 4-fotmyl-1-trityl-1H-imidazole (38.9 g) in THF (300 ml), and the mixture was stirred at −78° C. for 30 min. The reaction mixture was poured into a 3% aqueous solution of citric acid (600 ml) and partitioned. The organic layer was separated, and the aqueous layer was extracted with ethyl acetate. The organic layers were combined, washed with saturated aqueous solution of sodium chloride, dried and concentrated. The residue was washed with ethyl acetate to give the titled compound as a colorless solid (35.0 g).

$^1$H-NMR (CDCl$_3$) δ: 3.90 (3H, s), 5.89 (1H, s), 6.60 (1H, d, J=1.4 Hz), 7.08–7.15 (8H, m), 7.26–7.34 (9H, m), 7.42–7.47 (2H, m), 7.63–7.69 (2H, m), 7.78 (1H, s); IR (KBr): 3166, 1603, 1478, 1451, 1260, 1171, 1128, 754, 702 cm$^{-1}$.

(ii) Production of (6-Methoxynaphthalen-2-yl)-(1-trityl-1H-imidazol-4-yl)ketone (6-methoxynaphthalen-2-yl)-(1-trityl-1H-imidazol-4-yl) methanol (18.0 g) was dissolved in chloroform (300 ml), and to the solution was added manganese dioxide (56 g). The mixture was heated for 1 h under reflux. The reaction mixture was filtered and concentrated. Crystallization of the residue from ether gave the titled compound (17.0 g) as a colorless solid.

$^1$H-NMR (CDCl$_3$) δ: 3.94 (3H, s), 7.15–7.23 (8H, m) 7.34–7.40 (9H, m), 7.58 (1H, d, J=1.3 Hz), 7.78 (1H, d, J=1.3 Hz), 7.78 (1H, d, J=8.6 Hz), 7.86 (1H, d, J=9.6 Hz), 8.26 (1H, dd, J=8.6, 1.6 Hz), 8.95 (1H, s); IR (KBr): 1620, 1520, 1493, 1480, 1445, 1265, 1196, 1179, 909, 872, 747, 733, 702 cm$^{-1}$.

(iii) Production of (1H-Imidazol-4-yl)-(6-methoxynaphthalen-2-yl)ketone (6-Methoxynaphthalen-2-yl)-(1-trityl-1H-imidazol-4-yl) ketone (15.0 g) was dissolved in THF (80 ml). To the solution was added 90% formic acid (20 ml), and the mixture was stirred at 50° C. for 2 h. After removal of the solvents by evaporation, 1N-hydrochloric acid (60 ml) was added and the precipitate was filtered off. The filtrate was washed with ether, and neutralized with potassium carbonate. The resulting precipitate was collected by filtration, dried under reduced pressure to give the titled compound (7.54 g) as a colorless solid.

$^1$H-NMR (CDCl$_3$+CD$_3$OD) δ: 3.97 (3H, s), 7.26–7.21 (2H, m), 7.78 (1H, s), 7.82–7.91 (3H, m), 7.99 (1H, dd, J=8.5, 1.7 Hz), 8.49 (1H, s); IR (KBr): 1636, 1624, 1481, 1346, 1264, 1169, 1024, 1005 cm$^{-1}$.

(iv) Production of 1-(1H-Imidazol-4-yl)-1-(6-methoxynaphthalen-2-yl)-2-methyl-1-propanol (1H-Imidazol-4-yl)-(6-methoxynaphthalen-2-yl)ketone (6.50 g) was dissolved in THF (120 ml), and the solution was cooled to −10° C. To the solution was slowly added dropwise a solution of isopropyl magnesium chloride in THF (2.0 M; 38.7 ml), and the mixture was stirred at −10° C. for 30 min. To the reaction mixture was added saturated aqueous solution of ammonium chloride and water. The mixture was extracted with ethyl acetate. The extract was washed with saturated aqueous solution of sodium chloride, dried and concentrated. The residue was purified by silica gel column chromatography (eluent, chloroform:methanol= 20:1→10:1). Recrystallization from ethyl acetate gave the titled compound (5.04 g) as a colorless crystalline powder.

$^1$H-NMR (CDCl$_3$+CD$_3$OD) δ: 0.81 (3H, d, J=6.8 Hz), 1.00 (3H, d, J=6.8 Hz), 2.64–2.78 (1H, m), 3.91 (3H, s), 7.00 (1H, d, J=1.0 Hz), 7.09–7.15 (2H, m), 7.51–7.56 (2H, m), 7.65–7.75 (2H, m), 7.91 (1H, d, J=1.4 Hz); IR (KBr): 3140, 2984, 2957, 1464, 1222, 1028, 856, 806, 652 cm$^{-1}$.

EXAMPLE 2

Production of 1-(1H-Imidazol-4-yl)-1-(6-methoxynaphthalen-2-yl)ethanol (i) Production of 1-(6-Methoxynaphthalen-2-yl)-1-(1-trityl-1H-imidazol-4-yl)ethanol (6-Methoxynaphthalen-2-yl)-(1-trityl-1H-imidazol-4-yl) ketone (2.50 g) was dissolved in THF (20 ml), and the solution was cooled to 0° C. To the solution was slowly added dropwise a solution of methylmagnesium bromide in ether (3.0M, 3.4 ml), and the mixture was stirred for 20 min at 0° C. To the reaction mixture was added saturated aqueous solution of ammonium chloride and water. The mixture was extracted with ethyl acetate. The extract was washed with saturated aqueous solution of sodium chloride, dried and concentrated to give the titled compound (2.51 g) as a colorless powder.

$^1$H-NMR (CDCl$_3$) δ: 1.85 (3H, s), 3.62 (1H, br-s), 3.90 (3H, s), 6.77 (1H, d, J=1.4 Hz), 7.09 (1H, s), 7.131–7.21 (7H, m), 7.30–7.36 (9H, m), 7.41 (1H, d, J=1.4 Hz), 7.45 (1H, dd, J=8.7 Hz, 1.8 Hz), 7.62–7.69 (2H, m), 7.80 (1H, d, J=1.6 Hz); IR (KBr): 3150, 1605, 1493, 1445, 1264, 1177, 1165, 909, 747, 733, 702 cm$^{-1}$.

(ii) Production of 1-(1H-Imidazol-4-yl)-1-(6-methoxynaphthalen-2-yl)ethanol 1-(6-Methoxynaphthalen-2-yl)-1-(1-trityl-1H-imidazol-4-yl)ethanol (2.20 g) was dissolved in 90% formic acid (15 ml), and the solution was stirred at room temperature for 15 h. To the solution was added 1 N-hydrochloric acid, and precipitate was filtered off. The filtrate was neutralized with potassium carbonate, and extracted with ethyl acetate. The extract was washed with saturated aqueous solution of sodium chloride, dried and concentrated. The residue was purified by silica gel column chromatography (eluent, ethyl acetate:methanol=20:1 chloroform:methanol=10:1) to give the titled compound (1.05 g) as a colorless solid.

$^1$H-NMR (CDCl$_3$+CD$_3$OD) δ: 1.94 (3H, s), 3.92 (3H, s), 6.88,(1H, s), 7.11–7.16 (2H, m), 7.46 (1H, dd, J=8.5, 1.9 Hz), 7.53 (1H, d, J=1.0 Hz), 7.67 (1H, d, J=3.4 Hz), 7.72 (1H, d, J=5.2 Hz), 7.82 (1H, d, J=1.2 Hz); IR (KBr): 3160, 1607, 1485, 1453, 1264, 1171, 1115, 893, 847 cm$^{-1}$.

EXAMPLE 3

Production of 1-(1H-Imidazol-4-yl)-1-(6-methoxynaphthalen-2-yl)-2,2,2-trifluoroethanol (6-Methoxynaphthalen-2-yl)-(1-trityl-1H-imidazol-4-yl) ketone (1.0 g) was dissolved in THF (10 ml) and to the solution was added trifluoromethyltrimethylsilane (1.40 g). The reaction mixture was cooled to 0° C., and tetrabutylammonium fluoride (0.4 ml) was added. The mixture was stirred at room temperature for 2 h. To the mixture were added 1 N-hydrochloric acid (10 ml) and isopropanol (5 ml), and the mixture was stirred at room temperature for 24 h. The reaction mixture was neutralized, and extracted with ethyl acetate. The extract was washed with saturated aqueous solution of sodium chloride, dried and concentrated. The residue was purified by silica gel column chromatography (eluent, chloroform methanol=20:1→10:1). Recrystallization from ethyl acetate gave the titled compound (0.40 g) as a colorless powder.

$^1$H-NMR (CDCl$_3$+CD$_3$OD) δ: d 3.92 (3H, s), 7.10–7.18 (3H, m) 7.59 (1H, d, J=1.0 Hz), 7.63 (1H, s), 7.71 (1H, d, J=3.6 Hz), 7.76 (1H, d, J=4.2 Hz), 8.02 (1H, s); IR (KBr): 3000, 1487, 1395, 1265, 1165, 899, 889, 858 cm$^{-1}$.

EXAMPLE 4

Production of Cyclopropyl-(6-methoxynaphthalen-2-yl)-(1H-imidazol-4-yl)methanol Fumarate (1H-Imidazol-4-yl)-(6-methoxynaphthalen-2-yl)ketone (0.97 g) was dissolved in THF (20 ml), and the solution was cooled to 0° C. To the solution was slowly added dropwise a solution of cyclopropylmagnesium bromide in THF (1.7 M; 8 ml), and the mixture was stirred for 30 min at 0° C. To the reaction mixture was added saturated aqueous solution of ammonium chloride. The mixture was diluted with water, and neutralized with 1 N-hydrochloric acid. The dilution was extracted with ethyl acetate, washed with saturated aqueous solution of sodium chloride, dried and concentrated. The residue was purified by silica gel column chromatography (eluent, chloroform:methanol=20:1). To the obtained compound (0.53 g) was added fumaric acid (0.21 g). Recrystallization from methanol gave the titled compound (0.50 g) as a colorless solid.

$^1$H-NMR (DMSO-d$_6$) δ: 0.32–0.62 (4H, m), 1.62–1.76 (1H, m), 2.49–2.52 (1H, m), 6.61 (2H, s), 3.86 (3H, s), 7.04 (1H, d, J=1.2 Hz), 7.12 (1H, dd, J=8.8, 2.4 Hz), 7.25 (1H, d, J=2.4 Hz), 7.52 (1H, dd, J=8.7, 1.7 Hz), 7.65–7.79 (3H, m), 7.89 (1H, s); IR (KBr): 1609, 1265, 1227, 1179, 1163, 1063, 851 cm$^{-1}$.

EXAMPLE 5

Production of 2,2-Dimethyl-1-(1H-Imidazol-4-yl)-1-(6-methoxynaphthalen-2-yl)-1-propanol Fumarate In a similar manner to that described in Example 4, the reaction and purification were carried out by using (1H-imidazol-4-yl)-(6-methoxynaphthalen-2-yl)ketone (0.80 g) and a solution of tert-butylmagnesium chloride in THF (2.0 M, 4.8 ml), whereby the titled compound (0.47 g) was obtained as a pale yellow solid.

$^1$H-NMR (CD$_3$OD) δ: 1.06 (9H, s), 3.89 (3H, s), 6.71 (2H, s), 7.62 (1H, dd, J=8.8, 2.0 Hz), 7.69–7.70 (2H, ,m), 7.80(1H, d, J=1.2 Hz), 7.93 (1H, s), 8.50 (1H, s); IR (KBr): 1535, 1391, 1271, 1215, 1167, 899, 851 cm$^{-1}$.

EXAMPLE 6

Production of (1H-Imidazol-4-yl)-(6-methoxynaphthalen-2-yl)-(pyridin-3-yl)methanol (i) Production of (6-Methoxynaphthalen-2-yl)-(pyridin-3-yl)-(1-trityl-1H-imidazol-4-yl)methanol 3-Bromopyridine (0.92 ml) was dissolved in ether (20 ml), and the solution was cooled at −78° C. To the solution was slowly added dropwise a solution of n-butyllithium in hexane (1.6 M 5.9 ml), the mixture was stirred for 20 min at −78° C. To the reaction mixture was slowly added a solution of (6-methoxynaphthalen-2-yl)-(1-trityl-1H-imidazol-4-yl)ketone (1.0 g) in THF (8 ml), and the mixture was stirred for 30 min at −78° C. To the reaction mixture was added water, and mixture was diluted with 2% citric acid (50 ml). The dilution was extracted with ethyl acetate, washed with saturated aqueous solution of sodium chloride, dried and concentrated. The residue was recrystallized from a mixed solution of ethyl acetate and diethyl ether to give the titled compound (0.98 g) as a pale yellow powder.

$^1$H-NMR (CDCl$_3$) δ: 3.90 (3H, s), 6.40 (1H, d, J=1.4 Hz), 7.09–7.23 (9H, m), 7.27–7.41 (10H, m), 7.50 (1H, d, J=1.6 Hz), 7.57–7.65 (3H, m), 7.70–7.76 (1H, m), 8.47 (1H, dd, J=4.8, 1.6 Hz), 8.54 (1H, d, J=2.2 Hz); IR (KBr): 3216, 1609, 1485, 1443, 1389, 1269, 1171, 1067, 1028, 878, 849, 748, 702 cm$^{-1}$.

(ii) Production of (1H-Imidazol-4-yl)-(6-methoxynaphthalen-2-yl)-(pyridin-3-yl)methanol (6-Methoxynaphthalen-2-yl)-(pyridin-3-yl)-(1-trityl-1H-imidazol-4-yl)methanol (0.80 g) was dissolved in 90% solution of formic acid (3 ml), and the solution was stirred at 50° C. for 30 min. To the solution was added 1 N-hydrochloric acid, and precipitate was filtered off. The filtrate was washed with ether, and neutralized with potassium carbonate. The filtrate was extracted with chloroform and concentrated. The residue was purified by silica gel column chromatography (eluent, chloroform:methanol=5:1). Recrystallization from THF gave the titled compound (0.36 g) as a colorless powder.

$^1$H-NMR (CDCl$_3$+CD$_3$OD) δ: 3.92 (3H, s), 6.44 (1H, s), 7.12–7.16 (2H, m), 7.25–7.29 (1H, m), 7.43 (1H, dd, J=8.5, 1.7 Hz), 7.64–7.71 (4H, m), 7.80 (1H, dd, J=8.0, 1.6 Hz), 8.44 (1H, dd, J=3.4, 1.2 Hz), 8.54 (1H, d, J=2.4 Hz); IR (KBr): 3058, 2840, 1422, 1265, 1167, 1152, 1034, 891, 851, 806 cm$^{-1}$.

EXAMPLE 7

Production of (1H-Imidazol-4-yl)-(6-methoxynaphthalen-2-yl)-(pyridin-4-yl)methanol (i) Production of (6-Methoxynaphthalen-2-yl)-(pyridin-4-yl)-(1-trityl-1H-imidazol-4-yl)methanol In a similar manner to that described in Example 6-(i), the reaction of 4-bromopyridine (0.92 ml) with (6-methoxynaphthalen-2-yl)-(1-trityl-1H-imidazol-4-yl) ketone (1.0 g) was carried out to give the titled compound (0.88 g) as a colorless solid.

$^1$H-NMR (DMSO-d$_6$) δ: 3.85 (3H, s), 6.49 (1H, s), 6.83 (1H, d, J=1.4 Hz), 7.11–7.15 (7H, m), 7.25 (1H, d, J=1.4 Hz), 7.37–7.43 (13H, m), 7.67–7.74 (3H, m), 8.44–8.47 (2H, m); IR (KBr): 1605, 1483, 1447, 1265, 1223, 1169, 1130, 1063, 1036, 762, 748, 702 cm$^{-1}$.

(ii) Production of (1H-Imidazol-4-yl)-(6-methoxynaphthalen-2-yl)-(pyridin-4-yl)methanol In a similar manner to that described in Example 6-(ii), a reaction and purification were carried out by using (6-methoxynaphthalen-2-yl)-(pyridin-4-yl)-(1-trityl-1H-imidazol-4-yl)methanol (0.70 g) to give the titled compound (0.36 g) as a colorless solid.

$^1$H-NMR (CDCl$_3$+CD$_3$OD) δ: 3.92 (3H, s), 6.50 (1H, d, J=1.4 Hz), 7.10–7.16 (2H, m), 7.39–7.44 (3H, m), 7.64–7.72 (4H, m), 8.47 (2H, dd, J=4.6, 1.6 Hz); IR (KBr): 3067, 2840, 1601, 1414, 1265, 1167, 893, 866, 853 cm$^{-1}$.

EXAMPLE 8

Production of 1-(1H-Imidazol-4-yl)-1-(6-methoxynaphthalen-2-yl)-1-phenylmethanol (i) Production of 1-(6-Methoxynaphthalen-2-yl)-1-phenyl-1-(1-trityl-1H-imidazol-4-yl)methanol In a similar manner to that described in Example 6-(i), the reaction of bromo benzene (0.85 ml) with (6-methoxynaphthalen-2-yl)-(1-trityl-1H-imidazol-4-yl) ketone (1.0 g) was carried out. The reaction mixture was purified by silica gel column chromatography (eluent, hexane:ethyl acetate=3:1→2:1) to give the titled compound (0.98 g) as a pale yellow powder.

$^1$H-NMR (CDCl$_3$) δ: 3.89 (3H, s), 6.40 (1H, d, J=1.4 Hz), 7.07–7.33 (22H, m), 7.41 (1H, dd, J=8.6, 1.6 Hz), 7.47 (1H, d, J=1.4 Hz), 7.58–7.63 (3H, m). IR (KBr): 3167, 1742, 1609, 1485, 1447, 1265, 1165, 1132, 1030, 889, 849, 756, 700 cm$^{-1}$.

(ii) Production of 1-(1H-Imidazol-4-yl)-1-(6-methoxynaphthalen-2-yl)-1-phenylmethanol In a similar manner to that described in Example 6-(ii), a reaction and purification were carried out by using 1-(6-methoxynaphthalen-2-yl)-1-phenyl-1-(1-trityl-1H-imidazol-4-yl)methanol (0.80 g) to give the titled compound. (0.31 g) as a colorless solid.

$^1$H-NMR (CDCl$_3$+CD$_3$OD) δ: 3.91, (3H, s) 6.41 (1H, s), 7.08–7.13 (2H, m), 7.25–7.39 (5H, m), 7.44 (1H, dd, J=8.7, 1.7 Hz), 7.59 (1H, d, J=1.2 Hz), 7.63–7.64 (2H, m), 7.68 (1H, d, J=2.6 Hz); IR (KBr): 3362, 2838, 1607, 1389, 1264, 1221, 1167, 1034, 862, 756 cm$^{-1}$.

EXAMPLE 9

Production of 1-(6-Methoxynaphthalen-2-yl)-2-methyl-1-(pyridin-4-yl)-1-propanol (i) Production of (6-Methoxynaphthalen-2-yl)(pyridin-4-yl)methanol In a similar manner to that described in Example 1-(i), the reaction of 2-bromo-6-methoxynaphthalene (15 g) with isonicotinic aldehyde (8.14 g) was carried out to give the titled compound (7.8 g) as a pale yellow solid.

$^1$H-NMR (CDCl$_3$) δ: 1.80 (1H, br s), 3.92 (3H, s), 5.93 (1H, s), 7.11 (1H, d, J=2.4 Hz), 7.16 (1H, dd, J=8.8, 2.6 Hz), 7.33–7.37 (3H, m), 7.70 (1H, s), 7.74 (2H, s), 8.51 (1H, d, J=1.4 Hz), 8.53 (1H, d, J=1.6 Hz); IR (KBr): 3133, 1634, 1603, 1507, 1483, 1416, 1391, 1265, 1219, 1167, 1030, 849, 818 cm$^{-1}$.

(ii) Production of (6-Methoxynaphthalen-2-yl)-(pyridin-4-yl)ketone

In a similar manner to that described in Example 1-(ii), a reaction and purification were carried out by using (6-methoxynaphthalen-2-yl)-(pyridin-4-yl)methanol (2.0 g) to give the titled compound (1.76 g) as a colorless solid.

$^1$H-NMR (CDCl$_3$) δ: 3.97 (3H, s), 7.20 (1H, s), 7.81 (1H, d, J=4.2 Hz), 7.24–7.27 (1H, m), 7.61 (1H, d, J=1.6 Hz), 7.64 (1H, d, J=1.6 Hz), 7.85 (1H, d, J=4.6 Hz), 7.93–7.98 (1H, m), 8.18 (1H, d, J=1.8 Hz), 8.83 (1H, d, J=1.2 Hz), 8.85 (1H, d, J=1.2 Hz); IR (KBr): 1651, 1622, 1483, 1466, 1406, 1287, 1265, 1219, 1024, 862, 828, 720 cm$^{-1}$.

(iii) Production of 1-(6-Methoxynaphthalen-2-yl)-2-methyl-1-(pyridin-4-yl)-1-propanol In a similar manner to that described in Example 1-(iv), the reaction of (6-methoxynaphthalen-2-yl)-(pyridin-4-yl)

ketone (0.6 g) was carried out to give the titled compound (0.34 g) as a colorless solid.

$^1$H-NMR (CDCl$_3$) δ: 0.90 (3H, d, J=6.8 Hz), 0.96 (3H, d, J=6.6 Hz), 2.30 (1H, br s), 3.05–2.91 (1H, m), 3.90 (3H, s), 7.08–7.17 (2H, m), 7.44–7.54 (3H, m), 7.66–7.75 (2H, m), 7.93 (1H, d, J=1.6 Hz), 8.49 (2H, d, J=6.2 Hz); IR (KBr): 3102, 1601, 1412, 1265, 1221, 1165, 1062, 853, 820, 810, 683 cm$^{-1}$.

EXAMPLE 10

Production of 1-(6-Methoxynaphthalen-2-yl)-2-methyl-1-(pyridin-3-yl)-1-propanol (i) Production of (6-Methoxynaphthalen-2-yl)-(pyridin-3-yl)methanol In a similar manner to that described in Example 1-(i), the reaction of 2-bromo-6-methoxynaphthalene (15.0 g) with nicotinic aldehyde (8.14 g) was carried out to give the titled compound (11.47 g) as a pale yellow solid.

$^1$H-NMR (CDCl$_3$) δ: 0.91 (3H, d, J=2.4 Hz), 0.95 (3H, d, J=2.4 Hz), 1.75 (1H, br-s), 3.92 (3H, s), 6.02 (1H, s), 7.12–7.30 (3H, m), 7.38 (1H, dd, J=8.5, 1.7 Hz), 7.70–7.79 (4H, m), 8.50 (1H, dd, J=4.9, 1.5 Hz), 8.67 (1H, d, J=2.0 Hz); IR (KBr): 3183, 1609, 1591, 1451, 1426, 1271, 1167, 1057, 1032, 909, 839, 818, 720 cm$^{-1}$.

(ii) Production of (6-Methoxynaphthalen-2-yl)-(pyridin-3-yl)ketone

In a similar manner to that described in Example 1-(ii), a reaction and purification were carried out by using (6-methoxynaphthalen-2-yl)-(pyridin-$^3$-yl)methanol (3.0 g) to give the titled compound (2.77 g) as a colorless solid.

$^1$H-NMR (CDCl$_3$) δ: 3.97 (3H, s), 7.21–7.26 (2H, m), 7.46–7.52 (1H, m), 7.81–7.93 (2H, m), 7.95 (1H, dd, J=8.5, 1.1 Hz), 8.14–8.21 (2H, m), 8.84 (1H, dd, J=4.8, 1.2 Hz), 9.05 (1H, d, J=2.0 Hz); IR (KBr): 1653, 1622, 1584, 1480, 1296, 1281, 1215, 1146, 1026, 895, 737 cm$^{-1}$.

(iii) Production of 1-(6-Methoxynaphthalen-2-yl)-2-methyl-1-(pyridin-3-yl)-1-propanol In a similar manner to that described in Example 1-(iv), a reaction was carried out by using (6-methoxynaphthalen-2-yl)-(pyridin-3-yl)ketone (0.65 g) to give the titled compound (0.34 g) as a pale yellow solid.

$^1$H-NMR (CDCl$_3$) δ: 0.91 (3H, d, J=2.4 Hz), 0.95 (3H, d, J=2.4 Hz), 2.90–3.04 (1H, m), 3.90 (3H, s), 7.08–7.22 (3H, m), 7.49 (1H, dd, J=8.5, 1.9 Hz), 7.65–7.75 (2H, m), 7.82–7.88 (1H, m), 7.93 (1H, d, J=1.8 Hz), 8.40 (1H, d, J=4.0 Hz), 8.77 (1H, s); IR (KBr): 3227, 2971, 1481, 1466, 1424, 1391, 1265, 1167, 1026, 878, 864, 802 cm$^{-1}$.

EXAMPLE 11

Production of 1-(5-Fluoro-6-methoxynaphthalen-2-yl)-1-(1H-imidazol-4-yl)-2-methyl-1-propanol In a similar manner to that described in Example 1-(iv), a reaction was carried out by using (5-fluoro-6-methoxynaphthalen-2-yl)-(1H-imidazol-4-yl)ketone (0.32 g) to give the titled compound (0.18 g) as a pale yellow solid.

$^1$H-NMR (CDCl$_3$+CD$_3$OD) δ: 0.80 (3H, d, J=6.8 Hz), 1.01 (3H, d, J=6.6 Hz), 2.63–2.76 (1H, m), 4.00 (3H, s), 6.70 (1H, d, J=1.2 Hz), 7.22–7.30 (1H, m), 7.51–7.65 (3H, m), 7.93–8.02 (2H, m); IR (KBr): 1495, 1383, 1362, 1281, 1098, 1053, 1019, 980, 797 cm$^{-1}$.

EXAMPLE 12

Production of 1-(1H-Imidazol-4-yl)-1-(6-methoxynaphthalen-2-yl)-1-propanol

In a similar manner to that described in Example 1-(iv), the reaction of (1H-imidazol-4-yl)-(6-methoxynaphthalen-2-yl)ketone (0.60 g) with a solution of ethyl magnesium bromide in ether (3.0 M, 2.4 ml) was carried out to give the titled compound (0.28 g) as a colorless solid.

$^1$H-NMR (CDCl$_3$+CD$_3$OD) δ: 0.87 (3H, t, J=7.3 Hz), 2.19–2.41 (2H, m), 3.92 (3H, s), 6.91 (1H, d, J=1.2 Hz), 7.11–7.16 (2H, m), 7.42 (1H, dd, J=8.8, 1.2 Hz), 7.54 (1H, d, J=1.2 Hz), 7.66–7.75 (2H, m), 7.86 (1H, d, J=1.4 Hz); IR (KBr): 3160, 2971, 1607, 1483, 1265, 1223, 1169, 1032 cm$^{-1}$.

EXAMPLE 13

Production of 1-(1H-Imidazol-4-yl)-1-(6-methoxynaphthalen-2-yl)-3-methyl-1-butanol In a similar manner to that described in Example 1-(iv), the reaction of (1H-imidazol-4-yl)-(6-methoxynaphthalen-2-yl)ketone (0.60 g) with absolution of isobutylmagnesium bromide in THF (1.0 M, 2.4 ml) was carried out to give the titled compound (0.14 g) as a colorless solid.

$^1$H-NMR (CDCl$_3$) δ: 0.72 (3H, d, J=6.8 Hz), 0.94 (3H, d, J=6.8 Hz), 1.63–1.82 (1H, m), 2.20 (2H, d, J=5.8 Hz), 3.90 (3H, s), 6.82 (1H, s), 7.10–7.14 (2H, m), 7.38 (1H, s), 7.42 (1H, dd, J=8.4, 1.8 Hz), 7.63–7.72 (2H, m), 7.93 (1H, d, J=1.4 Hz); IR (KBr): 2953, 1607, 1505, 1483, 1466, 1265, 1389, 1219, 1169, 1032, 853 cm$^{-1}$.

EXAMPLE 14

Production of 1-(1H-Imidazol-4-yl)-1-(6-methoxynaphthalen-2-yl)-1-butanol

In a similar manner to that described in Example 1-(iv), the reaction of (1H-imidazol-4-yl)-6-methoxynaphthalen-2-yl ketone (0.60 g) and n-propylmagnesium bromide in THF (1.0 M, 2.4 ml) to give the titled compound (0.53 g) as a colorless solid.

$^1$H-NMR (CDCl$_3$) δ: 0.89 (3H, t, J=7.3 Hz), 1.10–1.30 (1H, m), 1.37–1.55 (1H, m), 2.20–2.30 (2H, m), 3.91 (3H, s), 6.90 (1H, s), 7.10–7.15 (2H, m), 7.45 (1H, dd, J=8.6, 1.8 Hz), 7.50 (1H, s), 7.65–7.73 (2H, m), 7.91 (1H, s); IR (KBr): 2955, 1605, 1505, 1483, 1265, 1221, 1167, 1032, 850 cm$^{-1}$.

EXAMPLE 15

Production of 1-Cyclopentyl-1-(1H-imidazol-4-yl)-1-(6-methoxynaphthalen-2-yl)methanol In a similar manner to that described in Example 1-(iv), the reaction of (1H-imidazol-4-yl)-(6-methoxynaphthalen-2-yl)ketone (0.60 g) with cyclopentylmagnesium bromide in THF (1.0 M, 10 ml) was carried out to give the titled compound (0.80 g) as a colorless solid.

$^1$H-NMR (CDCl$_3$) δ: 1.34–1.72 (8H, m), 2.92–3.06 (1H, m), 3.90 (3H, s), 7.02 (1H, s), 7.09–7.14 (2H, m), 7.51–7.56 (2H, m), 7.63–7.74 (2H, m), 7.97 (1H, s); IR (KBr): 2959, 1607, 1483, 1265, 1221, 1169, 1032, 851 cm$^{-1}$.

EXAMPLE 16

Production of 1-(6-Acetoxynaphthalen-2-yl)-1-(1H-imidazol-4-yl)-2-methyl-1-propanol (i) Production of (6-Benzyloxynaphthalen-2-yl)-(1-trityl-1H-imidazol-4-yl)methanol In a similar manner to that described in Example 1-(i), a reaction was carried out by using 2-benzyloxy-6-bromonaphthalene (7 g) to give the titled compound as a colorless powder (5.5 g).

$^1$H-NMR (CDCl$_3$) δ: 5.17 (2H, s), 5.90 (1H, s), 6.65 (1H, s), 7.08–7.90 (27H, m); IR (KBr): 3061, 1633, 1604, 1483, 1446, 1390 cm$^{-1}$.

(ii) Production of (6-Benzyloxynaphthalen-2-yl)-(1-trityl-1H-imidazol-4-yl)ketone In a similar manner to that described in Example 1-(ii), a reaction was carried out by using (6-benzyloxynaphthalen-2-yl)-(1-trityl-1H-imidazol-4-yl)methanol (4.18 g) to give the titled compound (3.25 g) as a colorless powder.

$^1$H-NMR (CDCl$_3$) δ: 5.20 (2H, s), 7.10–7.92 (26H, m), 8.25 (1H, dd, J=8.8, 1.0 Hz); IR (KBr): 3061, 1620, 1521, 1180 cm$^{-1}$.

(iii) Production of 1-(6-Benzyloxynaphthalen-2-yl)-1-(1-trityl-1H-imidazol-4-yl)-2-methyl-1-propanol In a similar manner to that described in Example 1-(iv), a reaction was carried out by using (6-benzyloxynaphthalen-2-yl)-(1-trityl-1H-imidazol-4-yl)ketone (4.3 g) to give the titled compound (2.6 g) as a colorless powder.

$^1$H-NMR (CDCl$_3$) δ: 0.74 (3H, d, J=6.8 Hz), 0.94 (3H, d, J=6.8 Hz), 2.42–2.62 (1H, m), 3.67 (1H, s), 5.17 (2H, s), 6.80 (1H, d, J=1.4 Hz), 7.05–7.75 (26H, m), 7.94 (1H, s); IR (KBr): 3061, 2968, 1631, 1603, 1493, 1444, 1386 cm$^{-1}$.

(iv) Production of 1-(6-Hydroxynaphthalen-2-yl)-1-(1-trityl-1H-imidazol-4-yl)-2-methyl-1-propanol 1-(6-Benzyloxynaphthalen-2-yl)-1-(1-trityl-1H-imidazol-4-yl)-2-methyl-1-propanol (2.4 g) was dissolved in a mixed solution of THF and methanol (1:1, 160 ml). To the solution was added 10% palladium carbon (0.8 g). The mixture was stirred for 5 h under hydrogen atmosphere. The catalyst was filtered off, and filtrate was concentrated. The residue was crystallized from THF-ethyl acetate to give the titled compound (1.20 g) as a colorless powder.

$^1$H-NMR (CDCl$_3$) δ: 0.74 (3H, d, J=6.6 Hz), 0.95 (3H, d, J=6.6 Hz), 2.45–2.65 (1H, m), 6.80–7.86 (23H, m); IR (KBr): 3061, 2968, 1631, 1603, 1493, 1444, 1168 cm$^{-1}$.

(v) Production of 1-(6-Acetoxynaphthalen-2-yl)-1-(1-trityl-1H-imidazol-4-yl)-2-methyl-1-propanol A mixture of 1-(6-hydroxynaphthalen-2-yl)-1-(1-trityl-1H-imidazol-4-yl)-2-methyl-1-propanol (1.0 g), pyridine (4 ml) and anhydrous acetic acid (4 ml) was stirred at room temperature for 14 h. The reaction mixture was concentrated to dryness, and the residue was dissolved in ethyl acetate and washed with water and saturated aqueous solution of sodium chloride. The solution was dried and concentrated. The residue was crystallized from ethyl acetate-diisopropyl ether to give the titled compound (0.6 g) as a colorless powder.

$^1$H-NMR (CDCl$_3$) δ: 0.72 (3H, d, J=6.6 Hz), 0.96 (3H, d, J=6.6 Hz), 2.42–2.62 (1H, m), 6.80 (1H, d, J=1.2 Hz), 7.0–7.82 (21H, m), 8.02 (1H, s).

(vi) Production of 1-(6-Acetoxynaphthalen-2-yl)-1-(1H-imidazol-4-yl)-2-methyl-1-propanol 1-(6-Acetoxynaphthalen-2-yl)-1-(1-trityl-1H-imidazol-4-yl)-2-methyl-1-propanol (0.25 g) was dissolved in acetic acid (20 ml). To the mixture was added 10% palladium carbon (0.1 g). The mixture was stirred at 50° C. for 2 h under hydrogen atmosphere. The catalyst was filtered off, and filtrate was concentrated. The residue was purified by silica gel chromatography (eluent; dichloromethane-methanol=10:1) to give the titled compound (0.1 g) as a colorless solid.

$^1$H-NMR (CDCl$_3$) δ: 0.78 (3H, d, J=7 Hz), 1.00 (3H, d, J=7 Hz), 2.35 (3H, s), 2.59–2.79 (1H, m), 6.93 (1H, s), 7.18 (1H, dd, J=8.8, 2.6 Hz), 7.41 (1H, s), 7.49 (1H, d, J=2.6 Hz), 7.60 (1H, dd, J=8.8, 1.8 Hz), 7.71 (1H, d, J=8.4), 7.81 (1H, d, J=8.8 Hz), 8.04 (1H, s); IR (KBr): 3130, 2968, 1759, 1604, 1369, 1205 cm$^{-1}$.

EXAMPLE 17

Production of 1-(6-Hydroxynaphthalen-2-yl)-1-(1H-imidazol-4-yl)-2-methyl-1-propanol 1-(6-Benzyloxynaphthalen-2-yl)-1-(1-trityl-1H-imidazol-4-yl)-2-methyl-1-propanol (0.9 g) was dissolved in acetic acid (20 ml), and to the solution was added 10% palladium carbon (0.25 g). The mixture was stirred at 50° C. for 2 h under hydrogen atmosphere. The catalyst was filtered off, and the filtrate was concentrated. The residue was purified by silica gel chromatography (eluent; dichloromethane-methanol=10:1). Crystallization from methanol-ethyl acetate-diisopropyl ether gave the titled compound (0.30 g) as a colorless powder.

$^1$H-NMR (CDCl$_3$+CD$_3$OD) δ: 0.81 (3H, d, J=7 Hz), 1.00 (3H, d, J=7 Hz), 2.03 (1H, s), 2.60–2.80 (1H, m), 6.95–7.15 (3H, m), 7.40–7.72 (4H, m), 7.86 (1H, s).

EXAMPLE 18

Production of 1-(1-Acetoxymethyl-1H-imidazol-4-yl)-1-(6-methoxynaphthalen-2-yl)-2-methyl-1-propanol 1-(1H-Imidazol-4-yl)-1-(6-methoxynaphthalen-2-yl)-2-methyl-1-propanol (100 mg) was dissolved in THF (6 ml), and to the solution were added bromomethyl acetate (160 mg) and triethylamine (40 mg). The mixture was stirred at room temperature for 2 h. The reaction mixture was concentrated, and the residue was purified by silica gel chromatography (eluent, dichloromethane-methanol=20:1) to give the titled compound (30 mg) as a colorless solid.

$^1$H-NMR (CDCl$_3$+CD$_3$OD) δ: 0.79 (3H, d, J=7 Hz), 0.97 (3H, d, J=7 Hz), 2.07 (3H, s), 2.61–2.81 (1H, m), 3.40 (1H, br), 3.90 (3H, s), 5,76 (2H, s), 7.00–7.17 (3H, m), 7.55–7.78 (4H, m), 8.02 (1H, s).

EXAMPLE 19

Production of 4-[1-Methoxy-1-(6-methoxynaphthalen-2-yl)ethyl]-1H-imidazole (i) Production of 4-[1-Methoxy-1-(6-methoxynaphthalen-2-yl)ethyl]-1-trityl-1H-imidazole Sodium hydride (60% oil dispersion, 286 mg) was dispersed in THF (20 ml), and to the dispersion was added 1-(6-methoxynaphthalen-2-yl)-1-(1-trityl-1H-imidazol-4-yl)ethanol (3.05 g) under ice cooling. The mixture was stirred for 20 min, and methyl iodide (0.41 ml) was added. The mixture was stirred for 50 min under cooling. The reaction was quenched by the addition of water, and the reaction mixture was extracted with ethyl acetate, saturated aqueous solution of sodium chloride and concentrated. The residue was recrystallized from ether-hexane (1:1) to give the titled compound as a pale yellow powder (2.95 g).

$^1$H-NMR (CDCl$_3$) δ: 1.94 (3H, s), 3.18 (3H, s), 3.89 (3H, s), 6.77 (1H, d, J=1.4 Hz), 7.09–7.17 (8H, m), 7.30–7.33 (9H, m), 7.41–7.48 (2H, m), 7.63–7.72 (2H, m), 7.82 (1H, d, J=1.6 Hz). IR (KBr): 1603, 1483, 1445, 1264, 1188, 1148, 1111, 1026 cm$^{-1}$.

(ii) Production of 4-[1-Methoxy-1-(6-methoxynaphthalen-2-yl)ethyl]-1H-imidazole

4-[1-Methoxy-1-(6-methoxynaphthalen-2-yl)ethyl]-1-trityl-1H-imidazole (1.5 g) and pyridine hydrochloride (500 mg) were dissolved in methanol (8 ml). The solution was stirred at 60° C. for 2 h. After cooling, 1 N-hydrochloric acid was added to the solution, and precipitate was filtered off. The filtrate was washed with ether and neutralized with potassium carbonate. The filtrate was extracted with ethyl acetate, washed with saturated aqueous solution of sodium chloride, dried and concentrated. The residue was purified by silica gel column chromatography (eluent, ethyl acetate:methanol=30:1) to give the titled compound (0.33 g) as a colorless powder.

$^1$H-NMR (CDCl$_3$+CD$_3$OD) δ: 1.93 (3H, s), 3.21 (3H, s), 3.92 (3H, s), 6.93 (1H, d, J=1.2 Hz), 7.12–7.17 (2H, m), 7.43

(1H, dd, J=1.8, 8.6 Hz), 7.68 (1H, d, J=4.2 Hz), 7.73 (1H, d, J=4.8 Hz), 7.79 (1H, d, J=1.8 Hz). IR (KBr): 3002, 2957, 1607, 1483, 1460, 1273, 1208, 1103, 1026, 855 cm$^{-1}$.

EXAMPLE 20

Production of 1-(1H-Imidazol-4-yl)-1-(naphthalen-2-yl)-2-methyl-1-propanol (i) Production of (1H-Imidazol-4-yl)-(naphthalen-2-yl)ketone 4-Bromo-1H-imidazole (1.95 g) was dissolved in THF (30 ml), and the solution was cooled to −78° C. To the solution was added a solution of t-butyllithium in pentane (1.7 M; 20 ml). The mixture was stirred at 0° C. for 1.5 h. The mixture was again cooled to −78° C., and a solution of 2-formylnaphthalene (3.32 g) in THF (20 ml) was added. After the temperature was elevated from −78° C. to room temperature, the mixture was stirred at room temperature for 16 h. To the mixture was added an aqueous solution of ammonium chloride, and the mixture was extracted with ethyl acetate. The organic layer was dried and concentrated. The residue was purified by silica gel column chromatography,(eluent, dichloromethane:methanol=10:1). Recrystallization from dichloromethane-methanol gave the titled compound (1.00 g) as a colorless solid.

$^1$H-NMR (CDCl$_3$) δ: 7.53–7.70 (2H, m), 7.84–8.40 (6H, m), 8.53 (1H, s), 10.82 (1H, brs). IR (KBr): 2592, 1640, 1127, 779 cm$^{-1}$.

(ii) Production of 1-(1H-Imidazol-4-yl)-1-(naphthalen-2-yl)-2-methyl-1-propanol

In a similar manner to that described in Example i-(iv), a reaction was carried out by using (1H-imidazol-4-yl)-(naphthalen-2-yl)ketone (0.629 g) to give 1-(1H-imidazol-4-yl)-1-(naphthalen-2-yl)-2-methyl-1-propanol (0.338 g).

$^1$H-NMR (CDCl$_3$) δ: 0.79 (3H, d, J=6.8 Hz), 1.00 (3H, d, J=6.8 Hz), 2.69 (1H, m), 6.94 (1H, s), 7.34–7.48 (3H, m), 7.57 (1H, dd, J=1.8, 8.6 Hz), 7.50–7.84 (3H, m), 8.02 (1H, s). IR (KBr): 2969, 1470, 1128, 909, 816, 733 cm$^{-1}$.

EXAMPLE 21

Production of (−)-1-(1H-Imidazol-4-yl)-1-(6-methoxynaphthalen-2-yl)-2-methyl-1-propanol and (+)-1-(1H-Imidazol-4-yl)-1-(6-methoxynaphthalen-2-yl)-2-methyl-1-propanol 1-(1H-Imidazol-4-yl)-1-(6-methoxynaphthalen-2-yl)-2-methyl-1-propanol obtained in Example 1 was subjected to high performance liquid chromatography [column; CHIRALPAK AD (Produced by Daicel Chemical Co. Japan, 10 mm×250 mm), eluent; hexane-ethanol=7:3] to isolate optical antipode. (−)-Enantiomer was obtained from the first eluent and (+)-enantiomer was obtained from the second eluent.

EXAMPLE 22

Production of 4-[1-Methoxy-1-(6-methoxynaphthalen-2-yl)-2-methylpropyl]-1H-imidazole (i) Production of 1-(6-Methoxynaphthalen-2-yl)-2-methyl-1-(1-trityl-1H-imidazol-4-yl)-1-propanol In a similar manner to that described in Example 1-(iv), a reaction was carried out by using (6-methoxynaphthalen-2-yl)-(1-trityl-1H-imidazol-4-yl)ketone (4.0 g). Recrystallization from ether gave the titled compound (2.79 g) as a colorless powder.

$^1$H-NMR (CDCl$_3$+CD$_3$OD) δ: 0.74 (3H, d, J=6.8 Hz), 0.94 (3H, d, J=6.6 Hz), 1.90 (1H, br s), 2.46–2.59 (1H, m), 3.91 (3H, s), 6.80 (1H, d, J=1.4 Hz), 7.09–7.17 (8H, m), 7.29–7.37 (m, 10H), 7.53 (1H, dd, J=1.7, 8.7 Hz), 7.62–7.71 (2H, m), 7.93 (1H, d, J=1.2 Hz). IR (KBr): 1605, 1483, 1445, 1264, 1223, 1167, 909, 747 cm$^{-1}$.

(ii) Production of 4-[1-Methoxy-1-(6-methoxynaphthalen-2-yl)-2-methylpropyl]-1-trityl-1H-imidazole In a similar manner to that described in Example 19-(i), a reaction was carried out by using 1-(6-methoxynaphthalen-2-yl)-2-methyl-1-(1-trityl-1H-imidazol-4-yl)-1-propanol (2.8 g). The reaction mixture was purified by silica gel chromatography (hexane:ethyl acetate=2:1) to give the titled compound (2.68 g) as a pale yellow powder.

$^1$H-NMR (CDCl$_3$) δ: 0.79 (3H, d, J=6.4 Hz), 0.82 (3H, d, J=6.6 Hz), 2.90–3.03 (1H, m), 2.98 (3H, s), 3.90 (3H, s), 6.74 (1H, d, J=1.4 Hz), 7.09–7.23 (8H, m), 7.30–7.35 (9H, m), 7.47 (1H, dd, J=1.8, 8.6 Hz), 7.56 (1H, d, J=1.4 Hz), 7.62–7.6.7 (2H, m), 7.79 (1H, d, J=1.4 Hz). IR (KBr): 2961, 1605, 1481, 1447, 1264, 1169, 1074, 747, 702 cm$^{-1}$.

(iii) Production of 4-[1-Methoxy-1-(6-methoxynaphthalen-2-yl)-2-methylpropyl]-1H-imidazole 5

In a similar manner to that described in Example 19-(ii), a reaction was carried out by using 4-[1-methoxy-1-(6-methoxynaphthalen-2-yl)-2-methylpropyl]-1-trityl-1H-imidazole (2.0 g). Recrystallization from ethyl acetate gave the titled compound (0.90 g) as a colorless powder.

$^1$H-NMR (CDCl$_3$) δ: 0.84 (6H, d, J=6.6 Hz), 2.74–2.87 (1H, m), 2.97 (3H, s), 3.91 (3H, s), 7.08–7.16 (3H, m), 7.43 (1H, dd, J=1.8, 8.6 Hz), 7.60 (1H, s), 7.66–7.74 (2H, m), 7.79 (1H, s). IR (KBr): 3067, 2967, 1628, 1603, 1483, 1389, 1265, 1169, 1030, 1073, 849, 837, 820 cm$^{-1}$.

EXAMPLE 23

Production of 4-[Methoxy-(6-methoxynaphthalen-2-yl)methyl]-1H-imidazole (i) Production of 4-[Methoxy-(6-methoxynaphthalen-2-yl)methyl]-1-trityl-1H-imidazole Sodium hydride (60% oil dispersion, 1.77 g) was added to a mixture of THF (200 ml) and DMF(100 ml). To the mixture was added (6-methoxynaphthalen-2-yl)-(1-trityl-1H-imidazol-4-yl)methanol (20.0 g). The mixture was heated at 50 until the evolution of hydrogen ceased. The mixture was cooled to 0° C., and to the mixture was added methyl iodide (2.6 ml). The mixture was stirred for 15 min. Water was added to the reaction mixture to quench the reaction. THF was distilled off under reduced pressure. To the residue was added water, and the mixture was extracted with ethyl acetate. The extract was washed with water and saturated aqueous solution of sodium chloride, dried and concentrated. The residue was recrystallized from ethyl acetate-hexane to give the titled compound (18.6 g) as a colorless powder.

$^1$H-NMR (CDCl$_3$) δ: 3.36 (3H, s), 3.90 (3H, s), 5.39 (1H, s), 6.74 (1H, d, J=0.6 Hz), 7.09–7.15 (8H, m), 7.25–7.32 (9H, m), 7.38 (1H, d, J=1.4 Hz), 7.47 (1H, dd, J=1.7, 8.5 Hz), 7.67–7.73 (2H, m), 7.79 (1H, s). IR (KBr): 1605, 1483, 1445, 1260, 1233, 1211, 1190, 1091 cm$^{-1}$.

(ii) Production of 4-[Methoxy-(6-methoxynaphthalen-2-yl)methyl]-1H-imidazole

In a similar manner to that described in Example 19-(ii), a reaction was carried out by using 4-[Methoxy-(6-methoxynaphthalen-2-yl)methyl]-1-trityl-1H-imidazole (5.0 g). The crystals obtained was washed with water and ether and dried to give the titled compound (2.58 g) as a colorless powder.

$^1$H-NMR (CDCl$_3$+CD$_3$OD) δ: 3.41 (3H, s), 3.93 (3H, s), 5.44 (1H, s), 6.74 (1H, s), 7.13–7.17 (2H, m), 7.47 (1H, dd, J=1.5, 8.4 Hz), 7.57 (1H, s), 7.72 (1H, s), 7.76 (1H, s), 7.80 (1H, s). IR (KBr): 3085, 2996, 2826, 1605, 1485, 1460, 1235, 1177, 1086, 1076, 1028, 900, 781 cm$^{-1}$.

EXAMPLE 24

Production of 4-[Isopropoxy-(6-methoxynaphthalen-2-yl)methyl]-1H-imidazole (i) Production of 4-[Isopropoxy-(6-methoxynaphthalen-2-yl)methyl]-1-trityl-1H-imidazole (6-Methoxynaphthalen-2-yl)-(1-trityl-1H-imidazol-4-yl)methanol (12.5 g) was dissolved in pyridine (100 ml), and to the mixture was added benzoyl chloride (3.5 ml) under ice cooling. The mixture was stirred at room temperature for 3 h, and to the mixture was added saturated aqueous solution of hydrogen bicarbonate (150 ml). The resulting crystals were washed with water and ether to give a benzoate (15.3 g) as a colorless solid. The benzoate (1.6 g) was dissolved in a mixture of isopropanol (10 ml) and dioxane (10 ml), and the solution was stirred at 80° C. for 4 h. The solution was diluted with a saturated aqueous solution of hydrogen bicarbonate, extracted with dichloromethane, washed with a saturated aqueous solution of hydrogen bicarbonate and concentrated. The residue was recrystallized from THF-hexane to give the titled compound (1.1 g) as a colorless powder.

$^1$H-NMR (CDCl$_3$) δ: 1.18 (6H, d, J=6.2 Hz), 3.66–3.79 (1H, m), 3.90 (3H, s), 5.62 (1H, s), 6.74 (1H, d, J=1.4 Hz), 7.09–7.15 (8H, m), 7.26–7.32 (9H, m), 7.39 (1H, d, J=1.6 Hz), 7.49 (1H, dd, J=1.7, 8.5 Hz), 7.66–7.72 (2H, m), 7.75 (1H, s). IR (KBr): 1607, 1483, 1445, 1264, 1165, 1125, 1034, 747, 700 cm$^{-1}$.

(ii) Production of 4-[Isopropoxy-(6-methoxynaphthalen-2-yl)methyl]-1H-imidazole

In a similar manner to that described in Example 19-(ii), a reaction was carried out by using 4-[isopropoxy-(6-methoxynaphthalen-2-yl)methyl]-1-trityl-1H-imidazole (1.0 g) to give the titled compound (0.45 g) as a pale yellow powder.

$^1$H-NMR (CDCl$_3$) δ: 1.16 (3H, d, J=6.2 Hz), 1.21 (3H, d, J=6.0 Hz), 3.65–3.77 (1H, m), 3.90 (3H, s), 5.65 (1H, s), 6.73 (1H, s), 7.10–7.15 (2H, m), 7.44–7.49 (2H, m), 7.66 (1H, d, J=2.8 Hz), 7.70 (1H, s), 7.75 (1H, s). IR (KBr): 2970, 1609, 1483, 1265, 1169, 1123, 1034, 853 cm$^{-1}$.

EXAMPLE 25

Production of 1-(1H-Imidazol-4-yl)-1-(6-methoxynaphthalen-2-yl)-2-methyl-2-propen-1-ol In a similar manner to that described in Example 1-(iv), the reaction of (1H-imidazol-4-yl)-(6-methoxynaphthalen-2-yl)ketone (0.80 g) with 2-propen-2-ylmagnesium bromide in THF (1.0 M, 9.5 ml) was carried out to give the titled compound (0.76 g) as a colorless powder.

$^1$H-NMR (CDCl$_3$+CD$_3$OD) δ: 1.80 (3H, s), 3.94 (3H, s), 4.83 (1H, s), 5.14 (1H, s), 6.57 (1H, d, J=1.2 Hz), 7.11–7.19 (2H, m), 7.58 (1H, dd, J=2.0, 8.6 Hz), 7.64 (1H, d, J=1.0, 8.6 Hz), 7.71 (1H, d, J=3.2 Hz), 7.76 (1H, d, J=3.2 Hz), 7.83 (1H, d, J=1.4 Hz). IR (KBr): 3196, 2994, 2677, 1466, 1269, 1223, 1117, 1051, 1032, 856, 831 cm$^{-1}$.

EXAMPLE 26

Production of 1-(5-Chloro-6-methoxynaphthalen-2-yl)-1-(1H-imidazol-4-yl)-2-methyl-1-propanol (i) Production of (5-Chloro-6-methoxynaphthalen-2-yl)-(1H-imidazol-4-yl)ketone In a similar manner to that described in.Example 20-(i), (5-chloro-6-methoxynaphthalen-2-yl)-(1H-imidazol-4-yl) ketone (0.784 g) was synthesized from 1-chloro-6-formyl-2-methoxynaphthalene (1.474 g).

$^1$H-NMR (DMSO-d$_6$) δ: 4.07 (3H, s), 7.66 (1H, d, J=9.2 Hz), 7.96 (2H, m), 8.15–8.24 (3H, m), 8.92 (1H, s). IR (KBr): 2573, 1632, 1441, 1348, 1279, 1069 cm$^{-1}$.

(ii) Production of 1-(5-Chloro-6-methoxynaphthalen-2-yl)-1-(1H-imidazol-4-yl)-2-methyl-1-propanol In a similar manner to that described in Example 1-(iv), 1-(5-chloro-6-methoxynaphthalen-2-yl)-1-(1H-imidazol-4-yl)-2-methyl-1-propanol (0.117 g) was synthesized from (5-chloro-6-methoxynaphthalen-2-yl)-(1H-imidazol-4-yl) ketone (0.537 g).

$^1$H-NMR (CDCl$_3$) δ: 0.79 (3H, d, J=6.8 Hz), 1.00 (3H, d, J=6.8 Hz), 2.69 (1H, m), 4.01 (3H, s), 6.98 (1H, d, J=1.1 Hz), 7.21–7.30 (1H, m), 7.48 (1H, d, J=1.1 Hz), 7.66 (1H, dd, J=9.2, 1.6 Hz), 7.73 (1H, d, J=8.8 Hz), 8.02 (1H, d, J=1.6 Hz), 8.12 (1H, d, J=9.2 Hz). IR (KBr): 2969, 1601, 1275, 1071 cm$^{-1}$.

EXAMPLE 27

Production of 1-[5-[1-(tert-Butyldimethylsilyloxy)ethyl]-6-methoxynaphthalen-2-yl]-1-(1H-imidazol-4-yl)-2-methyl-1-propanol (i) Production of 1-Acetyl-6-bromo-2-methoxynaphthalene.

2-Bromo-6-methoxynaphthalene (47.75 g) was dissolved in dichloromethane (400 ml). To the solution was added acetylchloride (16 ml), and the mixture was cooled to 0° C. To the mixture was added aluminum chloride (32 g) over a period of 30 min, and the mixture was stirred at 0° C. for 2 h. The reaction mixture was added to a mixture of ice water and aqueous solution of hydrochloric acid. The organic layer was separated and the aqueous layer was extracted with ethyl acetate. The combined extract was washed with saturated sodium chloride solution, dried and concentrated. The residue was washed with hexane-ethyl acetate to give the titled compound (53.24 g) as a colorless solid.

$^1$H-NMR (CDCl$_3$) δ: 2.63 (3H, d, J=0.8 Hz), 3.98 (3H, s), 7.30 (1H, d, J=8.8 Hz), 7.53 (1H, dd, J=1.7, 9.2 Hz), 7.62–7.70 (1H, m), 7.79 (1H, d, J=9.2 Hz), 7.94 (1H, d, J=1.7 Hz); IR (KBr): 3005, 1686, 1586, 1499, 1254, 1080 cm$^{-1}$.

(ii) Production of 1-(6-Bromo-2-methoxynaphthalen-1-yl) ethanol.

1-Acetyl-6-bromo-2-methoxynaphthalene (20.03 g) was dissolved in methanol (400 ml). To the solution was added sodium borohydride (3.91 g), and the mixture was stirred at room temperature for 2 h. To the reaction mixture was added water, and the mixture was concentrated and extracted with ethyl acetate. The organic layer was washed with water and saturated solution of sodium chloride, dried and concentrated. The residue was crystallized from hexane-cyclohexane to give the titled compound (20.09 g) as a colorless solid.

$^1$H-NMR (CDCl$_3$) δ: 1.64 (3H, d, J=6.6 Hz), 3.76 (1H, d, J=5.2 Hz), 4.01 (3H, s), 5.70 (1H, m), 7.29 (1H, d, J=9.2 Hz), 7.52 (1H, dd, J=9.2, 2.2 Hz), 7.78 (1H, d, J=9.2 Hz), 7.93 (1H, d, J=2.2 Hz), 8.02 (1H, d, J=9.2 Hz); IR (KBr): 3412, 2971, 1588, 1497, 1248, 1078 cm$^{-1}$.

(iii) Production of [1-(6-Bromo-2-methoxynaphthalen-1-yl) ethoxy]-tert-butyldimethylsilane.

1-(6-Bromo-2-methoxynaphthalen-1-yl)ethanol (18.57 g) and tert-butyldimethylchlorosilane (11.40 g) were dissolved in DMF (300 ml). To the solution was added imidazole (13.20 g), and the mixture was stirred at room temperature for 14 h. The reaction mixture was concentrated, and to the residue were added water and ethyl acetate. The organic layer was washed with water and saturated solution of sodium chloride, dried and concentrated to give the titled compound (25.58 g) as a colorless liquid.

¹H-NMR (CDCl₃) δ: −0.27 (3H, s), 0.00 (3H, s), 0.81 (9H, s), 1.56 (3H, d, J=6.8 Hz), 3.91 (3H, s), 5.88 (1H, q, J=6.8 Hz), 7.19 (1H, d, J=8.8 Hz), 7.44 (1H, dd, J=9.4, 2.2 Hz), 7.60 (1H, d, J=8.8 Hz), 7.87 (1H, d, J=2.2 Hz), 8.69 (1H, d, J=9.4 Hz); IR (KBr): 2955, 2928, 1588, 1497, 1250, 1094 cm⁻¹.

(iv) Production of [5-[1-(tert-Butyldimethylsilyloxy)-ethyl]-6-methoxynaphthalen-2-yl]-(1-trityl-1H-imidazol-4-yl)methanol In a similar manner to that described in Example 1-(i), the reaction of 4-formyl-1-trityl-1H-imidazole (17.10 g) with (1-(6-bromo-2-methoxynaphthalen-1-yl)ethoxy-tert-butyldimethylsilane (21.70 g) was carried out to give the titled compound (15.25 g) as a colorless solid.

¹H-NMR (CDCl₃) δ: −0.28 (3H, s), 0.00 (3H, s), 0.81 (9H, s), 1.58 (3H, d, J=6.6 Hz), 1.62 (3H, s), 3.17 (1H, m), 3.92 (3H, s), 5.84–5.96 (2H, m), 6.64 (1H, s), 7.04–7.45 (18H, m), 7.78 (1H, d, J=8.8 Hz), 7.74–7.82 (1H, m), 8.74 (1H, d, J=9.0 Hz); IR (KBr): 2928, 1248, 1092, 1065, 833, 702 cm⁻¹.

(v) Production of [5-[1-(tert-Butyldimethylsilyloxy)ethyl]-6-methoxynaphthalen-2-yl]-(1-trityl-1H-imidazol-4-yl)ketone In a similar manner to that described in Example 1-(ii), a reaction was carried out by using [5-[1-(tert-butyldimethylsilyloxy)ethyl]-6-methoxynaphthalen-2-yl]-(1-trityl-1H-imidazol-4-yl)methanol (12.65 g) to give the titled compound (11.72 g).

¹H-NMR (CDCl₃) δ: −0.26 (3H, s), 0.01 (3H, s), 0.82 (9H, s), 1.60 (3H, d, J=6.6 Hz), 3.96 (3H, s), 5.91 (1H, q, J=6.6 Hz), 7.06–7.45 (16H, m), 7.58 (1H, s), 7.76 (1H, s), 7.84 (1H, d, J=9.2 Hz), 8.16 (1H, dd, J=9.2, 1.4 Hz), 8.81–8.93 (2H, m); IR (KBr): 2955,1618, 1254, 1171, 1092, 1067 cm⁻¹.

(vi) Production of [5-[1-(tert-Butyldimethylsilyloxy)-ethyl]-6-methoxynaphthalen-2-yl]-(1H-imidazol-4-yl)ketone. [5-[1-(tert-butyldimethylsilyloxy)ethyl]-6-methoxynaphthalen-2-yl]-(1-trityl-1H-imidazol-4-yl)ketone (5.18 g) and pyridine hydrochloride (1.59 g) were dissolved in methanol (50 ml). The solution was stirred at 50° C. for 1 h. The reaction mixture was concentrated, and water and ethyl acetate were added. The organic layer was washed with saturated aqueous solution of sodium hydrogencarbonate and saturated sodium chloride solution, dried and concentrated. The obtained residue was washed with ether to give the titled compound (2.71 g) as a colorless solid.

¹H-NMR (CDCl₃) δ: −0.23 (3H, s), 0.05 (3H, s), 0.84 (9H, s), 1.63 (3H, d, J=6.6 Hz), 3.99 (3H, s), 5.95 (1H, q, J=6.6 Hz), 7.31 (1H, d, J=9.2 Hz), 7.83–8.03 (4H, m), 8.49 (1H, s), 8.97 (1H, d, J=9.2 Hz); IR (KBr): 2928, 1620, 1321, 1254, 1094, 1067, 831 cm⁻¹.

(vii) Production of 1-[5-[1-(tert-Butyldimethylsilyloxy)ethyl]-6-methoxynaphthalen-2-yl]-1-(1H-imidazol-4-yl)-2-methyl-1-propanol.

In a similar manner to that described in Example 1-(ii), a reaction was carried out by using (5-(1-(tert-butyldimethylsilyloxy)ethyl)-6-methoxynaphthalen-2-yl)(1H-imidazol-4-yl)ketone (1.20 g) to give the title compound (0.53 g) as an amorphous product.

¹H-NMR (CDCl₃) δ: −0.29 (3H, s), −0.01 (3H, s), 0.70–0.90 (12H, m), 0.99 (3H, d, J=7.0 Hz), 1.58 (½×3H, d, J=6.6 Hz), 1.59 (½×3H, d, J=6.6 Hz), 2.60–2.78 (1H, m), 3.90 (3H, s), 5.88 (½×1H, q, J=6.6 Hz), 5.89 (½×1H, q, J=6.6 Hz), 7.00 (1H, d, J=8.3 Hz), 7.16 (1H, d, J=9.0 Hz), 7.42–7.58 (2H, m), 7.69 (1H, d, J=9.6 Hz), 7.91 (1H, d, J=8.3 Hz), 8.71 (1H, d, J=9.0 Hz); IR (KBr): 3094, 2957, 1472, 1250, 1067, 1092, 833 cm⁻¹.

EXAMPLE 28

Production of 1-[5-(1-Hydroxyethyl)-6-methoxynaphthalen-2-yl]-1-[1H-imidazol-4-yl]-2-methyl-1-propanol 1-[5-[1-(tert-Butyldimethylsilyloxy)ethyl]-6-methoxynaphthalen-2-yl]-1-(1H-imidazol-4-yl)-2-methyl-1-propanol (0.499 g) was dissolved in THF (5 ml). To the solution was added tetrabutylammonium fluoride (1.0M in THF; 5 ml), and the mixture was stirred at 60° C. for 8 h. The reaction mixture was concentrated. The obtained residue was purified by silica gel column chromatography (eluent, ethyl acetate:methanol=1:0→10:1) and washed with hexane to give the titled compound (0.24 g) as an amorphous product.

¹H-NMR (CDCl₃) δ: 0.79 (3H, d, J=6.7 Hz), 0.99 (3H, d, J=6.7 Hz), 1.63 (3H, d, J=6.6 Hz), 2.54–2.76 (2H, m), 3.99 (3H, s), 5.68 (1H, q, J=6.6 Hz), 6.95 (1H, d, J=1.2 Hz), 7.19–7.29 (1H, m), 7.42 (1H, s), 7.56 (1H, d, J=9.0 Hz), 7.75 (1H, d, J=9.0 Hz), 7.94–8.06 (2H, m); IR (KBr): 3148, 2969, 1464, 1456, 1248, 1078 cm⁻¹.

EXAMPLE 29

Production of 1-(6-Benzyloxynaphthalen-2-yl)-1-(1H-imidazol-4-yl)-2-methyl-1-propanol (i) Production of (6-Benzyloxynaphthalen-2-yl)(1H-imidazol-4-yl)ketone In a similar manner to that described in Example 27-(vi), a reaction was carried out by using (6-benzyloxynaphthalen-2-yl)(1-trityl-1H-imidazol-4-yl)ketone (82.77 g) to give the titled compound (46.62 g) as a colorless solid.

¹H-NMR (DMSO-d₆) δ: 5.27 (2H, s), 7.28–7.57 (7H, m), 7.88–8.16 (5H, m), 8.81 (1H, s); IR (KBr): 3146, 1626, 1478, 1173, 1011 cm⁻¹.

(ii) Production of 1-(6-Benzyloxynaphthalen-2-yl)-1-(1H-imidazol-4-yl)-2-methyl-1-propanol In a similar manner to that described in Example 1-(iv), a reaction was carried out by using (6-benzyloxynaphthalen-2-yl)(1H-imidazol-4-yl)ketone (46.50 g) to give the titled compound (38.02 g) as a colorless solid.

¹H-NMR (CDCl₃) δ: 0.80 (3H, d, J=6.9 Hz), 1.00 (3H, d, J=6.9 Hz), 2.69 (1H, m), 5.16 (2H, s), 6.98 (1H, s), 7.13–7.76 (11H, m), 7.96 (1H, s); IR (KBr): 2967, 1605, 1264, 1221, 1171, 735 cm⁻¹.

EXAMPLE 30

Production of 1-(1H-Imidazol-4-yl)-1-[6-methoxy-5-(propen-2-yl)naphthalen-2-yl]-2-methyl-1-propanol (i) Production of 2-Bromo-6-methoxy-5-(propen-2-yl)naphthalene.

Methyltriphenylphosphonium bromide (35.75 g) was added to THF (200 ml), and potassium t-butoxide (12.34 g) was slowly added to the mixture under ice cooling, and the mixture was stirred at room temperature for 15 min. To the mixture was added 1-acetyl-6-bromo-2-methoxynaphthalene (25.05 g), and the mixture was stirred at room temperature for 3 h. To the reaction mixture was added water, and the mixture was washed with water and saturated sodium chloride solution, dried and concentrated. To the obtained residue was added hexane, and insoluble materials were filtered off. The filtrate was concentrated under reduced pressure to give the titled compound (23.12 g) as a colorless oil.

¹H-NMR (CDCl₃) δ: 2.10 (3H, d, J=1.4 Hz), 3.94 (3H, s), 4.94 (1H, m), 5.52 (1H, m), 7.23–7.35 (1H, m), 7.47 (1H, dd,

J=9.2, 2.2 Hz), 7.68 (1H, d, J=9.2 Hz), 7.83 (1H, d, J=9.0 Hz), 7.93 (1H, d, J=2.2 Hz); IR (KBr): 2940, 1586, 1495, 1260, 1080 cm$^{-1}$.

(ii) Production of [6-Methoxy-5-(propen-2-yl)naphthalen-2-yl]-(1-trityl-1H-imidazol-4-yl)methanol In a similar manner to that described in Example 1-(i), the reaction of 4-formyl-1-trityl-1H-imidazole (23.30 g) with 2-bromo-6-methoxy-5-(propen-2-yl)naphthalene (23.12 g) was carried out to give the titled compound (19.06 g) as a colorless solid.

$^{1}$H-NMR (CDCl$_3$) δ: 2.10 (3H, s), 3.93 (3H, s) 4.92 (1H, m), 5.50 (1H, m), 5.89 (1H, s), 6.63 (1H, s), 7.04–7.18 (6H, m), 7.21–7.45 (12H, m), 7.72 (1H, d, J=8.8 Hz), 7.81 (1H, s), 7.87 (1H, d, J=8.8 Hz); IR (KBr): 3063, 1595, 1445, 1260, 1080 cm$^{-1}$.

(iii) Production of [6-Methoxy-5-(propen-2-yl)naphthalen-2-yl](1-trityl-1H-imidazol-4-yl)ketone In a similar manner to that described in Example 1-(ii), a reaction was carried out by using [6-methoxy-5-(propen-2-yl)naphthalen-2-yl]-(1-trityl-1H-imidazol-4-yl)methanol (17.49 g) to give the titled compound (14.56 g) as a colorless solid.

$^{1}$H-NMR (CDCl$_3$) δ: 2.12 (3H, s), 3.97 (3H, s), 4.95 (11H, s), 5.53 (1H, s), 7.10–7.24 (6H, m), 7.25–7.43 (10H, m), 7.58 (1H, d, J=1.6 Hz), 7.76 (1H, d, J=1.6 Hz), 7.90 (1H, d, J=9.0 Hz), 7.99 (1H, d, J=9.2 Hz), 8.20 (1H, dd, J=9.2, 1.8 Hz), 8.92 (1H, s); IR (KBr): 2938, 1615, 1520, 1262, 1173, 1078 cm$^{-1}$.

(iv) Production of (1H-Imidazol-4-yl)[6-methoxy-5-(propen-2-yl)naphthalen-2-yl]ketone In a similar manner to that described in Example 27-(vi), a reaction was carried out by using [6-methoxy-5-(propen-2-yl)naphthalen-2-yl]-(1-trityl-1H-imidazol-4-yl)ketone (13.96 g) to give the titled compound (5.69 g) as a colorless solid.

$^{1}$H-NMR (DMSO-d$_6$) δ: 2.06 (3H, s), 3.93 (3H, s), 4.88 (1H, m), 5.50 (1H, m), 7.53 (1H, d, J=9.2 Hz), 7.89–7.99 (3H, m), 8.03 (1H, dd, J=9.0, 1.8 Hz), 8.11 (1H, d, J=9.2 Hz), 8.81 (1H, s); IR (KBr): 2843, 1640, 1605, 1260, 1076 cm$^{-1}$.

(v) Production of 1-(1H-Imidazol-4-yl)-1-[6-methoxy-5-(propen-2-yl)naphthalen-2-yl]-2-methyl-1-propanol In a similar manner to that described in Example 1-(iv), a reaction was carried out by using (1H-imidazol-4-yl)[6-methoxy-5-(propen-2-yl)naphthalen-2-yl]ketone (3.00 g) to give the titled compound (1.23 g) as an amorphous product.

$^{1}$H-NMR (CDCl$_3$) δ: 0.80 (3H, d, J=6.8 Hz), 0.99 (3H, d, J=6.8 Hz), 2.09 (3H, s), 2.56–2.80 (1H, m), 3.92 (3H, s), 4.92 (1H, d, J=1.2 Hz), 5.48 (1H, d, J=1.2 Hz), 6.96 (1H, s), 7.24 (1H, d, J=8.8 Hz), 7.43 (1H, m), 7.52 (1H, dd, J=8.8, 2.0 Hz), 7.73 (1H, d, J=8.8 Hz), 7.87 (1H, d, J=8.8 Hz), 7.96 (1H, s); IR (KBr): 2969, 1497, 1258, 1080, 909, 824, 733 cm$^{-1}$.

EXAMPLE 31

Production of 1-(1H-Imidazol-4-yl)-1-[6-methoxy-5-(propan-2-yl)naphthalen-2-yl]-2-methyl-1-propanol 1-(1H-Imidazol-4-yl)-1-[6-methoxy-5-(propen-2-yl)naphthalen-2-yl]-2-methyl-1-propanol (0.509 g) was dissolved in methanol (40 ml). To the solution was added 10% palladium carbon (0.260 g), and the mixture was stirred at room temperature for 5 h under hydrogen atmosphere (3 atoms). The catalyst was filtered off, and concentrated under reduced pressure. The obtained residue was purified by silica gel column chromatography (eluent, dichloromethane:methanol=50:1→20:1) to give the titled compound (0.234 g) as a colorless solid.

$^{1}$H-NMR (CDCl$_3$) δ: 0.81 (3H, d, J=6.8 Hz), 1.00 (3H, d, J=6.8 Hz), 1.43 (3H, d, J=7.2 Hz), 1.44 (3H, d, J=7.0 Hz), 2.60–2.80 (1H, m), 3.80–3.96 (4H, m), 6.97 (1H, d, J=0.8 Hz), 7.22 (1H, d, J=8.8 Hz), 7.45 (1H, m), 7.54 (1H, dd, J=9.2, 2.0 Hz), 7.67 (1H, d, J=8.8 Hz), 7.95 (1H, d, J=2.0 Hz), 8.06 (1H, d, J=9.2 Hz); IR (KBr): 3077, 2961, 1597, 1464, 1265, 1248, 820 cm$^{-1}$.

EXAMPLE 32

Production of 6-[1-Hydroxy-1-(1H-imidazol-4-yl)-2-methylpropyl]naphthalen-2-yloxymethyl 2,2-dimethylpropionate (i) Production of 6-[1-Hydroxy-1-(1-trityl-1H-imidazol-4-yl)-2-methylpropyl]naphthalen-2-yloxymethyl 2,2-Dimethylpropionate Sodium hydride (60% oil dispersion, 0.120 g) was added to DMF (15 ml), and to the mixture was slowly added 1-(6-hydroxynaphthalen-2-yl)-1-(1-trityl-1H-imidazol-4-yl)-2-methyl-1-propanol (1.397 g) under ice cooling, and the mixture was stirred for 30 min under ice cooling. To the mixture was added iodomethyl pivalate (0.83 g), and the mixture was stirred at room temperature for 6 h. To the mixture were added water and ethyl acetate, and the organic layer was washed with water and saturated solution of sodium chloride. The extract was dried and concentrated. The obtained residue was purified by silica gel column chromatography (eluent, hexane:ethyl acetate=5:1→3:1). Recrystallization from hexane-ethyl acetate to give the titled compound (0.433 g) as a colorless solid.

$^{1}$H-NMR (CDCl$_3$) δ: 0.74 (3H, d, J=6.8 Hz), 0.95 (3H, d, J=6.8 Hz), 1.22 (9H, s), 2.44–2.62 (1H, m), 3.65 (1H, s), 5.87 (1H, s), 6.80 (1H, d, J=1.6 Hz), 7.06–7.24 (7H, m), 7.25–7.40 (11H, m), 7.55 (1H, dd, J=8.8, 1.6 Hz), 7.66 (1H, d, J=8.8 Hz), 7.73 (1H, d, J=9.0 Hz), 7.96 (1H, m); IR (KBr): 2973, 1748, 1480, 1115, 702 cm$^{-1}$.

(ii) Production of 6-[1-Hydroxy-1-(1H-imidazol-4-yl)-2-methylpropyl]naphthalen-2-yloxymethyl 2,2-Dimethylpropionate 6-[1-Hydroxy-2-methyl-1-(1-trityl-1H-imidazol-4-yl)propyl]naphthalen-2-yloxymethyl 2,2-dimethylpropionate (0.381 g) was dissolved in acetic acid (15 ml). To the solution was added palladium carbon (0.200 g), and the mixture was stirred at 50° C. for 2 h under hydrogen atmosphere. The catalyst was filtered off, and the filtrate was concentrated under reduced pressure. To the residue was added ethyl acetate, and the mixture was washed with saturated aqueous solution of sodium hydrogencarbonate and saturated sodium chloride solution. The organic layer was dried and concentrated. The obtained residue was purified by silica gel column chromatography (eluent, dichloromethane:methanol=30:1→20:1) to give the titled compound (0.107 g) as an amorphous product.

$^{1}$H-NMR (CDCl$_3$) δ: 0.80 (3H, d, J=6.8 Hz), 1.00 (3H, d, J=6.8 Hz), 1.21 (9H, s), 2.58–2.78 (1H, m), 5.86 (2H, s), 6.97 (1H, d, J=0.8 Hz), 7.18 (1H, dd, J=8.8, 2.6 Hz), 7.32 (1H, s), 7.44 (1H, d, J=0.8 Hz), 7.58 (1H, dd, J=8.8, 1.8 Hz), 7.67 (1H, d, J=8.8 Hz), 7.74 (1H, d, J=8.8 Hz), 7.98 (1H, m); IR (KBr): 3063, 2971, 1744, 1154, 1028 cm$^{-1}$.

EXAMPLE 33

Production of 1-(6-Isopropoxynaphthalen-2-yl)-1-(1H-imidazol-4-yl)-2-methyl-1-propanol (i) Production of 1-(6-Isopropoxynaphthalen-2-yl)-2-methyl-1-(1-trityl-1H-imidazol-4-yl)-1-propanol In a similar manner to that described in Example 31-(i), the reaction of 1-(6-hydroxynaphthalen-2-yl)-2-methyl-1-(1-trityl-1H-imidazol-4-yl)-1-propanol (0.965 g) with isopropyl iodide (0.20 ml) was carried out to give the titled compound (0.548 g) as a colorless solid.

$^1$H-NMR (CDCl$_3$) δ: 0.75 (3H, d, J=6.8 Hz), 0.94 (3H, d, J=6.8 Hz), 1.39 (6H, d, J=6.0 Hz), 2.42–2.60 (1H, m), 3.64 (1H, s), 4.58–4.75 (1H, m), 6.79 (1H, d, J=1.4 Hz), 7.01–7.40 (18H, m), 7.51 (1H, dd, J=8.6, 1.7 Hz), 7.56–7.73 (2H, m), 7.92 (1H, d, J=1.7 Hz); IR (KBr): 2975, 1603, 1495, 1262, 1184, 702 cm$^{-1}$.

(ii) Production of 1-(6-Isopropoxynaphthalen-2-yl)-1-(1H-imidazol-4-yl)-2-methyl-1-propanol 1-(6-Isopropoxynaphthalen-2-yl)-2-methyl-1-(1-trityl-1H-imidazol-4-yl)-1-propanol (0.438 g) was dissolved in a mixture of acetic acid (20 ml) and water (0.5 ml), and the solution was stirred at 50° C. for 18 h. The solvent was evaporated, and to the mixture was added ethyl acetate. The mixture was washed with saturated aqueous solution of sodium hydrogencarbonate and saturated sodium chloride solution. The organic layer was dried and concentrated. The obtained residue was purified by silica gel column chromatography (eluent, dichloromethane:methanol=40:1→20:1) to give the titled compound (0.170 g) as an amorphous product.

$^1$H-NMR (CDCl$_3$) δ: 0.80 (3H, d, J=6.9 Hz), 0.99 (3H, d, J=6.9 Hz), 1.38 (6H, d, J=6.2 Hz), 2.58–2.78 (1H, m), 4.59–4.75 (1H, m), 6.95 (1H, s), 7.03–7.16 (2H, m), 7.44 (1H, s), 7.48–7.76 (3H, m), 7.93 (1H, s); IR (KBr): 3393, 2975, 1605, 1387, 1264, 1219, 1115 cm$^{-1}$.

EXAMPLE 34

Production of 1-(1H-Imidazol-4-yl)-2-methyl-1-(6-propoxynaphthalen-2-yl)-1-propanol (i) Production of 2-Methyl-1-(6-propoxynaphthalen-2-yl)-1-(1-trityl-1H-imidazol-4-yl)-1-propanol In a similar manner to that described in Example 31-(i), the reaction of 1-(6-hydroxynaphthalen-2-yl)-2-methyl-1-(1-trityl-1H-imidazol-4-yl)-1-propanol (1.265 g) with 1-bromopropane (0.24 ml) was carried out to give the titled compound (0.711 g) as a colorless solid.

$^1$H-NMR (CDCl$_3$) δ: 0.74 (3H, d, J=6.6 Hz), 0.94 (3H, d, J=6.6 Hz), 1.07 (3H, t, J=7.3 Hz), 1.75–1.97 (2H, m), 2.42–2.62 (1H, m), 3.65 (1H, s), 4.02 (2H, t, J=6.6 Hz), 6.79 (1H, d, J=1.2 Hz), 7.06–7.38 (17H, m), 7.47–7.74 (4H, m), 7.91 (1H, d, J=1.6 Hz) IR (KBr): 2965, 1603, 1177, 747, 702 cm$^{-1}$.

(ii) Production of 1-(1H-Imidazol-4-yl)-2-methyl-1-(6-propoxynaphthalen-2-yl)-1-propanol In a similar manner to that described in Example 31-(ii), a reaction was carried out by using 2-methyl-1-(6-propoxynaphthalen-2-yl)-1-(1-trityl-1H-imidazol-4-yl)-1-propanol (0.660 g) to give the titled compound (0.153 g) as a colorless solid.

$^1$H-NMR (CDCl$_3$) δ: 0.79 (3H, d, J=6.6 Hz), 0.99 (3H, d, J=6.6 Hz), 1.06 (3H, t, J=7.3 Hz), 1.75–1.94 (2H, m), 2.53–2.78 (1H, m), 4.01 (2H, t, J=6.6 Hz), 6.93 (1H, d, J=1.1 Hz), 7.08–7.16 (2H, m), 7.41 (1H, d, J=1.1 Hz), 7.52 (1H, dd, J=8.4, 1.8 Hz), 7.58–7.74 (2H, m), 7.92 (1H, s); IR (KBr): 3059, 2965, 1605, 1472, 1264, 1175 cm$^{-1}$.

EXAMPLE 35

Production of 6-[1-Hydroxy-1-(1H-imidazol-4-yl)-2-methylpropyl]naphthalen-2-yl 2,2-Dimethylpropionate (i) Production of 6-[1-Hydroxy-2-methyl-1-(1-trityl-1H-imidazol-4-yl)propyl]naphthalen-2-yl 2,2-Dimethylpropionate In a similar manner to that described in Example 31-(i), the reaction of 1-(6-hydroxynaphthalen-2-yl)-2-methyl-1-(1-trityl-1H-imidazol-4-yl)-1-propanol (1.325 g) with pivalic anhydride (0.77 ml) was carried out in pyridine to give the titled compound (0.940 g) as a colorless solid.

$^1$H-NMR (CDCl$_3$) δ: 0.73 (3H, d, J=6.6 Hz), 0.95 (3H, d, J=6.6 Hz), 1.40 (9H, s), 2.40–2.62 (1H, m), 3.71 (1H, s), 6.79 (1H, d, J=1.0 Hz), 7.06–7.19 (7H, m), 7.26–7.38 (10H, m), 7.46 (1H, d, J=2.2 Hz), 7.56 (1H, dd, J=8.8, 1.8 Hz), 7.68 (1H, d, J=8.8 Hz), 7.79 (1H, d, J=8.8 Hz), 8.02 (1H, s); IR (KBr): 2971, 1752, 1132, 1111, 702 cm$^{-1}$.

(ii) Production of 6-[1-Hydroxy-1-(1H-imidazol-4-yl)-2-methylpropyl]naphthalen-2-yl 2,2-Dimethylpropionate In a similar manner to that described in Example 31-(ii), a reaction was carried out by using 6-[1-hydroxy-2-methyl-1-(1-trityl-1H-imidazol-4-yl)propyl]naphthalen-2-yl 2,2-dimethylpropionate (0.757 g) to give the titled compound (0.388 g) as an amorphous product.

$^1$H-NMR (CDCl$_3$) δ: 0.78 (3H, d, J=7.0 Hz), 0.99 (3H, d, J=7.0 Hz), 1.39 (9H, s), 2.58–2.76 (1H, m), 6.90 (1H, d, J=1.1 Hz), 7.13 (1H, dd, J=8.7, 2.2 Hz), 7.34 (1H, d, J=1.1 Hz), 7.45 (1H, d, J=1.1 Hz), 7.57 (1H, dd, J=8.9, 1.8 Hz), 7.69 (1H, d, J=8.7 Hz), 7.79 (1H, d, J=8.9 Hz), 8.02 (1H, brs); IR (KBr): 3123., 2973, 1748, 1146, 1132, 1111 cm$^{-1}$.

EXAMPLE 36

Production of 1-(1H-Imidazol-4-yl)-1-(6-methoxyethoxynaphthalen-2-yl)-2-methyl-1-propanol (i) Production of 1-(6-Methoxyethoxynaphthalen-2-yl)-2-methyl-1-(1-trityl-1H-imidazol-4-yl)-1-propanol In a similar manner to that described in Example 31-(i), the reaction of 1-(6-hydroxynaphthalen-2-yl)-2-methyl-1-(1-trityl-1H-imidazol-4-yl)-1-propanol (1.329 g) with bromoethylmethyl ether (0.26 ml) was carried out to give the titled compound (0.577 g) as a colorless solid.

$^1$H-NMR (CDCl$_3$) δ: 0.74 (3H, d, J=7.0 Hz), 0.94 (3H, d, J=7.0 Hz), 2.40–2.62 (1H, m), 3.48 (3H, s), 3.66 (1H, s), 3.81 (2H, t, J=4.7 Hz), 4.23 (2H, t, J=4.7 Hz), 6.79 (1H, d, J=1.4 Hz), 7.05–7.21 (8H, m), 7.23–7.38 (10H, m), 7.52 (1H, dd, J=8.8, 1.4 Hz), 7.62 (1H, d, J=8.8 Hz), 7.68 (1H, d, J=9.2 Hz), 7.92 (1H, s); IR (KBr): 2969, 1605, 1447, 1177, 1123, 702 cm$^{-1}$.

(ii) Production of 1-(1H-Imidazol-4-yl)-1-(6-methoxyethoxynaphthalen-2-yl)-2-methyl-1-propanol In a similar manner to that described in Example 32-(ii), a reaction was carried out by using 1-(6-methoxyethoxynaphthalen-2-yl)-2-methyl-1-(1-trityl-1H-imidazol-4-yl)-1-propanol (0.439 g) to give the titled compound (0.057 g) as an amorphous product.

$^1$H-NMR (CDCl$_3$) δ: 0.80 (3H, d, J=6.8 Hz), 1.00 (3H, d, J=6.8 Hz), 2.60–2.80 (1H, m), 3.48 (3H, s), 3.76–3.86 (2H, m), 4.16–4.26 (2H, m), 6.98 (1H, d, J=1.0 Hz), 7.09 (1H, d, J=2.5 Hz), 7.15 (1H, dd, J=8.8, 2.5 Hz), 7.47 (1H, d, J=1.0 Hz), 7.55 (1H, dd, J=8.8, 1.8 Hz), 7.60–7.74 (2H, m), 7.95 (1H, m); IR (KBr): 2930, 1605, 1264, 1221, 1125 cm$^{-1}$.

EXAMPLE 37

Production of 1-(6-Ethoxynaphthalen-2-yl)-1-(1H-imidazol-4-yl)-2-methyl-1-propanol (i) Production of (6-Ethoxynaphthalen-2-yl)(1-trityl-1H-imidazol-4-yl)ketone 2-Bromo-6-ethoxynaphthalene (5.3 g) was dissolved in THF (40 ml). To the solution were added magnesium (0.515 g) and methyl iodide (one drop), and the mixture was vigorously stirred to dissolve magnesium. The reaction mixture was cooled in ice bath, and a solution of 4-formyl-1-tritylimidazole (7 g) in THF (80 ml) was added dropwise over 30 min, and the mixture was stirred at room temperature for 1 h. To the reaction mixture were added saturated aqueous solution of ammonium chloride (40 ml) and water (40 ml), and the mixture was extracted with ethyl acetate. The extract was washed with saturated sodium chloride solution, dried over magnesium sulfate and concentrated. The residue was washed with ethyl acetate to give (6-ethoxynaphthalen-2-yl)(1-trityl-1H-imidazol-4-yl)methanol (6.3 g) as a colorless powder. The product (6.3 g) was dissolved in dichloromethane (120 ml). To the solution was added manganese dioxide (6 g), and the mixture was stirred at room temperature over night. The reaction mixture was filtered with celite, and the filtrate was concentrated. The residue was crystallized from THF-ethyl acetate to give the titled compound (5.5 g) as a colorless powder.

$^1$H-NMR (CDCl$_3$) δ: 1.40 (3H, t, J=7 Hz), 4.08 (2H, q, J=7 Hz), 7.00–7.35 (17H, m), 7.47 (1H, d, J=1.4 Hz), 7.60–7.70 (3H, m), 8.15 (1H, d, J=8.8 Hz), 8.84 (1H, s). IR (KBr): 1620, 1520, 1469, 1263, 1182 cm$^{-1}$.

(ii) Production of 1-(6-Ethoxynaphthalen-2-yl)-1-(1-trityl-1H-imidazol-4-yl)-2-methyl-1-propanol (6-ethoxynaphthalen-2-yl)(1-trityl-1H-imidazol-4-yl)ketone (3.0 g) was dissolved in THF (45 ml). To the solution was added dropwise a solution of isopropylmagnesium chloride in THF (2 M, 4 ml) under ice cooling. The reaction mixture was stirred at room temperature for 30 min. To the mixture were added saturated aqueous solution of ammonium chloride (20 ml) and water (20 ml), and the mixture was extracted with ethyl acetate. The extract was washed with saturated sodium chloride solution, dried and concentrated. The residue was crystallized from ethyl acetate-diisopropyl ether to give the titled compound (1.72 g) as a colorless powder. Mother liquor was purified by silica gel chromatography (eluent, hexane-ethyl acetate=1:2) to give the titled compound (0.43 g).

$^1$H-NMR (CDCl$_3$) δ: 0.75 (3H, d, J=6.8 Hz), 0.94 (3H, d, J=6.8 Hz), 1.47 (3H, t, J=7 Hz), 2.40–2.60 (1H, m), 3.64 (1H, s), 4.16 (2H, q, J=7 Hz), 6.80 (1H, s), 7.05–7.45 (18H, m), 7.50–7.75 (3H, m), 7.93 (1H, s). IR (KBr): 2974, 1603, 1489, 1473, 1394 cm$^{-1}$.

(iii) Production of 1-(6-Ethoxynaphthalen-2-yl)-1-(1H-imidazol-4-yl)-2-methyl-1-propanol 1-(6-Ethoxynaphthalen-2-yl)-1-(1-trityl-1H-imidazol-4-yl)-2-methyl-1-propanol (0.60 g) was dissolved in acetic acid (10 ml). To the solution was added 10% palladium carbon (0.2 g), and the mixture was stirred under hydrogen atmosphere at 50° C. for 2 h then at 60° C. for 3 h. The catalyst was filtered off, filtrate was concentrated to dryness. Recrystallization from THF-ethyl acetate gave the titled compound (0.21 g) as a colorless powder.

$^1$H-NMR (CDCl$_3$) δ: 0.81 (3H, d, J=6.8 Hz), 1.00 (3H, d, J=6.8 Hz), 1.47 (3H, t, J=7 Hz), 2.60–2.80 (1H, m), 4.14 (2H, q, J=7 Hz), 6.99 (1H, s), 7.09–7.15 (2H, m), 7.49–7.55 (2H, m), 7.65 (1H, d, J=8.8 Hz), 7.71 (1h, d, J=8.8 Hz), 7.91 (1H, d, J=1.8 Hz). IR (KBr): 2976, 1633, 1604, 1504, 1473, 1392, 1260, 1219 cm$^{-1}$.

EXAMPLE 38

Production of 1-(6,7-Dimethoxynaphthalen-2-yl)-1-(1H-imidazol-4-yl)-2-methyl-1-propanol (i) Production of Ethyl 2,3-Dimethoxynaphthalen-6-carboxylate A solution of lithium diisopropylamide in THF (2M; 65 ml) was diluted with THF (100 ml), and the solution was cooled to −78° C. To the solution was added dropwise a solution of ethyl 1,3-dioxane-3-propanoate (20.12 g) in THF (30 ml), and the mixture was stirred at −78° C. for 1 h. To the mixture was added dropwise a solution of 3,4-dimethoxybenzaldehyde (17.59 g) in THF (40 ml), and the mixture was stirred at −78° C. for 1 h. The reaction temperature was allowed to room temperature. To the reaction mixture was added saturated aqueous solution of ammonium chloride, and the mixture was extracted with ethyl acetate. The organic layer was washed with saturated sodium chloride solution, dried and concentrated. The residue was purified by silica gel column chromatography (eluent, hexane:ethyl acetate=2:1) to give ethyl 3-(3,4-dimethoxyphenyl)-2-(1,3-dioxane-2-ylmethyl)-3-hydroxypropionate (33.09 g) as an oil. The product was diluted with toluene (400 ml), and to the mixture was added polyphosphoric acid (54 g), and the mixture was stirred at 10° C. for 15 min. After cooling the reaction mixture, water was added. The mixture was extracted with ethyl acetate. The organic layer was washed with saturated aqueous solution of sodium hydrogencarbonate and saturated sodium chloride solution, and dried over anhydrous magnesium sulfate. The solvent was distilled off, and the residue was purified by silica gel column chromatography (eluent, hexane:ethyl acetate=4:1) followed by recrystallization from ethyl acetate-hexane to give the titled compound (16.01 g) as a colorless solid.

$^1$H-NMR (CDCl$_3$) δ: 1.44 (3H, t, J=7.2 Hz), 4.01 (3H, s), 4.02 (3H, s), 4.42 (2H, q, J=7.2 Hz), 7.14 (1H, s;), 7.21 (1H, s), 7.70 (1H, d, J=8.5 Hz), 7.94 (1H, dd, J=8.5, 1.8 Hz), 8.45 (1H, m); IR (KBr): 2978, 1713, 1489, 1238 cm$^{-1}$.

(ii) Production of (6,7-Dimethoxynaphthalen-2-yl)methanol

Lithium aluminum hydride (2.77 g) was added to THF (200 ml) and the mixture was cooled to 0° C. To the mixture was slowly added ethyl 2,3-dimethoxynaphthalen-6-carboxylate (14.30 g), and the mixture was stirred at room temperature for 1 h. To the reaction mixture was added 1N-hydrochloric acid, and the mixture was extracted with ethyl acetate. The organic layer was dried and concentrated. The residue was crystallized from ethyl acetate-diisopropyl ether to give the titled compound (9.73 g) as a colorless solid.

$^1$H-NMR (CDCl$_3$) δ: 3.99 (3H, s), 4.00 (3H, s), 4.80 (2H, s), 7.10 (1H, s), 7.11 (1H, s), 7.33 (1H, dd, J=8.4, 1.8 Hz), 7.60–7.72 (2H, m); IR (KBr): 3299, 1514, 1497, 1262, 1161, 856 cm$^{-1}$.

(iii) Production of 6,7-Dimethoxy-2-formylnaphthalene

In a similar manner to that described in Example 1-(ii), a reaction was carried out by using (6,7-dimethoxynaphthalen-2-yl)methanol (9.26 g) to give the titled compound (7.40 g).

$^1$H-NMR (CDCl$_3$) δ: 4.04 (6H, s), 7.17 (:1H, s), 7.26 (1H, s), 7.76 (1H, d, J=8.4 Hz), 7.83 (1H, dd, J=8.4, 1.6 Hz), 8.19 (1H, m), 10.10 (1H, s); IR (KBr): 1688, 1487, 1211, 1157 cm$^{-1}$.

(iv) Production of (6,7-Dimethoxynaphthalen-2-yl)(1H-imidazol-4-yl)ketone

In a similar manner to that described in Example 20-(i), a reaction was carried out by using 6,7-dimethoxy-2-formylnaphthalene (3.84 g) to give the titled compound (1.31 g) as a colorless solid.

¹H-NMR (DMSO-d₆) δ: 3.93 (3H, s), 3.94 (3H, s), 7.39 (1H, s), 7.53 (1H, s), 7.80–8.03 (5H, m), 8.72 (1H, brs); IR (KBr): 3088, 1636, 1508, 1489, 1260, 1159, 883 cm$^{-1}$.

(v) Production of 1-(6,7-Dimethoxynaphthalen-2-yl)-1-(1H-imidazol-4-yl)-2-methyl-1-propanol In a similar manner to that described in Example 1-(iv), a reaction was carried out by using (6,7-dimethoxynaphthalen-2-yl)(1H-imidazol-4-yl)ketone (0.804 g) to give the titled compound (0.613 g) as a colorless solid.

¹H-NMR (CDCl₃) δ: 0.81 (3H, d, J=6.6 Hz), 1.00 (3H, d, J=6.6 Hz), 2.60–2.78 (1H, m), 3.96 (3H, s), 3.97 (3H, s), 6.98 (1H, d, J=1.0 Hz), 7.07 (1H, s), 7.11 (1H, s), 7.41–7.49 (2H, m), 7.61 (1H, d, J=8.4 Hz), 7.89 (1H, d, J=1.4 Hz); IR (KBr): 3322, 2965, 1510, 1254, 1163, 731 cm$^{-1}$.

EXAMPLE 39

Production of 1-(6-Methoxy-5-methylnaphthalen-2-yl)-1-(1H-imidazol-4-yl)-2-methyl-1-propanol (i) Production of 6-Bromo-2-methoxynaphthalen-1-ylmethanol In a similar manner to that described in Example 27-(ii), a reaction was carried out by using 6-bromo-1-formyl-2-methoxynaphthalene (4.07 g) to give the titled compound (3.20 g) as a colorless solid.

¹H-NMR (CDCl₃) δ: 3.98 (3H, s), 5.14 (2H, s), 7.30 (1H, d, J=9.2 Hz), 7.57 (1H, dd, J=2.2, 9.2 Hz), 7.4 (1H, d, J=9.2 Hz), 7.95 (1H, d, J=2.2 Hz), 7.99 (1H, d, J=9.2 Hz). IR (KBr): 3330, 1589, 1503, 1267, 1250 cm$^{-1}$.

(ii) Production of 6-Bromo-2-methoxy-1-methylnaphthalene

6-Bromo-2-methoxynaphthalen-1-ylmethanol (2.05 g) was dissolved in THF (20 ml). To the solution were added triethylamine (3.2 ml) and the mixture was cooled to 0° C. To the mixture was added methanesulfonylchloride (0.9 ml), and the mixture was stirred at room temperature for 1 h. The solvent was distilled off, and, to the reaction mixture were added water and ethyl acetate. The organic layer, was washed with water and saturated solution of sodium chloride, dried and concentrated, and the residue was dissolved in dimethylsulfoxide (20 ml). To the reaction mixture was added sodium iodide (1.49 g), and the mixture was stirred at room temperature for 1 h. To the mixture was added sodium borohydride (1.09 g), and the mixture was further stirred at room temperature for 1 h. To the reaction mixture was added water and ethyl acetate. The organic layer was washed with water and saturated solution of sodium chloride, dried and concentrated. The obtained residue was purified by silica gel column chromatography (eluent, hexane) to give the titled compound (1.16 g) as a colorless solid.

¹H-NMR (CDCl₃) δ: 2.52 (3H, s), 3.94 (3H, s), 7.25 (1H, d, J=9.0 Hz), 7.52 (1H, dd, J=1.8, 9.0 Hz), 7.61 (1H, d, J=9.0 Hz), 7.81 (1H, d, J=9.0 Hz), 7.92 (1H, d, J=1.8 Hz). IR (KBr): 1588, 1499, 1264, 1250, 11103, 883 cm$^{-1}$.

(iii) Production of 1-(6-Methoxy-5-methylnaphthalen-2-yl)-1-(1H-imidazol-4-yl)-2-methyl-1-propanol 6-Bromo-2-methoxy-1-methylnaphthalene (0.95 g) was dissolved in THF (15 ml). The solution was cooled to −78° C. To the reaction mixture was added dropwise a solution of n-butyllithium in hexane (1.6M, 3 ml), and the mixture was stirred for 15 min. To the mixture was added a solution of 1-(1H-imidazol-4-yl)-2-methyl-1-propanone (0.155 g) in THF (10 ml), and the temperature of the mixture was elevated to room temperature. To the reaction mixture were added aqueous solution of ammonium chloride and ethyl acetate and the organic layer was separated. The aqueous layer was extracted with ethyl acetate. The extracts were combined, dried and concentrated. The residue was purified by silica gel chromatography (eluent, dichloromethane:methanol=20:1) to give the titled compound (0.184 g) as a colorless solid.

¹H-NMR (CDCl₃) δ: 0.81 (3H, d, J=6.8 Hz), 1.01 (3H, d, J=6.8 Hz), 2.52 (3H, s), 2.60–2.80 (1H, m), 3.92 (3H, s), 6.98 (1H, d, J=1.0 Hz), 7.24 (1H, d, J=9.2 Hz), 7.48 (1H, d, J=1.0 Hz), 7.59 (1H, dd, J=2.0, 9.0 Hz), 7.69 (1H, d, J=9.2 Hz), 7.87 (1H, d, J=9.0 Hz), 7.97 (1H, d, J=2.0 Hz); IR (KBr): 2967, 1267, 1254, 1105, 816 cm$^{-1}$.

EXAMPLE 40

Production of 1-(6-Hydroxynaphthalen-2-yl)-1-(1H-imidazol-4-yl)-2-methyl-1-propanol (i) Production of 6-Bromo-1-methyl-2-naphthol 6-Bromo-2-methoxy-1-methylnaphthalene (2.70 g) was dissolved in dichloromethane (20 ml) The solution was cooled to −70° C., and to the solution was added a solution of boron tribromide in dichloromethane (1 M; 14 ml). The mixture was stirred at room temperature for 1 h. To the mixture was added water under ice cooling, and the mixture was extracted with dichloromethane, washed with water and dried. The solvent was distilled off and the residue was purified by column chromatography (eluent, hexane:ethyl acetate=1:1) to give the titled compound (2.55 g) as a pole yellow substance.

¹H-NMR (CDCl₃) δ: 2.50 (3H, s), 5.10) (1H, br s), 7.06 (1H, d, J=8.8 Hz), 7.51 (1H, d, J=8.8 Hz), 7.53 (1H, dd, J=1.9, 9.0 Hz), 7.76 (1H, d, J=9.0 Hz), 7.90 (1H, d, J=1.9 Hz). IR (KBr): 3245, 1591, 1497, 1356, 1341, 1260, 1198, 1080, 893, 878, 810 cm$^{-1}$.

(ii) Production of 2-Bromo-6-tert-butyldimethylsilyloxy-5-methylnaphthalene

6-Bromo-1-methyl-2-naphthol (2.40 g), tert-butyldimethylchlorosilane (1.67 g) and 4-dimethylaminopyridine (catalytic amount) were dissolved in THF (30 ml). The solution was stirred at room temperature for 12 h The solution was diluted with water, and extracted with ethyl acetate. The extract was washed with water, saturated sodium chloride solution, successively. The solvent was distilled off and the residue was purified by column chromatography (eluent, hexane) to give the titled compound (3.35 g) as colorless needles.

¹H-NMR (CDCl₃) δ: 0.23 (6H, s), 1.06 (9H, s), 2.50 (3H, s), 7.07 (1H, d, J=9.0 Hz), 7.49 (1H, d, J=9.0 Hz), 7.51 (1H, dd, J=2.0, 9.0 Hz), 7.77 (1H, d, J=9.0 Hz), 7.90 (1H, d, J=2.0 Hz). IR (KBr): 2926, 2857, 1470, 1460, 1258, 928, 878, 841, 816, 781 cm$^{-1}$.

(iii) Production of 1-(6-tert-Butyldimethylsilyloxynaphthalen-2-yl)-2-methyl-1-(1-trityl-1H-imidazol-4-yl)-1-propanol 2-Bromo-6-tert-butyldimethylsilylloxy-5-methylnaphthalene (3.0 g) was dissolved in THF (50 ml). The solution was cooled to −70° C. To the solution was slowly added a solution of n-butyl lithium in hexane (1.6 M; 6.4 ml), and the mixture was stirred at −70° C. for 20 min. To the mixture was added dropwise a solution of 4-formyl-1-trityl-1H-imidazole (2.71 g) in THF (15 ml). The mixture was stirred for 20 min at −70° C. To the mixture was added water, and the mixture was extracted with ethyl acetate, washed with saturated sodium chloride solution and dried. The solvent was distilled off and the residue was purified by column chromatography (eluent, hexane:THF=2:1) followed by recrystallization from isopropyl ether to give the titled compound (4.06 g) as a colorless powder.

¹H-NMR (CDCl₃) δ: 0.22 (6H, s), 0.75 13H, d, J=6.7 Hz), 0.95 (3H, d, J=6.7 Hz), 1.05 (9H, s), 2.47–2.60 (1H, m), 2.50

(3H, s), 3.63 (1H, s), 6.80 (1H, d, J=1.4 Hz), 7.03 (1H, d, J=8.8 Hz), 7.11–7.18 (6H, m), 7.29–7.37 (10H, m), 7.54 (1H, d, J=2.4 Hz), 7.57 (1H, d, J=1.0 Hz), 7.82 (1H, d, J=9.2 Hz), 7.92 (1H, d, J=1.8 Hz). IR (KBr): 2961, 2930, 1472, 1445, 1242, 934, 839, 747, 702 cm$^{-1}$.

(iv) Production of 1-(6-tert-Butyldimethylsilyloxynaphthalen-2-yl)-1-(1H-imidazol-4-yl)-2-methyl-1-propanol In a similar manner to that described in Example 50-(iii), a reaction was carried out by using 1-(6-tert-butyldimethylsilyloxynaphthalen-2-yl)-2-methyl-1-(1-trityl-1H-imidazol-4-yl)-1-propanol (3.50 g) to give the titled compound (1.76 g) as a colorless powder.

$^1$H-NMR (CDCl$_3$) δ: 0.21 (6H, s), 0.81 (, 3H, d, J=6.8 Hz), 1.0 (3H, d, J=6.6 Hz), 1.05 (9H, s), 2.49 (3H, s), 2.62–2.76 (1H, m), 3.00 (1H, s), 6.95 (1H, d, J=1.0 Hz), 7.03 (1H, d, J=9.0 Hz), 7.42 (1H, d, J=1.0 Hz), 7.58 (1H, d, J=9.0 Hz), 7 57 (1H, d, J=9.0 Hz), 7.84 (1H, d, J=9.0 Hz), 7.94 (1H, d, J=1.8 Hz). IR (KBr): 3198, 2961, 2930, 1472, 1238, 928, 916, 839, 822, 783 cm$^{-1}$.

(v) Production of 1-(6-Hydroxynaphthalen-2-yl)-1-(1H-imidazol-4-yl)-2-methyl-1-propanol To a solution of 1-(6-tert-butyldimethylsilyloxynaphthalen-2-yl -1-(1H-imidazol-4-yl)-2-methylpropanol (1.60 g) in THF (10 mL) was added 70% aqueous solution of hydrogen fluoride-pyridine (3 ml) under ice cooling. The mixture was stirred for 30 min under ice cooling and for 2 h at room temperature. The mixture was neutralized with saturated solution of sodium hydrogencarbonate, extracted with dichloromethane and dried. The solvent was distilled off and the residue was purified by column chromatography (eluent, dichloromethane:methanol=10:1→5:1) to give the titled compound (856 mg) as a colorless powder.

$^1$H-NMR (CDCl$_3$+CD$_3$OD) δ: 0.82 (3H, (1, J=6.7 Hz), 0.99 (3H, d, J=6.7 Hz), 2.49 (3H, s), 2.70–2.84 (1H, m), 7.01 (1H, d, J=1.4 Hz), 7.09 (1H, d, J=8.9 Hz), 7.54–7.60 (3H, m), 7.82 (1H, d, J=8.9 Hz), 7.89 (1H, d, J=1.8 Hz). IR (KBr): 3218, 2980, 1505, 1468, 1366, 1350, 1269, 1240, 1169, 995, 800 cm$^{-1}$.

EXAMPLE 41

Production of 1-(5,6-Dimethoxynaphthalen-2-yl)-1-(1H-imidazol-4-yl)-2-methyl-1-propanol (i) Production of 6-Bromo-1-formyl-2-methoxynaphthalene Phosphoryl chloride (32.83 g) was added dropwise to DMF (50 ml) at 0° C. The mixture was stirred at room temperature for 30 min. To the mixture was added 6-bromo-2-methoxynaphthalene (21.10 g), and the mixture was stirred at 100° C. for 7 h. To the reaction mixture was added a large amount of water, and the resulting precipitate was collected by filtration and washed with water and ethanol. The precipitate was dried and recrystallized from diisopropylether to give the titled compound (6.20 g) as a brown solid.

$^1$H-NMR (CDCl$_3$) δ: 4.06 (3H, s), 7.33 (1H, d, J=9.2 Hz), 7.66 (1H, dd, J=2.2, 9.2 Hz), 7.93 (1H, d, J=2.2 Hz), 7.96 (1H, d, J=9.2 Hz), 9.18 (1H, d, J=9.2 Hz). IR (KBr): 1665, 1501, 1269, 1154 cm$^{-1}$.

(ii) Production of 6-Bromo-2-methoxy-1-naphthyl Formate

6-Bromo-1-formyl-2-methoxynaphthalene (1.15 g) and m-chloroperbenzoic acid (1.70 g) were dissolved in dichloromethane (100 ml). To the solution was added anhydrous sodium dihydrogenphosphate (1.59 g); and the mixture was stirred at room temperature for 16 h. The organic layer was washed with saturated aqueous solution of sodium hydrogencarbonate, 1N-hydrochloric acid and a solution of sodium chloride, successively, dried and concentrated. The obtained residue was washed with hexane to give the titled compound (0.96 g) as a colorless solid.

$^1$H-NMR (CDCl$_3$) δ: 3.96 (3H, s), 7.36 (1H, d, J=9.0 Hz), 7.56 (1H, dd, J=1.8, 8.8 Hz), 7.68 (1H, d, J=9.0 Hz), 7.72 (1H, d, J=8.8 Hz), 7.97 (1H, d, J=1.8 Hz), 8.42 (1H, s). IR (KBr): 1728, 1591, 1499, 1281, 1177, 1140, 1084 cm$^{-1}$.

(iii) Production of 6-Bromo-1,2-dimethoxynaphthalene

6-Bromo-2-methoxy-1-naphthyl formate (0.757 g) was dissolved in a mixture of ethanol (8 ml) and water (4 ml). To the solution was added lithium hydroxide (0.176 g), and the mixture was stirred at 60° C. for 2 h. The solvent was distilled off and the residue was dissolved in DMF (10 ml). To the solution were added potassium carbonate (0.483 g) and methyl iodide (0.5 ml), and the mixture was stirred at room temperature for 6 h. To the reaction mixture were added water and ethyl acetate. The organic layer was washed with water and saturated solution of sodium chloride, dried and concentrated. The obtained residue was purified by silica gel column chromatography (hexane:ethyl acetate= 20:1) to give the titled compound (0.223 g) as a colorless solid.

$^1$H-NMR (CDCl$_3$) δ: 3.98 (3H, s), 3.99 (3H, s), 7.29 (1H, d, J=8.8 Hz), 7.49 (1H, d, J=8.8 Hz), 7.51 (1H, dd, J=1.8, 8.8 Hz), 7.92 (1H, d, J=1.8 Hz), 7.99 (1H, d, J=8.8 Hz). IR (KBr): 1588, 1354, 1273, 1069 cm$^{-1}$.

(iv) Production of 1-(5,6-Dimethoxynaphthalen-2-yl)-1-(1H-imidazol-4-yl)-2-methyl-1-propanol 6-Bromo-1,2-dimethoxynaphthalene (2.10 g) was dissolved in THF (30 ml). The solution was cooled to −78° C. To the reaction mixture was added dropwise a solution of n-butyllithium in hexane (1.6M: 6 ml), and the mixture was stirred for 1 h. To the mixture was added a solution of 1-(1H-imidazol-4-yl)-2-methyl-1-propanone (0.367 g) in THF (10 ml), and the temperature of the mixture was elevated to room temperature. To the reaction mixture were added an aqueous solution of ammonium chloride and ethyl acetate, and the mixture was extracted with ethyl acetate. The organic layer was dried and concentrated. The obtained residue was purified by silica gel column chromatography (dichloromethane:methanol=20:1) to give the titled compound (0.459 g) as a colorless solid.

$^1$H-NMR (CDCl$_3$) δ: 0.80 (3H, d, J=6.8 Hz), 1.00 (3H, d, J=6.8 Hz), 2.60–2.80 (1H, m), 3.96 (3H, s), 6.97 (1H, d, J=1.1 Hz), 7.24 (1H, d, J=8.8 Hz), 7.46 (1H, d, J=1.1 Hz), 7.56 (1H, dd, J=1.8, 8.8 Hz), 7.98 (1H, d, J=1.8 Hz), 8.02 (1H, d, J=8.8 Hz). IR (KBr): 2969, 1360, 1270, 1100, 1061, 733 cm$^{-1}$.

EXAMPLE 42

Production of 6-[1-Hydroxy-1-(1H-imidazol-4-yl)-2-methylpropyl]-3-methoxy-2-naphthol (i) Production of Ethyl 6-Hydroxy-7-methoxy-2-naphthoate In a similar manner to that described in Example 38-(i), a reaction was carried out by using 4-benzyloxy-3-methoxybenzaldehyde (24.90 g) to give the titled compound (3.00 g) as a colorless solid.

$^1$H-NMR (CDCl$_3$) δ: 1.43 (3H, t, J=7.2 Hz), 4.03 (3H, s), 4.38 (2H, q, J=7.2 Hz), 6.16 (1H, s), 7.21 (1H, s), 7.28 (1H, s), 7.67 (1H, d, J=8.6 Hz), 7.87–7.96 (2H, m), 8.45 (1H, s). IR (KBr): 3382, 1709, 1487, 1267, 1240 cm$^{-1}$.

(ii) Production of Ethyl 6-Benzyloxy-7-methoxy-2-naphthoate

Ethyl 6-hydroxy-7-methoxy-2-naphthoate (2.95 g) and potassium carbonate (2.21 g) were dissolved in DMF (20 ml). To the solution was added dropwise benzyl bromide (1.5 ml), and the mixture was stirred at room temperature for 12 h. To the reaction mixture was added water, and resulting precipitate was filtered off. The filtrate was dissolved in ethyl acetate. The solution was washed with water and saturated solution of sodium chloride, dried and concentrated. The obtained residue was recrystallized from diisopropyl ether-hexane to give the titled compound (2.69 g) as a colorless solid.

$^1$H-NMR (CDCl$_3$) δ: 1.43 (3H, t, J=7.1 Hz), 4.02 (3H, s), 4.42 (2H, q, J=7.1 Hz), 5.29 (2H, s), 7.19 (1H, s), 7.24 (1H, s), 7.30–7.46 (3H, m), 7.46–7.55 (2H, m), 7.65 (1H, d, J=8.6 Hz), 7.92 (1H, dd, J=1.7, 8.6 Hz), 8.46 (1H, d, J=1.7 Hz). IR (KBr): 1713, 1487, 1240, 1194, 1165 cm$^{-1}$.

(iii) Production of (6-Benzyloxy-7-methoxynaphthalen-2-yl)methanol

In a similar manner to that described in Example 38-(ii), a reaction was carried out by using ethyl 6-benzyloxy-7-methoxy-2-naphthoate (2.51 g) to give the titled compound (1.79 g) as a colorless solid.

$^1$H-NMR (CDCl$_3$) δ: 4.00 (3H, s), 4.80 (2H, s), 5.27 (2H, s), 7.13 (1H, s), 7.16 (1H, s), 7.27–7.44 (4H, m), 7.46–7.54 (2H, m), 7.59–7.69 (2H, m). IR (KBr): 3310, 1489, 1256, 1161, 856 cm$^{-1}$.

(iv) Production of 6-Benzyloxy-7-methoxy-2-naphthoaldehyde

In a similar manner to that described in Example 1-(ii), a reaction was carried out by using (6-benzyloxy-7-methoxynaphthalen-2-yl)methanol (1.69 g) to give the titled compound (1.48 g) as a colorless solid.

$^1$H-NMR (CDCl$_3$) δ: 4.03 (3H, s), 5.13 (2H, s), 7.21 (1H, s), 7.27 (1H, s), 7.30–7.55 (5H, m), 7.70 (1H, d, J=8.4 Hz), 7.80 (1H, dd, J=1.6, 8.4 Hz), 8.18 (1H, brs), 10.09 (1H, s). IR (KBr): 1690, 1485, 1256, 1211, 1155 cm$^{-1}$.

(v) Production of 1-(6-Benzyloxy-7-methoxynaphthalen-2-yl)-1-(1H-imidazol-4-yl)methanol In a similar manner to that described in Example 20-(i), a reaction was carried out by using 6-benzyloxy-7-methoxy-2-naphthoaldehyde (1.33 g) to give the titled compound (1.20 g) as a colorless solid.

$^1$H-NMR (CDCl$_3$+CD$_3$OD) δ: 3.98 (3H, s), 5.26 (2H, s), 5.92 (1H, s), 6.67 (1H, m), 7.14 (1H, s), 7.16 (1H, s), 7.30–7.64 (8H, m), 7.75 (1H, s). IR (KBr): 3034, 1510, 1487, 1248 cm$^{-1}$.

(vi) Production of 6-Benzyloxy-7-methoxynaphthalen-2-yl)(1H-imidazol-4-yl)methanone In a similar manner to that described in Example 1-(ii), a reaction was carried out by using (6-benzyloxy-7-methoxynaphthalen-2-yl)(1H-imidazol-4-yl)methanol (1.10 g) to give the titled compound (1.05 g) as a colorless solid.

$^1$H-NMR (CDCl$_3$+CD$_3$OD) δ: 4.03 (3H, s), 5.31 (2H, s), 7.23 (1H, s), 7.28 (1H, s), 7.30–7.56 (5H, m), 7.73 (1H, d, J=8.6 Hz), 7.76–7.94 (2H, m), 8.40 (1H, brs). IR (KBr): 3034, 1632, 1483, 1256, 1159 cm$^{-1}$.

(vii) Production of 1-(6-Benzyloxy-7-methoxynaphthalen-2-yl)-1-(1H-imidazol-4-yl)-2-methyl-1-propanol In a similar manner to that described in Example 1-(iv), a reaction was carried out by using (6-benzyloxy-7-methoxynaphthalen-2-yl)(1H-imidazol-4-yl)methanone (0.998 g) to give the titled compound (0.520 g) as a colorless solid.

$^1$H-NMR (CDCl$_3$) δ: 0.80 (3H, d, J=6.6 Hz), 1.00 (3H, d, J=6.6 Hz), 2.58–2.78 (1H, m), 3.97 (3H, s), 5.24 (2H, s), 6.96 (1H, d, J=1.2 Hz), 7.11 (1H, s), 7.13 (1H, s), 7.26–7.58 (8H, m), 7.85 (1H, s). IR (KBr): 3191, 1507, 1250, 1163, 1005 cm$^{-1}$.

(viii) Production of 6-1-Hydroxy-1-(1H-imidazol-4-yl)-2-methylpropyl]-3-methoxy-2-naphthol In a similar manner to that described in Example 17, a reaction was carried out by using 1-(6-benzyloxy-7-methoxynaphthalen-2-yl)-1-(1H-imidazol-4-yl)-2-methyl-1-propanol (0.320 g) to give the titled compound (0.238 g) as a colorless solid.

$^1$H-NMR (CDCl$_3$+CD$_3$OD) δ: 0.80 (3H, d, J=6.8 Hz), 1.00 (3H, d, J=6.8 Hz), 2.58–2.76 (1H, m), 3.97 (3H, s), 6.99 (1H, d, J=1.0 Hz), 7.10 (1H, s), 7.17 (1H, s), 7.38 (1H, dd, J=1.9, 8.7 Hz), 7.49 (1H, d, J=1.0 Hz), 7.55 (1H, d, J=8.7 Hz), 7.83 (1H, d, J=1.9 Hz). IR (KBr): 2969, 1512, 1487, 1252, 1161, 862 cm$^{-1}$.

EXAMPLE 43

Production of 1-(5-Hydroxymethyl-6-methoxynaphthalen-2-yl)-1-(1H-imidazol-4-yl)-2-methyl-1-propanol In a similar manner to that described in Example 39-(iii), a reaction was carried out by using (6-bromo-2-methoxynaphthalen-1-yl)methanol (0.790 g) to give the titled compound (0.135 g) as a colorless solid.

$^1$H-NMR (CDCl$_3$+CD$_3$OD) δ: 0.80 (3H, d, J=6.7 Hz), 1.00 (3H, d, J=6.7 Hz), 2.59–2.78 (1H, m), 3.97 (3H, s), 5.13 (2H, s), 6.97 (1H, d, J=1.1 Hz), 7.27 (1H, d, J=8.8 Hz), 7.46 (1H, d, J=1.1 Hz), 7.59 (1H, dd, J=2.0, 9.2 Hz), 7.82 (1H, d, J=9.2 Hz), 7.95 (1H, d, J=2.0 Hz), 8.02 (1H, d, J=8.8 Hz). IR (KBr): 3156, 1252, 1096, 1001, 822 cm$^{-1}$.

EXAMPLE 44

Production of 1-(1H-Imidazol-4-yl)-1-[6-methoxy-5-methoxymethyl-naphthalen-2-yl]-2-methyl-1-propanol (i) Production of 6-Bromo-2-methoxy-1-methoxymethylnaphthalene Sodium hydride (60% oil dispersion, 0.44 g) was suspended in a mixture of THF (20 ml) and DMF (20 ml), and the suspension was cooled to 0° C. To the suspension was added (6-bromo-2-methoxynaphthalen-1-yl)methanol (2.59 g), and the mixture was stirred for 15 min. To the mixture was added methyl iodide (0.70 ml), and the mixture was stirred at room temperature for 1 h. The solvent was distilled off under reduced pressure. To the reaction mixture were added ethyl acetate and water, and the organic layer was washed with water and saturated sodium chloride solution. The organic layer was dried and concentrated. The obtained residue was recrystallized from hexane-ethyl acetate to give the titled compound (1.59 g) as a colorless solid.

$^1$H-NMR (CDCl$_3$) δ: 3.43 (3H, s), 3.96 (3H, s), 4.49 (2H, s), 7.29 (1H, d, J=9.2 Hz), 7.55 (1H, dd, J=2.2, 8.8 Hz), 7.74 (1H, d, J=9.2 Hz), 7.91–7.99 (2H, m). IR (KBr): 2976, 1503, 1265, 1250, 1084 cm$^{-1}$.

(ii) Production of 1-(1H-Imidazol-4-yl)-1-[6-methoxy-5-methoxymethyl-naphthalen-2-yl]-2-methyl-1-propanol In a similar manner to that described in Example 39-(iii), a reaction was carried out by using 6-bromo-2-methoxy-1-methoxymethylnaphthalene (1.51 g) to give the titled compound (0.293 g) as a colorless solid.

$^1$H-NMR (CDCl$_3$) δ: 0.80 (3H, d, J=6.7 Hz), 0.99 (3H, d, J=6.7 Hz), 2.58–2.80 (1H, m), 3.44 (3H, s), 3.93 (3H, s), 4.94 (2H, s), 6.90 (1H, s), 7.16–7.30 (1H, m), 7.38 (1H, s), 7.58 (1H, d, J=9.2 Hz), 7.80 (1H, d, J=8.4 Hz), 7.92–8.06 (2H, m). IR (KBr): 2967, 1271, 1252, 1088, 733 cm$^{-1}$.

EXAMPLE 45

Production of 1-(5-Ethyl-6-methoxynaphthalen-2-yl)-1-(1H-imidazol-4-yl)-2-methyl-1-propanol (i) Production of 6-Bromo-1-ethenyl-2-methoxynaphthalene A mixture of methyltriphenylphosphonium bromide (2.64 g) and potassium t-butoxide (0.84 g) in THF (30 ml) was stirred for 2 h under ice cooling. To the mixture was added 6-bromo-1-formyl-2-methoxynaphthalene (1.6 g), and the mixture was stirred at room temperature for 1 h. To the reaction mixture was added 1N-hydrochloric acid, and the mixture was extracted with ethyl acetate. The extract was washed with solution of sodium chloride, dried and concentrated. The residue was purified by silica gel chromatography (eluent, hexane-ethyl acetate=20:1) followed by recrystallization from hexane to give the titled compound (0.43 g) as a colorless powder.

$^1$H-NMR (CDCl$_3$) δ: 3.96 (3H, s), 5.69 (1H, dd, J=11.6 Hz, 2.0 Hz), 5.76 (1H, dd, J=5.8 Hz, 2.0 Hz), 7.01 (1H, d, J=12 Hz), 7.10 (1H, d, J=11.6 Hz), 7.29 (1H, d, J=9.4 Hz), 7.50 (1H, d, J=9.2 Hz, 2.0 Hz), 7.68 (1H, d, J=9.2 Hz), 7.93 (1H, d, J=2 Hz), 8.06 (1H, d, J=9.4 Hz). IR (KBr): 1585, 1496, 1267, 1249 cm$^{-1}$.

(ii) Production of 1-(5-Ethenyl-6-methoxynaphthalen-2-yl)-1-(1-trityl-1H-imidazol-4-yl)-2-methyl-1-propanol 6-Bromo-1-ethenyl-2-methoxynaphthalene (1.20 g) was dissolved in THF (12 ml). To the solution was added dropwise a solution of n-butyllithium in hexane (1.6M: 3.4 ml) at −70° C., and the mixture was stirred for 30 min. A solution of 1-(1H-imidazol-4-yl)-2-methyl-1-propanone (1.73 g) in THF (10 ml) was stirred for 40 min, and the temperature of the mixture was elevated to room temperature. To the reaction mixture were added an aqueous solution of ammonium chloride (10 ml) and water (10 ml), and the mixture was extracted with ethyl acetate. The organic layer was washed with saturated sodium chloride solution, dried and concentrated. The residue was crystallized from ethyl acetate to give the titled compound (1.28 g) as a colorless powder. Mother liquor was purified by silica gel column chromatography (eluent, hexane-ethyl acetate=1:1) followed by recrystallization from ethyl acetate-diisopropyl ether to give the titled compound (0.23 g).

IR (KBr): 2966, 1591, 1494, 1444, 1251, 702 cm$^{-1}$.

(iii) Production of 1-(5-Ethyl-6-methoxynaphthalen-2-yl)-1-(1H-imidazol-4-yl)-2-methyl-1-propanol 1-(5-Ethenyl-6-methoxynaphthalen-2-yl)-1-(1-trityl-1H-imidazol-4-yl)-2-methyl-1-propanol (1.28 g) was dissolved in a mixture of methanol and THF (1:1, 50 ml). To the solution was added 10% palladium carbon (0.3 g), and the mixture was stirred at room temperature for 2 h under hydrogen atmosphere. The catalyst was filtered off, and the filtrate was concentrated. The residue was dissolved in a mixed solution of methanol and THF (3:1, 40 ml). To the solution was added pyridine hydrochloride (0.65 g), and the mixture was stirred at 60° C. for 3 h. The reaction mixture was concentrated to dryness, and to the residue were added ethyl acetate and 1N-hydrochloric acid (20 ml). The organic layer was extracted four times with 1N-hydrochloric acid. The aqueous layer was neutralized with an aqueous solution of sodium hydrogencarbonate and extracted with ethyl acetate. The organic layer was washed with saturated sodium chloride solution, dried and concentrated. The residue was purified by silica gel chromatography (eluent, dichloromethane-methanol=10:1) followed by crystallization from dichloromethane-diisopropyl ether-hexane to give the titled compound (0.49 g) as a colorless powder.

$^1$H-NMR (CDCl$_3$) δ: 0.81 (3H, d, J=6.8 Hz), 1.00 (3H, d, J=6.8 Hz), 1.21 (3H, t, J=7.5 Hz), 2.71 (1H, quint, J=6.8 Hz), 3.60 (2H, q, J=7.5 Hz), 3.93 (3H, s), 6.99 (1H, d, J=1.0 Hz), 7.24 (1H, d, J=9.2 Hz), 7.49 (1H, d, J=1.0 Hz), 7.58 (1H, dd, J=8.8 Hz, 2.0 Hz), 7.69 (1H, d, J=8.8 Hz), 7.89 (1H, d, J=9.2 Hz), 7.97 (1H, d, J=2 Hz). IR (KBr): 2966, 1628, 1597, 1502, 1479, 1464, 1261, 1107 cm$^{-1}$.

EXAMPLE 46

Production of 1-(5-Ethenyl-6-methoxynaphthalen-2-yl)-1-(1H-imidazol-4-yl)-2-methyl-1-propanol 1-(5-Ethenyl-6-methoxynaphthalen-2-yl)-1-(1-trityl-1H-imidazol-4-yl)-2-methyl-1-propanol (230 mg) was dissolved in a mixed solution of methanol and THF (3:1, 20 ml). To the solution was added pyridine hydrochloride (0.12 g), and the mixture was stirred at 60° C. for 3 h. The reaction mixture was concentrated to dryness, and to the residue were added ethyl acetate and 1N-hydrochloric acid (10 ml). The organic layer was extracted four times with 1N-hydrochloric acid. The aqueous layer was neutralized with an aqueous solution of sodium hydrogencarbonate and extracted with ethyl acetate. The organic layer was washed with saturated sodium chloride solution, dried and concentrated. The residue was purified by silica gel chromatography (eluent, dichloromethane-methanol=10:1) to give the titled compound (91 mg).

$^1$H-NMR (CDCl$_3$) δ: 0.79 (3H, d, J=6.8 Hz), 0.99 (3H, d, J=6.8 Hz), 2.65 (1H, quint, J=6.8 Hz), 3.92 (3H, s), 5.65–5.80 (2H, m), 6.91 (1H, d, J=1.0 Hz), 7.03 (1H, d, J=11.6 Hz), 7.11 (1H, d, J=11.8 Hz), 7.21 (1H, d, J=9 Hz), 7.36 (1H, s), 7.51 (1H, dd, J=9 Hz, 2.0 Hz), 7.71 (1H, d, J=9 Hz), 7.95 (1H, d, J=2.0 Hz), 8.09 (1H, d, J=9 Hz). IR (KBr): 2968, 1630, 1591, 1498, 1464, 1269, 1251 cm$^{-1}$.

EXAMPLE 47

Production of 1-(5-Bromo-6-methoxynaphthalen-2-yl)-1-(1H-imidazol-4-yl)-2-methyl-1-propanol (6-Methoxynaphthalen-2-yl)-1-(1-trityl-1H-imidazol-4-yl)-2-methyl-1-propanol (1.0 g) was dissolved in a mixed solution of dichloromethane and methanol (1:1, 10 ml). To the solution was added pyridinium hydrobromide perbromide (0.77 g), and the mixture was stirred at room temperature for 6 h. The solvent was distilled off, and to the reside was added water, and the resulting precipitate (0.75 g) was collected to give the brominated product.

In a similar manner to that described in Example 46, a reaction was carried out by using the brominated product (0.2 g) to give the titled compound (89 mg) as a colorless powder.

$^1$H-NMR (CDCl$_3$) δ: 0.79 (3H, d, J=7 Hz), 0.99 (3H, d, J=7 Hz), 2.69 (1H, quint, J=7 Hz), 4.00 (3H, s), 6.97 (1H, s), 7.23 (1H, d, J=9.2 Hz), 7.47 (1H, s), 7.65 (1H, dd, J=9.2 Hz, 1.8 Hz), 7.78 (1H, d, J=9.2 Hz), 8.02 (1H, d, J=1.8 Hz), 8.13 (1H, d, J=9.2 Hz). IR (KBr): 2968, 1628, 1599, 1493, 1273, 1066 cm$^{-1}$.

EXAMPLE 48

Production of 1-(6-Fluoromethyloxynaphthalen-2-yl)-1-(1H-imidazol-4-yl)-2-methyl-1-propanol (i) Production of 2-Bromo-6-fluoromethyloxynaphthalene Sodium hydride (60% oil dispersion, 1.03 g) was added to DMF (30 ml). To the mixture was added 6-bromo-2-naphthol (4.80 g) under ice cooling, and the mixture was stirred at for 20 min. To the mixture was added dropwise a solution of bromofluoromethane (3.0 g) in DMF (10 ml).

The mixture was stirred for 1 h under ice cooling. To the mixture was added water (300 ml), and the resulting precipitate was collected by filtration, washed with water and dried. The resulting solid was purified by silica gel chromatography (eluent, hexane:ethyl acetate=1:1) followed by recrystallization from hexane to give the titled compound (4.55 g) as pale brown plates.

$^1$H-NMR (CDCl$_3$) δ: 5.68 (1H, s), 5.95 (1H, s), 7.26 (1H, dd, J=2.5, 8.9 Hz), 7.41 (1H, d, J=2.4 Hz), 7.52 (1H, dd, J=2.0, 8.8 Hz), 7.63 (1H, d, J=8.8 Hz), 7.0 (1H, d, J=9.2 Hz), 7.95 (1H, d, J=1.8 Hz). IR (KBr): 2928, 1590, 1501, 1252, 1204, 1084, 968, 885 cm$^{-1}$.

(ii) Production of 1-(6-Fluoromethyloxynaphthalen-2-yl)-2-methyl-1-(1-trityl-1H-imidazol-4-yl)-1-propanol 2-Bromo-6-fluoromethyloxynaphthalene (2.10 g) was dissolved in ether (100 ml), and the solution was cooled to −70° C. To the solution was slowly added a solution of n-butyllithium in hexane (1.6 M, 5.7 ml), and the mixture was stirred at −70° C. for 20 min. To the mixture was added dropwise a solution of 4-formyl-1-trityl-1H-imidazole (1.58 g) in THF (10 ml). The mixture was stirred for 20 min at −70° C. To the mixture was added water, and the mixture was extracted with ethyl acetate and dried. The solvent was distilled off and the residue was purified by silica gel chromatography (eluent, hexane:ethyl acetate=1:1) followed by recrystallization from diisopropyl ether to give the titled compound (1.73 g) as colorless needles.

$^1$H-NMR (CDCl$_3$) δ: 0.73 (3H, d, J=6.6 Hz), 0.95 (3H, d, J=6.6 Hz), 2.45–2.59 (1H, m), 3.71 (1H, s), 5.67 (1H, s), 5.95 (1H, s), 6.80 (1H, d, J=1.2 Hz), 7.10–7.17 (6H, m), 7.22 (1H, d, J=2.5, 8.9 Hz), 7.29–7.36 (10H, m), 7.42 (1H, d, J=2.4 Hz), 7.55 (1H, dd, J=1.7, 8.7 Hz), 7.68 (1H, d, J=8.8 Hz), 7.76 (1H, d, J=9.0 Hz), 8.00 (1H, s). IR (KBr): 3200, 2967, 1142, 1080, 993, 756, 750, 700 cm$^{-1}$.

(iii) Production of 1-(6-Fluoromethyloxynaphthalen-2-yl)-1-(1H-imidazol-4-yl)-2-methyl-1-propanol In a similar manner to that described in Example 50-(ii), a reaction was carried out by using 1-(6-fluoromethyloxynaphthalen-2-yl)-2-methyl-1-(1-trityl-1H-imidazol-4-yl)-1-propanol (1.40 g) to give the titled compound (470 mg) as a colorless powder.

$^1$H-NMR (CDCl$_3$+CD$_3$OD) δ: 0.80 (3H, d, J=6.8 Hz), 1.01 (3H, d, J=6.8 Hz), 2.65–2.78 (1H, m), 5.69 (1H, s), 5.96 (1H, s), 7.00 (1H, d, J=1.2 Hz), 7.23 (1H, dd, J=2.5, 8.9 Hz), 7.42 (1H, d, J=2.2 Hz), 7.51 (1H, s), 7.58 (1H, dd, J=1.8, 8.6 Hz), 7.71 (1H, d, J=8.8 Hz), 7.80 (1H, d, J=8.8 Hz), 7.97 (1H, s). IR (KBr): 3171, 3140, 2980, 1082, 1030, 968, 860, 810 cm$^{-1}$.

EXAMPLE 49

Production of 1-[5,7-Dimethyl-6-methoxynaphthalen-2-yl]-1-(1H-imidazol-4-yl)-2-methyl-1-propanol (i) Production of 5-Bromo-1,3-dimethyl-2-methoxybenzene In a similar manner to that described in Example 44-(i), a reaction was carried out by using 4-bromo-2,6-dimethylphenol (80.30 g) to give the titled compound (75.01 g) as an oil.

$^1$H-NMR (CDCl$_3$) δ: 2.25 (6H, s), 3.69 (3H, s), 7.14 (2H, s). IR (KBr): 2940, 1474, 1219, 1171, 1015, 858, 851 cm$^{-1}$.

(ii) Production of 3,5-Dimethyl-4-methoxybenzaldehyde 5-Bromo-1,3-dimethyl-2-methoxybenzene (70.10 g) was dissolved in THF (700 ml). The solution was cooled to −78° C. To the reaction mixture was added dropwise n-butyl lithium in hexane (1.62 M, 250 ml), and the mixture was stirred for 15 min. To the mixture was added DMF (50 ml), and the temperature of the mixture was elevated to 0° C. To the reaction mixture was added an aqueous solution of ammonium chloride and ethyl acetate, and the mixture was extracted with ethyl acetate. The organic layer was dried and concentrated. To the residue was added ethyl acetate. The organic layer was washed with water and saturated solution of sodium chloride, dried and concentrated to give the titled compound (52.80 g) as an oil.

$^1$H-NMR (CDCl$_3$) δ: 2.35 (6H, s), 3.78 (3H, s), 7.56 (2H, s), 9.88 (1H, s). IR (KBr): 2928, 1694, 1302, 1134, 1011 cm$^{-1}$.

(iii) Production of Ethyl 5,7-Dimethyl-6-methoxy-2-naphthoate

In a similar manner to that described in Example 38-(i), a reaction was carried out by using 3,5-dimethyl-4-methoxybenzaldehyde (49 g) to give the titled compound (58.01 4 g) as an oil.

$^1$H-NMR (CDCl$_3$) δ: 1.43 (3H, t, J=7.1 Hz), 2.45 (3H, s), 2.59 (3H, s), 3.78 (3H, s), 4.42 (2H, q, J=7.1 Hz), 7.60 (1H, s), 7.90 (1H, d, J=8.8 Hz), 8.01 (1H, dd, J=1.4, 8.8 Hz), 8.46 (1H, d, J=1.4 Hz). IR (KBr): 2940, 1717, 1466, 1254, 1238, 1101 cm$^{-1}$.

(iv) Production of (5,7-Dimethyl-6-methoxynaphthalen-2-yl)methanol

In a similar manner to that described in Example 38-(ii), a reaction was carried out by using ethyl 6-methoxy-5,7-dimethyl-2-naphthoate (57.01 g) to give the titled compound (18.23 g) as an oil.

$^1$H-NMR (CDCl$_3$) δ: 2.44 (3H, s), 2.58 (3H, s), 3.78 (3H, s), 4.80 (2H, s), 7.42 (1H, m), 7.47 (1H, brs), 7.65 (1H, brs), 7.98 (1H, d, J=8.8 Hz). IR (KBr): 3277, 2942, 1468, 1238, 1119, 1057, 1003 cm$^{-1}$.

(v) Production of 5,7-Dimethyl-6-methoxy-2-naphthoaldehyde

In a similar manner to that described in Example 1-(ii), a reaction was carried out by using (6-methoxy-5,7-dimethylnaphthalen-2-yl)methanol (13.30 g) to give the titled compound (9.50 g) as a colorless solid.

$^1$H -NMR (CDCl$_3$) δ: 2.49 (3H, d, J=0.8 Hz), 2.63 (3H, s), 3.8 2 (3H, s), 7.68 (1H, s), 7.90 (1H, dd, J=1.8, 8.8 Hz), 8.01 (1H, dd, J=0.8, 8.8 Hz), 8.21 (1H, d, J=1.8 Hz), 10.13 (1H, s). IR (KBr): 1694, 1466, 1227, 1157 cm$^{-1}$.

(vi) Production of (1H-Imidazol-4-yl)(5,7-dimethyl-6-methoxynaphthalen-2-yl)methanol In a similar manner to that described in Example 20-(i), a reaction was carried out by using 5,7-dimethyl-6-methoxy-2-naphthoaldehyde (5.00 g) to give the titled compound (3.61 g) as a colorless solid.

$^1$H-NMR (CDCl$_3$) δ: 2.29 (3H, s), 2.44 (3H, s), 3.68 (3H, s), 5.79 (1H, s), 6.41 (1H, s), 7.15 (1H, s), 7.20–7.35 (2H, m), 7.58 (1H, s), 7.64 (1H, d, J=8.8 Hz). IR (KBr): 2936, 1470, 1236, 1057 cm$^{-1}$.

(vii) Production of 1H-Imidazol-4-yl-(5,7-dimethyl-6-methoxynaphthalen-2-yl)methanone In a similar manner to that described in Example 1-(ii), a reaction was carried out by using (1H-imidazol-4-yl)(5,7-dimethyl-6-methoxynaphthalen-2-yl)methanol (200 mg) to give the titled compound (127 mg) as a colorless solid.

$^1$H-NMR (CDCl$_3$) δ: 2.50 (3H, s), 2.65 (3H, s), 3.83 (3H, s), 7.68 (1H, s), 7.84 (1H, s), 7.89–8.08 (3H, m), 8.41 (1H, brs). IR (KBr): 2996, 1645, 1165, 868 cm$^{-1}$.

(viii) Production of 1-(1H-Imidazol-4-yl)-1-[5,7-dimethyl-6-methoxynaphthalen-2-yl]-2-methyl-1-propanol In a similar manner to that described in Example 1-(iv), a reaction was carried out by using (1H-imidazol-4-yl)(5,7-dimethyl-6-methoxynaphthalen-2-yl)methanone (104 mg) to give the titled compound (62 mg) as a colorless solid.

$^1$H-NMR (CDCl$_3$) δ: 0.80 (3H, d, J=6.9 Hz), 1.00 (3H, d, J=6.9 Hz), 2.43 (3H, s), 2.57 (3H, s), 2.60–2.80 (1H, m), 3.76 (3H, s), 6.96 (1H, d, J=1.0 Hz), 7.44 (1H, d, J=1.0 Hz), 7.50 (1H, s), 7.55 (1H, dd, J=1.8, 9.0 Hz), 7.83 (1H, d, J=9.0 Hz), 7.91 (1H, d, J=1.8 Hz). IR (KBr): 2969, 1468, 1236, 1003, 909, 735 cm$^{-1}$.

EXAMPLE 50

Production of 1-(6-Bromonaphthalen-2-yl)-1-(1H-imidazol-4-yl)-2-methyl-1-propanol (i) Production of 2,6-Dibromonaphthalene To a solution of triphenylphosphine (64.5 g) in acetonitrile (150 ml) was added dropwise bromine (39 g) under ice cooling, and the mixture was stirred at room temperature for 30 min. To the mixture was added a solution of 6-bromo-2-naphthol (50.0 g) in acetonitrile (100 ml). The mixture was stirred at 70° C. for 2 h. The solvent was distilled off, and the residue was heated at 250° C. for 5 h. The obtained black solid was dissolved in dichloromethane, washed with 1N-sodium hydroxide solution and dried. The solvent was distilled off, and to the residue was added methanol (50 ml). The mixture was subjected to filtration and the residue was washed with methanol. The resulting solid was purified by column chromatography (eluent, hexane:THF=1:1), then recrystallized from ethyl acetate to give the titled compound (17.5 g) as brown plates.

$^1$H-NMR (CDCl$_3$) δ: 7.51–7.62 (4H, m), 7.94 (2H, s). IR (KBr): 1769, 1568, 1481, 1175, 1134, 1065, 964, 885, 853, 816 cm$^{-1}$.

(ii) Production of 1-(6-Bromonaphthalen-2-yl)-2-methyl-1-(1-trityl-1H-imidazol-4-yl)-1-propanol 2,6-Dibromonaphthalene (25.0 g) was dissolved in THF (1250 ml). The solution was cooled to −50° C. To the solution was slowly added a solution of n-butyllithium in hexane (1.6 M; 57 ml), and the mixture was stirred at −50° C. for 20 min. To the mixture was added dropwise a solution of 4-formyl-1-trityl-1H-imidazole (22.2 g) in THF (200 ml). The mixture was stirred at 50° C. for 20 min. To the mixture was added water, and the organic layer was separated. The aqueous layer was extracted with ethyl acetate. The organic layers were combined, dried and concentrated. The residue was purified by silica gel chromatography (eluent, hexane:THF=1:1), and recrystallized from hexane-THF to give the titled compound (31.2 g) as a pale brown powder.

$^1$H-NMR (CDCl$_3$+CD$_3$OD) δ: 0.72 (3H, d, J=6.7 Hz), 0.95 (3H, d, J=6.7 Hz), 2.45–2.58 (1H, m), 3.75 (1H, s), 6.80 (1H, d, J=1.4 Hz), 7.10–7.15 (6H, m), 7.29–7.35 (10H, m), 7.50 (1H, dd, J=1.8, 8.8 Hz), 7.57 (1H, dd, J=1.8, 8.8 Hz), 7.63–7.69 (2H, m), 7.94 (1H, d, J=1.8 Hz), 8.02 (1H, s). IR (KBr): 3241, 2967, 1493, 1445, 1169, 1017, 826, 812, 756, 747, 700 cm$^{-1}$.

(iii) Production of 1-(6-Bromonaphthalen-2-yl)-1-(1H-imidazol-4-yl)-2-methyl-1-propanol 1-(6-Bromonaphthalen-2-yl)-2-methyl-1-(1-trityl-1H-imidazol-4-yl)-1-propanol (1.0 g) and pyridine hydrochloride (390 mg) were dissolved in methanol (8 ml). The solution was stirred at 60° C. for 2 h. The solution was cooled and neutralized with saturated aqueous solution of sodium hydrogencarbonate. The solvent was distilled off and the residue was filtered and washed with ethanol. The filtrate was concentrated, and the residue was purified by silica gel column chromatography (eluent, dichloromethane:methanol=30:1→10:1), then recrystallized from ethyl acetate to give the titled compound (454 mg) as a colorless powder.

$^1$H-NMR (CDCl$_3$+CD$_3$OD) δ: 0.79 (3H, d, J=6.8 Hz), 1.0 (3H, d, J=6.8 Hz), 2.68–2.82 (1H, m), 7.02 (1H, d, J=1.2 Hz), 7.49–7.54 (2H, m), 7.63 (1H, dd, J=1.8, 8.8 Hz) 7.69 (1H, d, J=8.8 H), 7.72 (1H, d, J=8.8 Hz), 7.96 (1H, d, J=2.0 Hz), 8.01 (1H, s). IR (KBr): 3225, 2965, 1383, 1165, 1134, 10.15, 887, 816, 760 cm$^{-1}$.

EXAMPLE 51

Production of 1-(6-Aminonaphthalen-2-yl)-1-(1H-imidazol-4-yl)-2-methyl-1-propanol (i) Production of 1-{6-[(Diphenylmethylene)amino]naphthalen-2-yl}-2-methyl-1-(1-trityl-1H-imidazol-4-yl)-1-propanol 1-(6-Bromonaphthalen-2-yl)-2-methyl-1-(1-trityl-1H-imidazol-4-yl)-1-propanol (14.0 g), benzophenonimine (5.18 g), tris(dibenzylideneacetone)dipalladium (440 mg), (R)-(+)-2,2'-bis(diphenylphosphino)-1,1'-binaphthyl (872 mg) and sodium t-butoxide (5.72 g) were dissolved in toluene (140 ml). The solution was stirred at 80° C. for 18 h under argon atmosphere. The solution was cooled, and diluted with ethyl acetate. The mixture was filtered with celite, the residue was washed with ethyl acetate. The filtrate was concentrated and the residue was purified by silica gel chromatography (eluent, hexane:THF=1:1), then recrystallized from hexane-THF (4:1) to give the titled compound (14.3 g) as a yellow powder.

$^1$H-NMR (CDCl$_3$) δ: 0.74 (3H, d, J=6.7 Hz), 0.93 (3H, d, J=6.7 Hz), 2.42–2.56 (1H, d), 3.65 (1H, br s), 6.79 (1H, d, J=1.4 Hz), 6.87 (1H, dd, J=2.0, 8.6 Hz), 7.10–7.57 (28H, m), 7.76 (1H, d, J=2.0 Hz), 7.80 (1H, d, J=1.4 Hz), 7.86 (1H, s). IR (KBr): 3453, 2969, 1493, 1445, 1256, 1163, 1005, 812, 748 cm$^{-1}$.

(ii) Production of 1-(6-Aminonaphthalen-2-yl)-2-methyl-1-(1-trityl-1H-imidazol-4-yl)-1-propanol 1-{6-[(Diphenylmethylene)amino]naphthalen-2-yl}-2-methyl-1-(1-trityl-1H-imidazol-4-yl)-1-propanol (1.0 g) was dissolved in THF (5 ml)-methanol (5 ml). To the solution were added sodium acetate (285 mg) and hydroxylamine hydrochloride (181 mg), and the mixture was stirred at room temperature for 20 min. To the mixture was added 0.1N-aqueous solution of sodium hydroxide, and the mixture was extracted with ethyl acetate, washed with saturated sodium chloride solution and dried. The solvent was distilled off and the residue was purified by silica gel chromatography (eluent, hexane:ethyl acetate=2:1→1:1) to give the titled compound (720 mg) as a pale red powder.

$^1$H-NMR (CDCl$_3$) δ: 0.75 (3H, d, J=6.8 Hz), 0.93 (3H, d, J=6.8 Hz), 2.44–2.57 (1H, m), 3.62 (1H, br s), 6.79 (1H, d, J=1.4 Hz), 6.89–6.94 (2H, m), 7.11–7.18 (6H, m), 7.29–7.36 (10H, m), 7.44 (1H, dd, J=1.8, 8.8 Hz), 7.50 (1H, d, J=8.8 Hz), 7.61 (1H, d, J=8.4 Hz), 7.86 (1H, d, J=1.2 Hz). IR (KBr): 3596, 3571, 3370, 3092, 2963, 1634, 1485, 1445, 1001, 852, 760, 747 cm$^{-1}$.

(iii) Production of 1-(6-Aminonaphthalen-2-yl)-1-(1H-imidazol-4-yl)-2-methyl-1-propanol In a similar manner to that described in Example 50-(iii), a reaction was carried out by using 1-(6-aminonaphthalen-2-yl)-2-methyl-1-(1-trityl-1H-imidazol-4-yl)-1-propanol (560 mg) to give the titled compound (120 mg) as a pale red powder.

$^1$H-NMR (CDCl$_3$) δ: 0.81,(3H, d, J=6.7 Hz), 0.99 (3H, d, J=6.7 Hz), 2.63–2.76 (1H, m), 6.92–6.97 (3H, m), 7.44 (1H, dd, J=1.8, 8.8 Hz), 7.49–7.54 (2H, m), 7.63 (1H, d, J=8.6 Hz), 7.82 (1H, s). IR (KBr): 3200, 2967, 1636, 1609, 1508, 1483, 1387, 1294, 1177, 1005, 856, 814 cm$^{-1}$.

EXAMPLE 52

Production of N-{6-[1-Hydroxy-1-(1H-imidazol-4-yl)-2-methylpropyl]naphthalen-2-yl}acetamide (i) Production of N-{6-[1-Hydroxy-2-methyl-1-(1-trityl-1H-imidazol-4-yl)propyl]naphthalen-2-yl}acetamide In a similar manner to that described in Example 51-(ii), a reaction was carried out by using 1-{6-[(diphenylmethylene)amino]naphthalen-2-yl}-2-methyl-1-(1-trityl-1H-imidazol-4-yl)-1-propanol (15.0 g) to give 1-(6-aminonaphthalen-2-yl)-2-methyl-1-(1-trityl-1H-imidazol-4-yl)-1-propanol as a pale yellow oily substance. The product was dissolved in dichloromethane (100 ml). To the solution were added pyridine (5.3 ml) and acetic anhydride (4.1 ml), and the mixture was stirred at room temperature for 40 min. To the mixture was added saturated solution of sodium hydrogencarbonate, and the mixture was extracted with dichloromethane and dried, and the solvent was distilled off. The residue was recrystallized from ethyl acetate to give the titled compound (11.6 g) as pale red crystals.

$^1$H-NMR (CDCl$_3$+CD$_3$OD) δ: 0.75 (3H, d, J=6.7 Hz), 0.95 (3H, d, J=6.7 Hz), 2.20 (3H, s), 2.57–2.71 (1H, m), 6.87 (1H, d, J=1.4 Hz), 7.10–7.15 (6H, m), 7.32–7.54 (12H, m), 7.68–7.77 (2H, m), 7.92 (1H, s), 8.15 (1H, s), 9.60 (1H, br s). IR (KBr): 3058, 2969, 1686, 1611, 1547, 1493, 1445, 1298, 1011, 766, 747, 700 cm$^{-1}$.

(ii) Production of N-{6-[1-Hydroxy-1-(1H-imidazol-4-yl)-2-methylpropyl]naphthalen-2-yl}acetamide In a similar manner to that described in Example 50-(iii), a reaction was carried out by using N-{6-[1-hydroxy-2-methyl-1-(1-trityl-1H-imidazol-4-yl)propyl]naphthalen-2-yl}acetamide (11.5 g) to give the titled compound (5.52 g) as a pale red powder.

$^1$H-NMR (CDCl$_3$+CD$_3$OD) δ: 0.79 (3H, d, J=6.8 Hz), 1.0 (3H, d, J=6.8 Hz), 2.17 (3H, s), 2.63–2.76 (1H, m), 6.99 (1H, s), 7.43–7.54 (3H, m), 7.65–7.74 (2H, m), 7.91 (1H, s), 8.11 (1H, s). IR (KBr): 3248, 2971, 1669, 1609, 1586, 1557, 1495, 1391, 1296, 818 cm$^{-1}$.

EXAMPLE 53

Production of N'-{6-[1-Hydroxy-1-(1H-imidazol-4-yl)-2-methylpropyl]naphthalen-2-yl}-N,N-dimethylurea (i) Production of N'-{6-[1-Hydroxy-2-methyl-1-(1-trityl-1H-imidazol-4-yl)propyl]naphthalen-2-yl}-N,N-dimethylurea In a similar manner to that described in Example 51-(ii), a reaction was carried out by using 1-{6-[(diphenylmethylene)amino]naphthalen-2-yl}-2-methyl-1-(1-trityl-1H-imidazol-4-yl)-1-propanol (3.0 g) to give a crude 1-(6-aminonaphthalen-2-yl)-2-methyl-1-(1-trityl-1H-imidazol-4-yl)-1-propanol as a pale yellow oil. The product was dissolved in THF (10 ml). To the solution were added pyridine (1.06 ml) and p-nitrophenyl chlorocarbonate (1.76 g) under ice cooling, and the mixture was stirred for 20 min. To the mixture was added water, and the mixture was washed with ethyl acetate and saturated sodium chloride solution and dried. And the solvent was distilled off. The residue was purified by column chromatography (eluent, ethyl acetate:hexane=2:1), then recrystallized from ethyl acetate-hexane (2:1) to give p-nitrophenylcarbamate compound (1.30 g).

p-Nitrophenylcarbamate compound (1.20 g) was dissolved in DMF (8 mL). To the solution were added triethylamine (0.73 mL) and dimethylamine hydrochloride (284 mg), and the mixture was stirred at room temperature for 1 h. To the mixture was added 0.1N-aqueous solution of sodium hydroxide, and the mixture extracted with ethyl acetate, and washed with 0.3N aqueous solution of sodium hydroxide, water and saturated sodium chloride solution, successively, and dried. The solvent was distilled off and the residue was purified by column chromatography (eluent, ethyl acetate), and recrystallized from ethyl acetate-hexane (1:1) to give the titled compound (745 mg) as a colorless powder.

$^1$H-NMR (CDCl$_3$) δ: 0.74 (3H, d, J=6.6 Hz), 0.94 (3H, d, J=6.6 Hz), 2.44–2.57 (1H, m), 3.06 (6H, s), 3.70 (1H, br s), 6.46 (1H, s), 6.79 (1H, d, J=1.2 Hz), 7.10–7.15 (6H, m), 7.29–7.38 (11H, m), 7.48 (1H, dd, J=1.4, 8.8 Hz), 7.64 (1H, d, J=9.2 Hz), 4.69 (1H, d, J=8.8 Hz), 7.93 (2H, s). IR (KBr): 3368, 2969, 1672, 1609, 1541, 1493, 1385, 1291, 1192, 758, 743, 700 cm$^{-1}$.

(ii) Production of N'-{6-[1-Hydroxy-1-(1H-imidazol-4-yl)-2-methylpropyl]naphthalen-2-yl}-N,N-dimethylurea In a similar manner to that described in Example 50-(iii), a reaction was carried out by using N'-{6-[1-hydroxy-2-methyl-1-(1-trityl-1H-imidazol-4-yl)propyl]naphthalen-2-yl}-N,N-dimethylurea (650 mg) to give the titled compound (246 mg) as a colorless powder.

$^1$H-NMR (CDCl$_3$+CD$_3$OD) δ: 0.80 (3H, d, J=6.8 Hz), 1.00 (3H, d, J=6.8 Hz), 2.67–2.80 (1H, m), 3.06 (6H, s), 7.01 (1H, d, J=1.2 Hz), 7.46 (1H, dd, J=2.2, 8.8 Hz), 7.51–7.56 (2H, m), 7.66 (1H, d, J=8.6 Hz), 7.74 (1H, d, J=8.8 Hz), 7.83 (1H, d, J=1.8 Hz), 7.92 (1H, d, J=1.0 Hz). IR (KBr): 3200, 2969, 1649, 1535, 1493, 1406, 1387, 1364, 1227, 1194, 814 cm$^{-1}$.

EXAMPLE 54

Production of N-{6-[1-Hydroxy-1-(1H-imidazol-4-yl)-2-methylpropyl]naphthalen-2-yl}-N'-methylurea 1-(6-Aminonaphthalen-2-yl)-2-methyl-1-(1-trityl-1H-imidazol-4-yl)-1-propanol (1.40 g) was dissolved in THF (10 ml). To the solution were added pyridine (0.65 ml) and phenyl chlorocarbonate (0.50 ml) under ice cooling, and the mixture was stirred for 30 min. The reaction mixture was poured into phosphate buffer solution (pH 7.0), and the mixture was extracted with ethyl acetate, washed with saturated sodium chloride solution and dried. The solvent was distilled off to give phenylcarbamate compound as a red oil.

The obtained phenylcarbamate compound was dissolved in DMSO (5 ml). To the solution were added methylamine hydrochloride (360 mg) and 10N-aqueous solution of sodium hydroxide (0.54 ml), and the mixture was stirred at room temperature for 1 h. To the mixture was added 0.5N-aqueous solution of sodium hydroxide, and the mixture was extracted with ethyl acetate, washed with 0.5N-aqueous solution of sodium hydroxide and saturated sodium chloride solution, successively, and dried. The solvent was distilled off and the residue was purified by column chromatography (eluent, hexane:ethyl acetate=1:2→1:4) to give N-{6-[1-hydroxy-2-methyl-1-(1-trityl-1H-imidazol-4-yl)propyl]naphthalen-2-yl}-N'-methylurea (984 mg) as a pale yellow powder. In a similar manner to that described in Example 50-(iii), a reaction was carried out by using the product (850 mg) to give the titled compound (278 mg) as a pale red powder.

$^1$H-NMR (CDCl$_3$+CD$_3$OD) δ: 0.79 (3H, d, J=6.9 Hz), 0.97 (3H, d, J=6.9 Hz), 2.74–2.87 (1H, m), 2.79 (3H, s), 7.03 (1H, s), 7.38 (1H, dd, J=2.2, 8.8 Hz), 7.55–7.66 (3H, m), 7.72 (1H, d, J=9.0 Hz), 7.87 (1H, d, J=2.0 Hz), 7.94 (1H, s). IR (KBr): 3320, 2971, 1655, 1555, 1493, 1387, 1341, 1296, 1248, 814 cm$^{-1}$.

EXAMPLE 55

Production of N-{6-[1-Hydroxy-1-(1H-imidazol-4-yl)-2-methylpropyl]naphthalen-2-yl}methanesulfonamide (i) Production of N-{6-[1-Hydroxy-2-methyl-1-(1-trityl-1H-imidazol-4-yl)propyl]naphthalen-2-yl}methanesulfonamide In a similar manner to that described in Example 51-(ii), a reaction was carried out by using 1-{6-[(diphenylmethylene)amino]naphthalen-2-yl}-2-methyl-1-(1-trityl-1H-imidazol-4-yl)-1-propanol (2.0 g) to give crude product containing 1-(6-aminonaphthalen-2-yl)-2-methyl-1-(1-trityl-1H-imidazol-4-yl)-1-propanol as a pale yellow oily substance. The crude product was dissolved in dichloromethane (10 ml). To the solution were added pyridine (0.71 ml) and methanesulfonyl chloride (0.34 ml) under ice cooling, and the mixture was stirred for 30 min. To the mixture was added 0.1N-aqueous solution of sodium hydroxide, and the mixture was extracted with ethyl acetate, washed with saturated sodium chloride solution and dried. The solvent was distilled off. The residue was purified by column chromatography (eluent, hexane:ethyl acetate=1:1) to give the titled compound (1.16 g) as a pale yellow powder.

$^1$H-NMR (CDCl$_3$) δ: 0.72 (3H, d, J=6.7 Hz), 0.98 (3H, d, J=6.7 Hz), 2.43–2.57 (1H, m), 3.02 (3H, s), 3.70 (s, 1H), 6.84 (1H, d, J=1.4 Hz), 7.02 (1H, dd, J=2.2, 8.8 Hz), 7.12–7.19 (6H, m), 7.31–7.40 (10H, m), 7.45 (1H, dd, J=1.7, 8.7 Hz), 7.51–7.61 (3H, m), 7.91 (2H, s). IR (KBr): 3505, 3248, 3148, 2969, 1491, 1447, 1343, 1319, 1152, 978, 747, 702 cm$^{-1}$.

(ii) Production of N-{6-[1-Hydroxy-1-(1H-imidazol-4-yl)-2-methylpropyl]naphthalen-2-yl}methanesulfonamide In a similar manner to that described in Example 50-(iii), a reaction was carried out by using N-{6-[1-hydroxy-2-methyl-1-(1-trityl-1H-imidazol-4-yl)propyl]naphthalen-2-yl}methanesulfonamide (900 mg) to give the titled compound (385 mg) as a colorless powder.

$^1$H-NMR (CDCl$_3$+CD$_3$OD) δ: 0.78 (3H, d, J=6.8 Hz), 1.00 (3H, d, J=6.8 Hz), 1.84–1.90 (1H, m), 2.97 (3H, s), 6.98 (1H, s), 7.28 (1H, dd, J=1.9, 8.7 Hz), 7.50 (1H, d, J=1.0 Hz), 7.55 (1H, dd, J=1.7, 8.7 Hz), 7.62–7.69 (2H, m), 7.74 (1H, d, J=8.7 Hz), 7.95 (1H, s). IR (KBr): 3214, 2969, 1607, 1481, 1379, 1341, 1308, 1150, 980 cm$^{-1}$.

EXAMPLE 56

Production of 1-(6-Hydroxymethylnaphthalen-2-yl)-1-(1H-imidazol-4-yl)2-methyl-1-propanol (i) Production of 6-[1-Hydroxy-2-methyl-1-(1-trityl-1H-imidazol-4-ylpropyl]-2-naphthoaldehyde 1-(6-Bromonaphthalen-2-yl)-2-methyl-1-(1-trityl-1H-imidazol-4-yl)-1-propanol (5.0 g) was dissolved in THF (100 ml), and was cooled to −70° C. To the solution was slowly added a solution of n-butyllithium in hexane (1.6 M; 11.7 ml), and the mixture was stirred at −70° C. for 20 min. To the mixture was added dropwise a solution of 4-formylmorpholine (1.96 g) in THF (10 ml), and the mixture was stirred for 30 min. To the mixture was added water, the mixture was extracted with ethyl acetate, washed with saturated sodium chloride solution and dried. The solvent was distilled off and the residue was purified by column chromatography (eluent, hexane:THF=4:1→2:1), followed by recrystallization from hexane-THF (6:1) to give the titled compound (2.69 g) as a pale yellow powder.

$^1$H-NMR (CDCl$_3$) δ: 0: 0.74 (3H, d, J=6.8 Hz), 0.97 (3H, d, J=6.8 Hz), 2.48–2.62 (1H, m), 3.79 (1H, br s), 6.83 (1H, d, J=1.4 Hz), 7.10–7.17 (6H, m), 7.30–7.36 (10H, m), 7.70 (1H, dd, J=1.7, 8.7 Hz), 7.85–7.96 (3H, m), 8.11 (1H, d, J=1.6 Hz), 8.29 (1H, s), 10.14 (1H, s). IR (KBr): 3256, 2971, 1694, 1628, 1474, 1447, 1161, 1128, 1009, 768, 747, 702 cm$^{-1}$.

(ii) Production of 1-(6-Hydroxymethylnaphthalen-2-yl)-2-methyl-1-(1-trityl-1H-imidazol-4-yl)-1-propanol 6-[1-Hydroxy-2-methyl-1-(1-trityl-1H-imidazol-4-ylpropyl]-2-naphthoaldehyde (800 mg) was dissolved in THF (6 ml) ethanol (12 ml). To the solution was added sodium borohydride (56 mg). The mixture was stirred at room temperature for 30 min. To the mixture was added water, and the mixture was extracted with ethyl acetate, washed with saturated sodium chloride solution and dried. The solvent was distilled off and the residue was purified by column chromatography (eluent, hexane:THF=2:1→1:1) to give the titled compound (558 mg) as a colorless powder.

$^1$H-NMR (CDCl$_3$) δ: 0.73 (3H, d, J=6.9 Hz), 0.96 (3H, d, J=6.9 Hz), 2.47–2.61 (1H, m), 3.75 (1H, s), 3.92 (1H, s), 4.82 (2H, s), 6.81 (1H, d, J=1.6 Hz), 7.09–7.16 (6H, m), 7.29–7.38 (10H, m), 7.43 (1H, dd, J=1.6, 8.4 Hz), 7.55 (1H, dd, J=1.8, 8.6 Hz), 7.69–7.80 (3H, m), 8.00 (1H, s). IR (KBr): 3058, 2969, 1493, 1445, 1159, 1130, 1036, 1009, 820, 747, 702 cm$^{-1}$.

(iii) Production of 1-(6-Hydroxymethylnaphthalen-2-yl)-1-(1H-imidazol-4-yl)-2-methyl-1-propanol In a similar manner to that described in Example 50-(iii), a reaction was carried out by using 1-(6-hydroxymethylnaphthalen-2-yl)-2-methyl-1-(1-trityl-1H-imidazol-4-yl)-1-propanol (500 mg) to give the titled compound (232 mg) as a colorless powder.

$^1$H-NMR (CDCl$_3$+CD$_3$OD) δ: 0.79 (3H, d, J=6.7 Hz), 1.00 (3H, d, J=6.7 Hz), 2.66–2.79 (1H, m), 4.77 (2H, s), 7.00 (1H, s), 7.44 (1H, dd, J=1.6, 8.4 Hz), 7.49 (1H, s), 7.57 (1H, dd, J=1.8, 8.6 Hz), 7.71–7.74 (2H, m), 7.80 (1H, d, J=8.4 Hz), 7.98 (1H, m). IR (KBr): 3200, 2971, 1466, 1385, 1364, 1157, 1128, 1013, 893, 860, 818, 743 cm$^{-1}$.

EXAMPLE 57

Production of 1-{6-[1-Hydroxy-1-(1H-imidazol-4-yl)-2-methylpropyl]naphthalen-2-yl}-1-ethanone (i) Production of 1-{6-[1-Hydroxy-2-methyl-1-(1-trityl-1H-imidazol-4-yl)propyl]naphthalen-2-yl}-1-ethanone 1-(6-Bromonaphthalen-2-yl)-2-methyl-1-(1-trityl-1H-imidazol-4-yl)-1-propanol (7.0 g) was dissolved in THF (150 ml). The solution was cooled to −70° C. To the mixture was slowly added a solution of n-butyl lithium in hexane (1.6 M; 16.4 ml), and the mixture was stirred at −70° C. for 20 min. To the mixture was added dropwise a solution of N-methyl-N-methoxyacetamide (2.45 g) in THF (10 ml), and the mixture was stirred at −70° C. for 20 min. To the mixture was added water, and the mixture was extracted with ethyl acetate, washed with saturated sodium chloride solution and dried. The solvent was distilled off and the residue was purified column chromatography (eluent, hexane:THF=6:1→3:1) to give the titled compound (3.53 g) as a colorless powder.

$^1$H-NMR (CDCl$_3$) δ: 0.74 (3H, d, J=6.8 Hz), 0.97 (3H, d, J=6.8 Hz), 2.48–2.61 (1H, m), 2.72 (3H, s), 3.75 (1H, br s), 6.83 (1H, d, J=1.4 Hz), 7.10–7.17 (6H, m), 7.30–7.37 (10H, m), 7.65 (1H, dd, J=1.6, 8.8 Hz), 7.84 (1H, d, J=8.8 Hz), 7.87 (1H, d, J=8.8 Hz), 8.01 (1H, dd, J=1.6, 8.8 Hz), 8.07 (1H, s), 8.42 (1H, s). IR (KBr): 3519, 2963, 1671, 1480, 1445, 1360, 1275, 1265, 1231, 1190, 1157, 1140 cm$^{-1}$.

(ii) Production of 1-{6-[1-Hydroxy-1-(1H-imidazol-4-yl)-2-methylpropyl]naphthalen-2-yl}-1-ethanone In a similar manner to that described in Example 50-(iii), a reaction was carried out by using 1-{6-[1-hydroxy-2-methyl-1-(-1-trityl-1H-imidazol-4-yl)propyl]naphthalen-2- yl}-1-ethanone (350 mg) to give the titled compound (159 mg) as a colorless powder.

$^1$H-NMR (CDCl$_3$+CD$_3$OD) δ: 0.81 (3H, d, J=6.7 Hz), 1.02 (3H, d, J=6.7 Hz), 2.73–2.86 (4H, m), 7.05 (1H, d, J=1.1 Hz), 7.56 (1H, d, J=1.1 Hz), 7.73 (1H, dd, J=1.7, 8.7 Hz), 7.89 (1H, d, J=8.7 Hz), 7.92 (1H, d, J=8.7 Hz), 7.99 (1H, dd, J=1.7, 8.7 Hz), 8.11 (1H, s), 8.46 (1H, s). IR (KBr): 3235, 2969, 1672, 1306, 1289, 1044, 895, 824, 789 cm$^{-1}$.

EXAMPLE 58

Production of 1-{6-[1-Hydroxy-1-(1H-imidazol-4-yl)-2-methylpropyl]naphthalen-2-yl}-1-propanone (i) Production of 1-{6-[1-Hydroxy-2-methyl-1-(1-trityl-1H-imidazol-4-yl)propyl]naphthalen-2-yl}-1-propanone In a similar manner to that described in Example 60-(i), the reaction of 1-(6-bromonaphthalen-2-yl)-2-methyl-1-(1-trityl-1H-imidazol-4-yl)-1-propanol (2.0 g) with N,N-dimethylpropionamide (688 mg) was carried out to give the titled compound (824 mg) as a colorless powder.

$^1$H-NMR (CDCl$_3$) δ: 0.74 (3H, d, J=6.7 Hz), 0.97 (3H, d, J=6.7 Hz), 1.28 (3H, t, J=7.3 Hz), 2.48–2.61 (1H, m), 3.14 (2H, q, J=7.3 Hz), 3.75 (1H, s), 6.82 (1H, d, J=1.2 Hz), 7.11–7.17 (6H, m), 7.30–7.35 (10H, m), 7.65 (1H, dd, J=1.6, 8.6 Hz), 7.84 (1H, d, J=8.6 Hz), 7.86 (1H, d, J=8.6 Hz), 8.02 (1H, dd, J=1.6, 8.6 Hz), 8.07 (1H, s), 8.44 (1H, s). IR (KBr): 3214, 2971, 1686, 1495, 1476, 1445, 1383, 1167, 1013, 828, 810, 762 cm$^{-1}$.

(ii) Production of 1-{6-[1-Hydroxy-1-(1H-imidazol-4-yl)-2-methylpropyl]naphthalen-2-yl}-1-propanone In a similar manner to that described in Example 50-(iii), a reaction was carried out by using 1-{6-[1-hydroxy-2-methyl-1-(1-trityl-1H-imidazol-4-yl)-propyl]naphthalen-2-yl}-1-propanone (700 mg) to give the titled compound (278 mg) as a colorless powder.

$^1$H-NMR (CDCl$_3$+CD$_3$OD) δ: 0.80 (3H, d, J=6.7 Hz), 1.02 (3H, d, J=6.7 Hz), 1.27 (3H, t, J=7.2 Hz), 2.70–2.83 (1H, m), 3.15 (2H, q, J=7.2 Hz), 7.03 (1H, d, J=1.2 Hz), 7.53 (1H, s), 7.69 (1H, dd, J=1.7, 8.8 Hz), 7.87–7.90 (2H, m), 8.00 (1H, dd, J=1.7, 8.6 Hz), 8.08 (1H, s), 8.77 (1H, s). IR (KBr): 3175, 2976, 1684, 1476, 1460, 1433, 1385, 1372, 1348, 1032, 901, 818 cm$^{-1}$.

EXAMPLE 59

Production of 1-{6-[1-Hydroxy-1-(1H-imidazol-4-yl)-2-methylpropyl]naphthalen-2-yl}-2-methyl-1-propanone (i) Production of 1-{6-[1-Hydroxy-2-methyl-1-(1-trityl-1H-imidazol-4-yl)propyl]naphthalen-2-yl}-2-methyl-1-propanone In a similar manner to that described in Example 57-(i), the reaction of 1-(6-bromonaphthalen-2-yl)-2-methyl-1-(1-trityl-1H-imidazol-4-yl)-1-propanol (2.0 g) with 2-methyl-1-(4-morpholinyl)-1-propanone (688 mg) was carried out to give the titled compound (966 mg) as a colorless powder.

$^1$H-NMR (CDCl$_3$) δ: 0.74 (3H, d, J=6.8 Hz), 0.97 (3H, d, J=6.8 Hz), 1.27 (6H, d, J=6.8 Hz), 2.48–2.61 (1H, m), 3.69–3.79 (2H, m), 6.82 (1H, d, J=1.2 Hz), 7.10–7.15 (6H, m), 7.31–7.34 (10H, m), 7.65 (1H, dd, J=1.7, 8.7 Hz), 7.84 (1H, d, J=8.7 Hz), 7.86 (1H, d, J=8.7 Hz), 8.00 (1H, dd, J=1.7, 8.7 Hz), 8.07 (1H, s), 8.43 (1H, s). IR (KBr): 3164, 2969, 1682, 1493, 1468, 1445, 1155, 1017, 820, 756, 748, 700 cm$^{-1}$.

(ii) Production of 1-{6-[1-Hydroxy-1-(1H-imidazol-4-yl)-2-methylpropyl]naphthalen-2-yl}-2-methyl-1-propanone In a similar manner to that described in Example 50-(iii), a reaction was carried out by using 1-{6-[1-hydroxy-2-methyl-1-(1-trityl-1H-imidazol-4-yl)-propyl]naphthalen-2-yl}-2-methyl-1-propanone (750 mg) to give the titled compound (429 mg) as a colorless powder.

$^1$H-NMR (CDCl$_3$) δ: 0.79 (3H, d, J=6.8 Hz), 1.01 (3H, d, J=6.8 Hz), 1.25 (6H, d, J=6.8 Hz), 2.65–2.78 (1H, m), 3.64–3.77 (1H, m), 7.00 (1H, d, J=1.0 Hz), 7.47 (1H, s), 7.68 (1H, dd, J=1.8, 8.8 Hz), 7.85 (1H, d, J=8.8 Hz), 7.87 (1H, d, J=8.8 Hz), 7.98 (1H, dd, J=1.8, 8.8 Hz), 8.10 (1H, s), 8.41 (1H, s); IR (KBr): 3069, 2971, 1676, 1628, 1474, 1385, 1221, 1155, 1128, 1017, 820 cm$^{-1}$.

EXAMPLE 60

Production of 1-(6-Ethylnaphthalen-2-yl)-1-(1H-imidazol-4-yl)-2-methyl-1-propanol (i) Production of 2-Methyl-1-(1-trityl-1H-imidazol-4-yl)-1-(6-vinylnaphthalen-2-yl)-1-propanol A solution of 1-(6-bromonaphthalen-2-yl)-2-methyl-1-(1-trityl-1H-imidazol-4-yl)-1-propanol (2.0 g), tetrakis(triphenylphosphine)palladium (116 mg) and tributylvinyltin (1.40 ml) in toluene (30 ml) was refluxed under argon atmosphere for 80 min. The solvent was distilled off and the residue was purified by column chromatography (eluent, hexane:THF=2:1),then crystallized from isopropyl ether-hexane (1:1) to give the titled compound (1.47 g) as a colorless powder.

$^1$H-NMR (CDCl$_3$) δ: 0.74 (3H, d, J=6.7 Hz), 0.95 (3H, d, J=6.7 Hz), 2.46–2.59 (1H, m), 3.71 (br s, 1H), 5.30 (1H, d, J=10.9 Hz), 5.84 (1H, d, J=17.7 Hz), 6.80 (1H, , s), 6.86 (1H, dd, J=10.9, 17.7 Hz), 7.10–7.16 (6H, m), 7.29–7.36 (10H, m), 7.52–7.62 (2H, m), 7.69–7.77 (3H, m), 7.98 (1H, s). IR (KBr): 3200, 2969, 1493, 1445, 1165, 1019, 820, 754, 747, 700 cm$^{-1}$.

(ii) Production of 1-(6-Ethylnaphthalen-2-yl)-2-methyl-1-(1-trityl-1H-imidazol-4-yl)-1-propanol 2-Methyl-1-(1-trityl-1H-imidazol-4-yl)-1-(6-vinylnaphthalen-2-yl)-1-propanol (1.20 g) was dissolved in THF (5 ml)-methanol (10 ml). To the solution was added 10% palladium carbon (120 mg), and the mixture was stirred at room temperature for 2 h under hydrogen atmosphere. The catalyst was filtered off and washed with THF. The filtrate was concentrated and the residue was recrystallized from isopropyl ether-hexane (1:1) to give the titled compound (1.13 g) as a colorless powder.

$^1$H-NMR (CDCl$_3$) δ: 0.74 (3H, d, J=6.8 Hz), 0.95 (3H, d, J=6.8 Hz), 1.31 (3H, t, J=7.6 Hz), 2.47–2.60 (1H, m), 2.79 (2H, q, J=7.6 Hz), 3.69 (1H, s), 6.80 (1H, s, J=1.4 Hz), 7.09–7.17 (6H, m), 7.27–7.36 (11H, m), 7.53 (1H, dd, J=1.8, 8.6 Hz), 7.58 (1H, s), 7.66–7.75 (2H, m), 7.98 (1H, s). IR (KBr): 3233, 2967, 1493, 1470, 1443, 1171, 1157, 1015, 905, 818, 756, 747 cm$^{-1}$.

(iii) Production of 1-(6-Ethylnaphthalen-2-yl)-1-(1H-imidazol-4-yl)-2-methyl-1-propanol In a similar manner to that described in Example 50-(iii), a reaction was carried out by using 1-(6-ethylnaphthalen-2-yl)-2-methyl-1-(1-trityl-1H-imidazol-4-yl)-1-propanol (950 mg) to give the titled compound (353 mg) as a colorless powder.

$^1$H-NMR (CDCl$_3$+CD$_3$OD) δ: 0.80 (3H, d, J=6.7 Hz), 1.00 (3H, d, J=6.7 Hz), 1.31 (3H, t, J=7.6 Hz), 2.65–2.85 (3H, m), 6.98 (1H, d, J=1.2 Hz), 7.33 (1H, dd, J=1.8, 8.6 Hz), 7.49 (1H, d, J=1.2 Hz), 7.54 (1H, dd, J=1.8, 8.6 Hz), 7.58 (1H, s), 7.58–7.77 (2H, m), 7.95 (1H, d, J=1.2 Hz). IR (KBr): 3231, 2971, 2776, 1458, 1433, 1346, 1238, 1113, 1030, 1019, 885, 874 cm$^{-1}$.

EXAMPLE 61

Production of 1-(1H-Imidazol-4-yl)-2-methyl-1-(6-methylnaphthalen-2-yl)-1-propanol (i) Production of 2-Methyl-1-(6-methylnaphthalen-2-yl)-1-(1-trityl-1H-imidazol-4-yl)-1-propanol 1-(6-Bromonaphthalen-2-yl)-2-methyl-1-(1-trityl-1H-imidazol-4-yl)-1-propanol (2.0 g), tetramethyltin (0.94 ml), dichlorobis(triphenylphosphine)palladium (70 mg) and lithium chloride (432 mg) were dissolved in DMF (20 ml). The solution was stirred at 80° C. for 17 h. After cooling, the solution was diluted with water and extracted with ethyl acetate. The extract was washed with water and saturated sodium chloride solution, successively, and dried. The solvent was distilled off, and the obtained residue was purified by silica gel chromatography (eluent, hexane:THF=6:1→4:1), and crystallized from isopropyl ether to give the titled compound (1.52 g) as colorless needles.

$^1$H-NMR (CDCl$_3$) δ: 0.74 (3H, d, J=6.8 Hz), 0.95 (3H, d, J=6.8 Hz), 2.46–2.59 (m, 1H), 2.48 (3H, s), 3.70 (1H, br s), 6.80 (1H, d, J=1.2 Hz), 7.08–7.17 (6H, m), 7.29–7.36 (11H, m), 7.52 (1H, dd, J=1.8, 8.8 Hz), 7.54 (1H, s), 7.63–7.72 (2H, m), 7.96 (1H, s). IR (KBr): 3258, 2965, 1495, 1445, 1177, 1013, 816, 754, 747, 700 cm$^{-1}$.

(ii) Production of 1-(1H-Imidazol-4-yl)-2-methyl-1-(6-methylnaphthalen-2-yl)-1-propanol In a similar manner to that described in Example 50-(ii), a reaction was carried out by using 2-methyl-1-(6-methylnaphthalen-2-yl)-1-(1-trityl-1H-imidazol-4-yl)-1-propanol (1.30 g) to give the titled compound (594 mg) as a colorless powder.

$^1$H-NMR (CDCl$_3$+CD$_3$OD) δ: 0.80 (3H, d, J=6.8 Hz), 1.00 (3H, d, J=6.8 Hz), 2.48 (3H, s), 2.64–2.77 (1H, m), 6.98 (1H, s), 7.28 (1H, dd, J=1.8, 8.3 Hz), 7.48–7.56 (2H, m), 7.65–7.74 (2H, m), 7.94 (1H, d, J=1.4 Hz). IR (KBr): 3171, 2980, 1433, 1127, 1119, 1028, 945, 885, 818 cm$^{-1}$.

EXAMPLE 62

Production of 1-(6-Ethynylnaphthalen-2-yl)-1-(1H-imidazol-4-yl)-2-methyl-1-propanol (i) Production of 1-(6-Ethynylnaphthalen-2-yl)-2-methyl-1-(1-trityl-1H-imidazol-4-yl)-1-propanol 1-(6-Bromonaphthalen-2-yl)-2-methyl-1-(1-trityl-1H-imidazol-4-yl)-1-propanol (3.0 g), trimethylsilylacetylene (1.44 ml), dichlorobis(triphenylphosphine)palladium (182 mg) and copper iodide (99 mg) were dissolved in triethylamine-THF (1:1, 50 ml). The solution was stirred at 60° C. for 24 h. To the solution were added trimethylsilylacetylene (0.72 ml), dichlorobis(triphenylphosphine)palladium (91 mg), and copper iodide (45 mg), and the mixture was stirred at 60° C. for 24 h. The solvent was distilled off, and the residue was purified by silica gel chromatography (eluent. hexane:THF=2:1) to give a brown oily compound.

The product was dissolved in 1N-sodium hydroxide-methanol-THF (1:1:2, 80 ml). The solution was stirred at room temperature for 90 min and concentrated under reduced pressure. The residue was extracted with ethyl acetate washed with saturated sodium chloride solution and dried. The solvent was distilled off, and the residue was purified by silica gel chromatography (eluent, hexane:THF=6:1→4:1) and crystallized from isopropyl ether to give the titled compound (2.31 g) as a pale yellow powder.

$^1$H-NMR (CDCl$_3$) δ: 0.73 (3H, d, J=6.7 Hz), 0.96 (3H, d, J=6.7 Hz), 2.46–2.59 (1H, m), 3.12 (1H, s), 3.74 (1H, br s), 6.80 (1H, d, J=1.4 Hz), 7.09–7.7.16 (6H, m), 7.29–7.34 (10H, m), 7.48 (1H, dd, J=1.6, 8.4 Hz), 7.57 (1H, dd, J=1.5, 8.7 Hz), 7.67–7.75 (2H, m), 7.96 (1H, s), 8.01 (1H, s). IR (KBr): 3314, 2971, 1493, 1470, 1447, 1169, 1009, 748, 700 cm$^{-1}$.

(ii) Production of 1-(6-Ethynylnaphthalen-2-yl)-1-(1H-imidazol-4-yl)-2-methyl-1-propanol In a similar manner to that described in Example 50-(ii), a reaction was carried out by using 1-(6-ethynylnaphthalen-2-yl)-2-methyl-1-(1-trityl-1H-imidazol-4-yl)-1-propanol (1.30 g) to give the titled compound (583 mg) as a colorless powder.

$^1$H-NMR (CDCl$_3$+CD$_3$OD) δ: 0.80 (3H, d, J=6.8 Hz), 1.01 (3H, d, J=6.8 Hz), 2.67–2.81 (1H, m), 3.20 (1H, s), 7.01 (1H, d, J=1.2 Hz), 7.49 (1H, dd, J=1.6, 8.4 Hz), 7.52 (1H, d, J=1.2 Hz), 7.62 (1H, dd, J=1.8, 8.6 Hz), 7.70–7.80 (2H, m), 7.97 (1H, s), 8.01 (1H, s). IR (KBr): 3316, 3316, 2980, 1460, 1435, 1119, 1030, 903, 816 cm$^{-1}$.

EXAMPLE 63

Production of 1-(1H-Imidazol-4-yl)-2-methyl-1-[(6-methylsulfanyl)naphthalen-2-yl)]-1-propanol (i) Production of O-(6-Bromonaphthalen-2-yl) dimethylcarbamothioate 6-Bromo-2-naphthol (44.63 g) was added to a solution of potassium hydroxide (12.29 g) in water (250 ml) and the mixture was cooled to 0° C. To the mixture was added dropwise a solution of N,N-dimethylthiocarbamoylchloride (25.30 g) in THF (200 ml), and the mixture was stirred at room temperature for 30 min. The reaction mixture was extracted with ethyl acetate. The organic layer was washed with water and saturated sodium chloride solution dried and concentrated. The obtained residue was washed with isopropyl ether to give the titled compound (43.30 g) as a brown solid.

$^1$H-NMR (CDCl$_3$) δ: 3.39 (3H, s), 3.48 (3H, s), 7.27 (1H, dd, J=2.2, 9.2 Hz), 7.47 (1H, d, J=2.2 Hz), 7.54 (1H, dd, J=2.0, 8.8 Hz), 7.67 (1H, d, J=8.8 Hz), 7.76 (1H, d, J=9.2 Hz), 8.01 (1H, d, J=2.0 Hz). IR (KBr): 1541, 1501, 1395, 1289, 1200, 1154, 897 cm$^{-1}$.

(ii) Production of S-(6-Bromonaphthalen-2-yl) dimethylcarbamothioate

O-(6-Bromonaphthalen-2-yl)dimethylcarbamothioate (42.12 g) was dissolved in diphenylether (300 ml). The solution was stirred at 250–260° C. for 3 h and cooled to room temperature, and diphenylether was distilled off in vacuo. To the obtained residue was added isopropyl ether to give the titled compound (37.10 g) as a brown solid.

$^1$H-NMR (CDCl$_3$) δ: 2.90–3.25 (6H, m), 7.51–7.61 (2H, m), 7.68 (1H, d, J=8.8 Hz), 7.75 (1H, d, J=8.6 Hz), 7.94–8.04 (2H, m). IR (KBr): 1667, 1362, 1098, 866, 689 cm$^{-1}$.

(iii) Production of 2-Bromo-6-(methylsulfanyl)naphthalene

S-(6-Bromonaphthalen-2-yl)dimethylcarbamothioate (13.80 g) was dissolved in ethanol (90 ml) and water (10 ml). To the solution was added potassium hydroxide (3.99 g), and the mixture was heated for 16 h under reflux. The mixture was cooled to 0° C., and to the mixture was added methyl iodide (3.6 ml), and the mixture was stirred for 1 h at −78° C. To the reaction mixture was added water, and the resulting precipitate was filtered off. The filtrate was dissolved in ethyl acetate. The organic layer was washed with water and saturated solution of sodium chloride, dried and concentrated. The obtained residue was purified by short column chromatography (eluent, hexane-ethyl acetate=10:1) to give the titled compound (10.89 g) as a colorless solid.

$^1$H-NMR (CDCl$_3$) δ: 2.58 (3H, s), 7.38 (1H, dd, J=1.8, 8.8 Hz), 7.48–7.68 (4H, m), 7.93 (1H, s). IR (KBr): 1572, 1140, 868, 812 cm$^{-1}$.

(iv) Production of 1-(1H-Imidazol-4-yl)-2-methyl-1-(6-methylsulfanylnaphthalen-2-yl)-1-propanol In a similar manner to that described in Example 39-(iii), a reaction was carried out by using 2-bromo-6-(methylsulfanyl)naphthalene (0.987 g) to give the titled compound (0.166 g) as a colorless solid.

$^1$H-NMR (CDCl$_3$+CD$_3$OD) δ: 0.79 (3H, d, J=6.8 Hz), 1.00 (3H, d, J=6.8 Hz), 2.57 (3H, s), 2.52–2.82 (1H, m), 6.99 (1H, s), 7.35 (1H, d, J=8.4 Hz), 7.42–7.80 (5H, m), 7.94 (1H, s). IR (KBr): 2971, 1491, 1140, 1013, 843 cm$^{-1}$.

EXAMPLE 64

Production of 1-(1H-Imidazol-4-yl)-1-(6-methoxy-1-methyl-naphthalen-2-yl)-2-methyl-1-propanol (i) Production of 6-Methoxy-1-methyl-1,2,3,4-tetrahydronaphthalen-1-ol In a similar manner to that described in Example 2-(i), a reaction was carried out by using 6-methoxytetralone (25.40 g) to give the titled compound (27.10 g) as an oil.

$^1$H-NMR (CDCl$_3$) δ: 1.54 (3H, m), 1.68–2.00 (4H, m), 2.66–2.81 (2H, m), 3.77 (3H, s), 6.58 (1H, d, J=2.9 Hz), 6.77 (1H, dd, J=2.9, 9.0 Hz), 7.49 (1H, d, J=9.0 Hz). IR (KBr): 3349, 2938, 1609, 1501, 1256 cm$^{-1}$.

(ii) Production of 7-Methoxy-4-methyl-1,2-dihydronaphthalene-1-ol

6-Methoxy-1-methyl-1,2,3,4-tetrahydronaphthalen-1-ol (26.90 g) and p-toluenesulfonic acid monohydrate (0.51 g) was dissolved in toluene (200 ml). The solution was heated for 30 min under reflux. The toluene was distilled off under reduced pressure. The obtained residue was purified by silica gel chromatography (eluent, hexane:ethyl acetate=10:1) to give the titled compound (22.40 g) as an oil.

$^1$H-NMR (CDCl$_3$) δ: 1.97–2.05 (3H, m), 2.12–2.30 (2H, m), 2.73 (2H, t, J=8.0 Hz), 3.79 (3H, s), 5.64–5.78 (1H, m), 6.64–6.76 (2H, m), 7.08–7.20 (1H, m). IR (KBr): 2934, 2832, 1497, 1252, 1142, 1034, 824 cm$^{-1}$.

(iii) Production of 3-Bromo-7-methoxy-4-methyl-1,2-dihydronaphthalene

7-Methoxy-4-methyl-1,2-dihydronaphthalene (3.01 9) was dissolved in dichloromethane (100 ml). To the solution was added dropwise a solution of bromine (3.00 g) in dichloromethane (10 ml) over a period of 15 min. To the mixture was added p-dimethylamino pyridine (1.83 g), and the mixture was heated for 8 h under reflux, and dichloromethane was distilled off under reduced pressure. The obtained residue was purified by silica gel chromatography (eluent, dichloromethane) to give the titled compound (2.34 g) as an oil.

$^1$H-NMR (CDCl$_3$) δ: 2.15–2.25 (3H, m), 2.65–2.95 (4H, m), 3.80 (3H, m), 6.67 (1H, d, J=2.7 Hz), 6.72 (1H, dd, J=2.7, 8.4 Hz), 7.19 (1H, d, J=8.4 Hz). IR (KBr): 2940, 1495, 1250 cm$^{-1}$.

(iv) Production of 2-Bromo-6-methoxy-1-methylnaphthalene

3-Bromo-7-methoxy-4-methyl-1,2-dihydronaphthalene (2.19 g) and 2,3-dichloro-5,6-dicyano-1,4-benzoquinone (DDQ, 2.10 g) were dissolved in toluene (200 ml), and the solution was stirred at 60° C. for 12 h. The toluene was distilled off under reduced pressure. The obtained residue was purified by silica gel chromatography (eluent, hexane) to give the titled compound (360 mg) as an oil.

$^1$H-NMR (CDCl$_3$) δ: 2.76 (3H, s), 3.92 (3H, s), 7.10 (1H, d, J=3.0 Hz), 7.18 (1H, dd, J=3.0, 9.2 Hz), 7.44 (1H, d, J=8.9 Hz), 7.56 (1H, d, J=9.2 Hz), 7.94 (1H, d, J=8.9 Hz). IR (KBr): 1624, 1588, 1505, 1410, 1242, 851 cm$^{-1}$.

(v) Production of 1-(1H-Imidazol-4-yl)-1-(6-methoxy-1-methyl-naphthalen-2-yl)-2-methyl-1-propanol In a similar manner to that described in Example 39-(iii), a reaction was carried out by using 2-bromo-6-methoxy-1-methylnaphthalene (340 mg) to give the titled compound (8 mg) as an amorphous product.

$^1$H-NMR (CDCl$_3$) δ: 0.89 (3H, d, J=6.6 Hz), 1.11 (3H, d, J=6.6 Hz), 2.57 (3H, s), 2.80–3.02 (1H, m), 3.92 (3H, s), 6.92 (1H, s), 7.07–7.17 (2H, m), 7.52 (1H, s), 7.58 (1H, d, J=9.2 Hz), 7.81 (1H, d, J=9.2 Hz), 7.96 (1H, d, J=9.2 Hz). IR (KBr): 2967, 1624, 1273, 1242, 912, 743 cm$^{-1}$.

EXAMPLE 65

Production of 1-(6-Methoxynaphthalen-2-yl)-2-methyl-1-(thiazol-5-yl)-1-propanol (i) Production of (6-Methoxynaphthalen-2-yl)(thiazol-5-yl)methanol To a solution of 6-methoxynaphthalen-2-ylmagnesium bromide in THF (1.3 M; 10 ml) was added dropwise a solution of 5-formylthiazole (1.70 g) in THF (10 ml) under ice cooling, and the mixture was stirred for 20 min under ice cooling. The mixture was diluted with saturated aqueous solution of ammonium chloride, extracted with ethyl acetate, washed with saturated sodium chloride solution and dried. The solvent was distilled off and the residue was purified by silica gel chromatography (eluent, hexane:ethyl acetate= 2:1→1:1) to give the titled compound (3.47 g) as a colorless powder.

$^1$H-NMR (CDCl$_3$) δ: 3.82 (1H, br s), 3.91 (3H, s), 6.17 (1H, s), 7.11–7.19 (2H, m), 7.42 (1H, dd, J=1.8, 8.6 Hz), 7.60 (1H, s), 7.68–7.78 (3H, m), 8.63 (1H, s). IR (KBr): 3310, 3077, 1609, 1393, 1269, 1026, 858 cm$^{-1}$.

(ii) (6-Methoxynaphthalen-2-yl)(thiazol-5-yl)ketone (6-methoxynaphthalen-2-yl)(thiazol-5-yl)methanol (2.0 g) was dissolved in dichloromethane (30 ml). To the solution was added manganese dioxide (6.0 g), and the mixture was stirred at room temperature for 3 h. The mixture was filtered with celite and the cake was rinsed with dichloromethane. The filtrate was concentrated and the obtained residue was recrystallized from ethyl acetate to give the titled compound (1.71 g) as a pale yellow powder.

$^1$H-NMR (CDCl$_3$) δ: 3.98 (3H, s), 7.21–7.28 (2H, m), 7.87 (1H, dd, J=3.2, 8.6 Hz), 7.97 (1H, dd, J=1.7, 8.7 Hz), 8.38 (1H, s), 8.46 (1H, s), 9.09 (1H, s). IR (KBr): 1624, 1481, 1306, 1265, 1217, 862, 816 cm$^{-1}$.

(iii) Production of 1-(6-Methoxynaphthalen-2-yl)-1-(thiazol-5-yl)-1-propanol

In a similar manner to that described in Example 1-(iv), a reaction was carried out by using (6-methoxynaphthalen-2-yl)(thiazol-5-yl)ketone (800 mg) to give the titled compound (447 mg) as a yellow substance.

$^1$H-NMR (CDCl$_3$) δ: 0.86 (3H, d, J=6.8 Hz), 1.05 (3H, d, J=6.8 Hz), 2.70–2.87 (2H, m), 3.91 (3H, s), 7.10–7.17 (2H, m), 7.50 (1H, dd, J=1.9, 8.7 Hz), 7.69 (1H, d, J=8.6 Hz), 7.73 (1H, d, J=8.8 Hz), 7.83 (1H, s), 7.93 (1H, d, J=1.8 Hz), 8.66 (1H, s). IR (KBr): 3187, 2971, 1402, 1269, 1144, 1026, 887, 843, 799 cm$^{-1}$.

EXAMPLE 66

Production of 1-(1H-Imidazol-4-yl)-2-methyl-1-(6-propylnaphthalen-2-yl)-1-propanol (i) Production of 1-(6-Allylnaphthalen-2-yl)-2-methyl-1-(1-trityl-1H-imidazol-4-yl)-1-propanol 1-(6-Bromonaphthalen-2-yl)-2-methyl-1-(1-trityl-1H-imidazol-4-yl)-1-propanol (2.0 g), allyltributyltin (1.26 ml), tris(dibenzylideneacetone)dipalladium (92 mg), tri(2-furyl)

phosphine (79 mg) and lithium chloride (432 mg) were dissolved in DMF (20 ml). The solution was stirred at 80° C. for 9 h. The solution was cooled, and diluted with water. The mixture was extracted with ethyl acetate, washed with water and saturated sodium chloride solution, successively, and dried. The solvent was distilled off and the residue was purified by silica gel chromatography (eluent, hexane:THF= 6:1) followed by crystallization from isopropyl ether-hexane to give the titled compound (1.57 g) as colorless needles.

$^1$H-NMR (CDCl$_3$) δ: 0.74 (3H, d, J=6.7 Hz), 0.95 (3H, d, J=6.7 Hz), 2.46–2.60 (1H, m), 3.53 (2H, d, J=6.6 Hz), 3.71 (1H, s), 5.07–5.18 (2H, m), 6.04 (1H, ddt, J=3.3, 10.1, 16.9 Hz), 6.80 (1H, d, J=1.4 Hz), 7.10–7.18 (6H, m), 7.27–7.36 (11H, m), 7.54 (1H, dd, J=1.8, 8.6 Hz), 7.57 (1H, s), 7.66–7.78 (2H, m), 7.99 (1H, d, J=1.4 Hz). IR (KBr): 3214, 2969, 1493, 1445, 1015, 907, 816, 748, 700 cm$^{-1}$.

(ii) Production of 2-Methyl-1-(6-propylnaphthalen-2-yl)-1-(1-trityl-1H-imidazol-4-yl)-1-propanol 1-(6-Allylnaphthalen-2-yl)-2-methyl-1-(1-trityl-1H-imidazol-4-yl)-1-propanol (1.40 g) was dissolved in THF-methanol (1:2) (15 ml). To the solution was added 10% palladium carbon (140 mg), and the mixture was stirred at room temperature for 2 h under hydrogen atmosphere. The catalyst was filtered and washed with THF. The filtrate was concentrated. The residue was chromatographed on silica gel (eluent, hexane:THF=1:1) and crystallized from isopropyl ether-hexane to give the titled compound (1.28 g) as a colorless powder.

$^1$H-NMR (CDCl$_3$) δ: 0.74 (3H, d, J=6.8 Hz), 0.93–1.00 (6H, m), 1.66–1.81 (2H, m), 2.47–2.60 (1H, m), 2.6,9–2.76 (2H, m), 3.75 (1H, s), 7.80 (1H, d, J=1.4 Hz), 7.10–7.18 (6H, m), 7.27–7.36 (1H, m), 7.53 (1H, dd, J=1.8, 8.6 Hz), 7.55 (1H, s), 7.66–7.74 (2H, m), 7.98 (1H, s). IR (KBr): 3486, 2963, 1493, 1443, 1159, 1007, 818, 756, 747, 702 cm$^{-1}$.

(iii) Production of 1-(1H-Imidazol-4-yl)-2-methyl-1-(6-propylnaphthalen-2-yl)-1-propanol In a similar manner to that described in Example 50-(ii), a reaction was carried out by using 2-methyl-1-(6-propylnaphthalen-2-yl)-1-(1-trityl-1H-imidazol-4-yl)-1-propanol (1.10 g) to give the titled compound (506 mg) as a colorless powder.

$^1$H-NMR (CDCl$_3$+CD$_3$OD) δ: 0.81 (3H, d, J=6.7 Hz), 0.97 (3H, t, J=7.3 Hz), 1.01 (3H, d, J=6.7 Hz), 1.63–1.81 (2H, m), 2.66–2.80 (3H, m), 6.99 (1H, d, J=1.0 Hz), 7.31 (1H, dd, J=1.7, 8.3 Hz), 7.50–7.57 (2H, m), 7.68–7.77 (2H, m), 7.95 (1H, m). IR (KBr): 3169, 2965, 1464, 1435, 1121, 1028, 951, 901, 816 cm$^{-1}$.

EXAMPLE 67

Production of 1-(1H-Imidazol-4-yl)-1-(6-isopropylnaphthalen-2-yl)-2-methyl-1-propanol (i) Production of 1-(6-Isopropenylnaphthalen-2-yl)-2-methyl-1-(1-trityl-1H-imidazol-4-yl)-1-propanol To a solution of methyltriphenylphosphonium bromide (3.24 g) in THF (80 ml) was added potassium t-butoxide (1.02 g) under ice cooling, and the mixture was stirred for 5 min. To the mixture was added a solution of 1-[6-[1-hydroxy-2-methyl-1-(1-trityl-1H-imidazol-4-yl)propyl]naphthalen-2-yl]-1-ethanone (2.0 g) in THF (40 ml), and the mixture was stirred at room temperature. After 30 min, to the mixture was added a mixed solution of methyltriphenylphosphonium bromide (1.30 g) and potassium t-butoxide (407 mg) in THF (15 ml), and the mixture was stirred at room temperature for 30 min. The mixture was diluted with water, extracted with ethyl acetate, washed with saturated sodium chloride solution and dried. The solvent was distilled off, and the residue was purified by silica gel chromatography (eluent, hexane:THF=6:1) to give the titled compound (1.91 g) as a colorless powder.

$^1$H-NMR (CDCl$_3$) δ: 0.74 (3H, d, J=6.8 Hz), 0.94 (3H, d, J=6.8 Hz), 2.25 (3H, s), 2.47–2.2.60 (1H, m), 3.71 (1H, br s), 5.16 (1H, m), 5.50 (1H, s), 6.80 (1H, d, J=1.4 Hz), 7.08–7.7.18 (6H, m), 7.29–7.37 (10H, m), 7.55 (1H, dd, J=1.8, 8.6 Hz), 7.63 (1H, d, J=1.8, 8.6 Hz), 7.71–7.80 (3H, m), 7.98 (1H, s). IR (KBr): 3193, 1493, 1445, 1144, 1017, 891, 748, 702 cm$^{-1}$.

(ii) Production of 1-(6-Isopropylnaphthalen-2-yl)-2-methyl-1-(1-trityl-1H-imidazol-4-yl)-1-propanol 1-(6-Isopropenylnaphthalen-2-yl)-2-methyl-1-(1-trityl-1H-imidazol-4-yl)-1-propanol (1.70 g) was dissolved in THF-methanol (2:1) (12 ml). To the solution were added 10% palladium carbon (170 mg), and the mixture was stirred at room temperature for 2 h under hydrogen atmosphere. The catalyst was filtered and washed with THF. The filtrate was concentrated and the obtained residue was purified by silica gel chromatography (eluent, hexane:THF=1:1). Crystallization from isopropyl ether-hexane gave the titled compound (1.60 g) as a colorless powder.

$^1$H-NMR (CDCl$_3$) δ: 0.74 (3H, d, J=6.7 Hz)" 0.95 (3H, d, J=6.7 Hz), 1.33 (6H, d, J=6.8 Hz), 2.47–2.60 (1H, m), 2.98–3.12 (1H, m), 3.69 (1H, s), 6.80 (1H, d, J=1.4 Hz), 7.10–7.15 (6H, m), 7.30–7.38 (11H, m), 7.53 (1H, d, J=1.8, 8.6 Hz), 7.59 (1H, s), 7.68–7.77 (2H, m), 7.98 (1H, s). IR (KBr): 3210, 2965, 1491, 1445, 1167, 1015, 907, 820, 756, 747, 700 cm$^{-1}$.

(iii) Production of 1-(1H-Imidazol-4-yl)-2-methyl-1-[6-(2-propyl)naphthalen-2-yl]-1-propanol In a similar manner to that described in Example 50-(ii), a reaction was carried out by using 1-(6-isopropylnaphthalen-2-yl)-2-methyl-1-(1-trityl-1H-imidazol-4-yl)-1-propanol (1.40 g) to give the titled compound (665 mg) as a colorless powder.

$^1$H-NMR (CDCl$_3$) δ: 0.79 (3H, d, J=6.7 Hz), 1.00 (3H, d, J=6.7 Hz), 1.32 (6H, d, J=7.0 Hz), 2.62–2.75 (1H, m), 2.97–3.11 (1H, m), 4.75 (2H, br s), 6.93 (1H, d, J=1.0 Hz), 7.36 (1H, dd, J=1.7, 8.7 Hz), 7.42 (1H, d, J=1.0 Hz), 7.55 (1H, dd, J=1.8, 8.6 Hz), 7.59 (1H, s), 7.69–7.77 (2H, m), 7.99 (1H, s). IR (KBr): 3054, 2961, 1462, 1385, 1163, 1130, 1003, 887, 818 cm$^{-1}$.

Preparation 1

Capsules
(1) Compound obtained in Example 210 mg
(2) lactose 90 mg
(3) microcrystalline cellulose 70 mg
(4) magnesium stearate 10 mg
One Capsule 180 mg The above (1), (2) and (3) and 5 mg of (4) were mixed. The mixture was granulated. To the granules was added (4) remaining. The whole content was sealed in a capsule.

Preparation 2

Tablets
(1) Compound obtained in Example 110 mg
(2) lactose 35 mg
(3) corn starch 150 mg
(4) microcrystalline cellulose 30 mg
(5) magnesium stearate 5 mg
One Tablet 230 mg The above (1), (2), (3), 20 mg of (4) and 2.5 mg of (5) were mixed. The mixture was granulated. To the granules was added (4) remaining and (5) remaining, and the mixture was compressively molded to give a tablet.

Experiment 1
Assay of Inhibitory Activity on Rat Steroid $C_{17-20}$-Lyase In Vitro Inhibitory activity was determined according to the method described in The Prostate, vol.26, 140–150(1995) with some modifications.

Testes excised from 13-week old, male SD rats were homogenized, and testicular microsomes were prepared by a series of centrifugation. The microsome protein (7 μg/10 μl) was added to 10 μl of 100 mM phosphate buffer (pH 7.4) in which 10 nM (final concentration) [1,2-3H]-17-α-hydroxyprogesterone, NADPH, and test compounds were dissolved. The reaction mixture was incubated for 7 min at 37° C., terminated by addition of 40 μl of Ethyl acetate, and briefly centrifuged. The substrate and the products (testosterone and androstenedione) in the upper phase were separated by silica gel thin layer chromatography. Detection of the spots and measurement of the radioactivity were performed by a BAS 2000 Bioimage analyzer. The concentration of the test compounds necessary to reduce the concentration of the products by 50% (The concentration in the control group in which no test compound was added was taken as 100%) was calculated, and shown in Table 1.

TABLE 1

| Example | Test Compound | $IC_{50}$ (nM) |
|---|---|---|
| 1 | 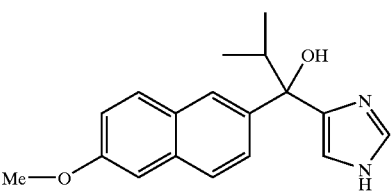 | 33 |
| 4 | 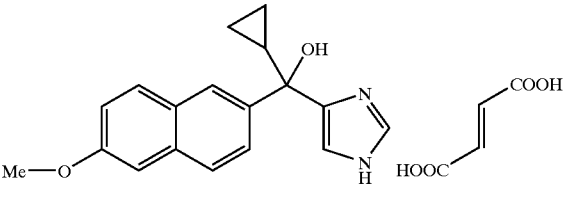 | 64 |
| 9 | 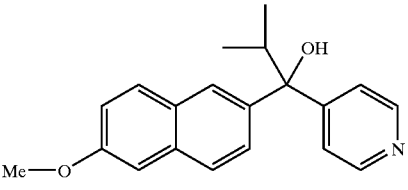 | 32 |
| 11 | 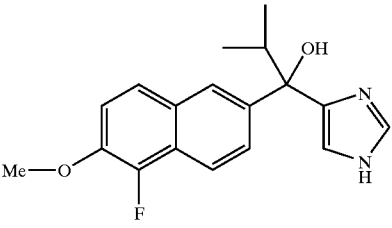 | 32 |
| 12 | 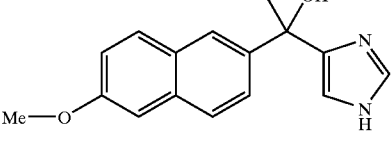 | 41 |
| 19 | 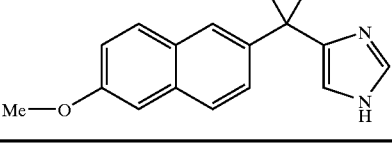 | 35 |

Experiment 2

Assay of Inhibitory Activity on Testosterone Biosynthesis in Rat

Test compounds were orally administered to 9-week old, male SD (Spague-Dawley) rats at a dose of 50 mg/kg. Two-h later blood was taken and testosterone concentration in serum was measured by radioimmunoassay. The percentage of the testosterone concentration of the groups of rats, which received test compounds, to that of the control group was calculated, and regarded as the inhibitory activity.

TABLE 2

| Test Compound | | Inhibitory activity on testosterone biosynthesis (T/C, %) |
|---|---|---|
| Example 1 | | 2.0 |
| Example 11 | | 9.0 |
| Example 12 | 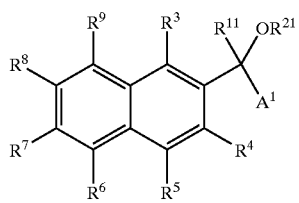 | 10 |

INDUSTRIAL APPLICABILITY

The compounds of the present invention and salts thereof have an inhibitory activity of steroid $C_{17,20}$-lyase and are useful for preventing and treating a mammal suffering from, for example, primary tumor, its metastasis and recurrence thereof, and various symptoms accompanied with these cancer, various diseases such as prostatic hypertrophy, virilism, hirsutism, male pattern alopecia, precocious puberty, endometriosis, uterus myoma, mastopathy, polycystic ovary syndrome, etc.

What is claimed is:

1. A compound of the formula:

(I')

wherein $A^1$ is an unsubstituted or substituted imidazolyl group;

$R^{11}$ is a hydrogen atom, a substituted or unsubstituted hydrocarbon group or a substituted or unsubstituted monocyclic aromatic heterocyclic group;

$R^{21}$ is a hydrogen atom or a substituted or unsubstituted lower alkyl group;

$R^3$, $R^4$, $R^5$, $R^6$, $R^7$, $R^8$ and $R^9$ are independently a hydrogen atom, a substituted or unsubstituted hydrocarbon group, a substituted or unsubstituted hydroxy group, a substituted or unsubstituted thiol group, an unsubstituted or substituted amino group, an acyl group or a halogen atom, provided that $R^{21}$ is a substituted or unsubstituted lower alkyl group when $R^{11}$ is a hydrogen atom, a salt thereof or a prodrug thereof.

2. A compound as claimed in claim 1, wherein $R^3$, $R^4$, $R^5$, $R^6$, $R^7$, $R^8$ and $R^9$ are independently a hydrogen atom, a substituted or unsubstituted hydrocarbon group, a substituted or unsubstituted hydroxy group, an unsubstituted or substituted amino group, an acyl group or a halogen atom.

3. A compound as claimed in claim 1, wherein $R^3$, $R^4$, $R^5$, $R^6$, $R^7$, $R^8$ and $R^9$ are independently a hydrogen atom, a substituted or unsubstituted hydrocarbon group, a substituted or unsubstituted hydroxy group or an acyl group.

4. A compound as claimed in claim 1, wherein $R^3$, $R^4$, $R^5$, $R^6$, $R^7$, $R^8$ and $R^9$ are independently a hydrogen atom, a substituted or unsubstituted hydrocarbon group, a substituted or unsubstituted hydroxy group, or a halogen atom.

5. A compound as claimed in claim 1, wherein $A^1$ is a substituted or unsubstituted 4- or 5-imidazolyl group.

6. A compound as claimed in claim 1, wherein $A^1$ is a substituted or unsubstituted 4- or 5-imidazolyl group optionally substituted with a $C_{1-4}$alkyl group unsubstituted or substituted with a $C_{1-4}$alkanoyl, carboxyl, or a $C_{1-4}$alkoxycarbonyl, a $C_{1-3}$alkoxy group, a $C_{1-6}$alkanoyl, $C_{1-4}$alkylsulfonyl, carbamoyl, a mono- or di-$C_{1-10}$alkyl carbamoyl group, a mono- or di-$C_{6-14}$aryl carbamoyl group, a mono- or di-$C_{7-16}$aralkylcarbamoyl group or sulfamoyl, a mono- or di-$C_{1-10}$alkyl sulfamoyl group, a mono- or di-$C_{6-14}$arylsulfamoyl group, or a mono- or di-$C_{7-16}$aralkyl sulfamoyl group.

7. A compound as claimed in claim 1, wherein $R^{21}$ is a hydrogen atom or a lower alkyl group.

8. A compound as claimed in claim 1, wherein $R^{21}$ is a hydrogen atom.

9. A compound as claimed in claim 1, wherein one to three groups of $R^3$, $R^4$, $R^5$, $R^6$, $R^7$, $R^8$ and $R^9$ are independently a substituted or unsubstituted hydrocarbon group, a substituted or unsubstituted hydroxy group, an unsubstituted or substituted amino group, an acyl group or a halogen atom.

10. A compound as claimed in claim 1, wherein one to three groups of $R^3$, $R^4$, $R^5$, $R^6$, $R^7$, $R^8$ and $R^9$ are independently a substituted or unsubstituted $C_{1-6}$alkyl group, a substituted or unsubstituted hydroxy group or a $C_{1-6}$acyl group.

11. A compound as claimed in claim 1, wherein $R^{11}$ is a hydrogen atom, a substituted or unsubstituted lower alkyl group, a substituted or unsubstituted phenyl group or a substituted or unsubstituted pyridyl group.

12. A compound as claimed in claim 1, wherein $R^{11}$ is a hydrogen atom, a lower alkenyl group, a cyclic alkyl group, a phenyl group, a pyridyl group, or a lower alkyl group unsubstituted or substituted with halogen atom(s).

13. A compound as claimed in claim 1, wherein $R^{11}$ is a $C_{1-6}$alkyl group and $R^{21}$ is a hydrogen atom.

14. A compound as claimed in claim 1, wherein $R^{11}$ is an isopropyl group and $R^{20}$ is a hydrogen atom.

15. A compound as claimed in claim 1, wherein $R^7$ is a substituted or unsubstituted hydroxy group or a lower alkyl group.

16. A compound as claimed in claim 1, wherein $R^7$ is (1) a substituted or unsubstituted hydroxy group optionally substituted with a lower alkanoyl group, a lower alkanoyloxy-lower alkyl group, a lower alkyl group, a lower alkoxy-lower alkyl group, a substituted or unsubstituted lower alkyl group optionally having one to 4 halogen atoms, or a benzyl group, (2) a halogen atom, (3) a substituted or unsubstituted lower alkyl group optionally substituted with a hydroxy group, (4) a lower alkynyl group, (5) a lower alkanoyl group, (6) an unsubstituted or substituted amino group optionally substituted with a lower alkanoyl group, a lower alkylaminocarbonyl group or a lower alkylsulfonyl group, or (7) a lower alkylthio group.

17. A compound as claimed in claim 1, wherein $R^7$ is a lower alkyl group, a lower alkoxy group or a lower alkanoylamino group.

18. A compound as claimed in claim 1, wherein $R^7$ is a methoxy group.

19. A compound as claimed in claim 1, wherein $R^8$ is a hydrogen atom, a lower alkyl group or a lower alkoxy group.

20. A compound as claimed in claim 1, wherein $R^8$ is a hydrogen atom or a lower alkoxy group.

21. A compound as claimed in claim 1, wherein $R^6$ is (1) a hydrogen atom, (2) a halogen atom, (3) a lower alkoxy group or (4) a substituted or unsubstituted lower alkyl group optionally substituted with a hydroxy group.

22. A compound as claimed in claim 1, wherein $R^6$ is a hydrogen atom or a lower alkyl group.

23. A compound as claimed in claim 1, wherein one of $R^6$, $R^7$ and $R^8$ is a lower alkyl group or a lower alkoxy group.

24. A compound as claimed in claim 1, wherein each of $R^3$, $R^4$, $R^5$ and $R^9$ is a hydrogen atom.

25. A prodrug of a compound as claimed in claim 1.

26. A compound selected from the group consisting of 1-(1H-imidazol-4-yl-1-(6-methoxynaphthalen-2-yl)-2-methyl-1-propanol, 1-(6,7-dimethoxynaphthalen-2-yl)-1-(1H-imidazol-4-yl)-2-methyl-1-propanol, 1-(6-methoxy-5-methylnaphthalen-2-yl)-1-(1H-imidazol-4-yl)-2-methyl-1-propanol, N-{6-[1-hydroxy-1H-imidazol-4-yl)-2-methylpropyl]naphthalen-2-yl}acetamide or 1-(6-ethylnaphthalen-2-yl)-1H-imidazol-4-yl)-2-methyl-1-propanol or a salt thereof.

27. A composition comprising a compound of the formula:

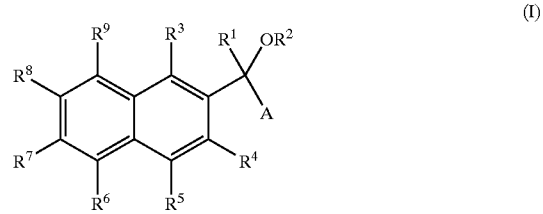

wherein

A is an unsubstituted or substituted imidazolyl group, $R^1$ is a hydrogen atom, unsubstituted or substituted hydrocarbon group or unsubstituted or substituted monocyclic aromatic heterocyclic group, $R^2$ is a hydrogen atom or a substituted or unsubstituted lower alkyl group, $R^3$, $R^4$, $R^5$, $R^6$, $R^7$, $R^8$ and $R^9$ are independently a hydrogen atom, a substituted or unsubstituted hydrocarbon group, a substituted or unsubstituted hydroxy group, a substituted or unsubstituted thiol group, an unsubstituted or substituted amino group, an acyl group or a halogen atom, provided that $R^2$ is a substituted or unsubstituted lower alkyl group when $R^1$ is a hydrogen atom, a salt thereof or a prodrug thereof, and a pharmaceutically acceptable carrier, diluent or excipient.

28. A method for treating a disease whose exacerbation factor is androgen or estrogen, which comprises administering an effective amount of a compound of the formula:

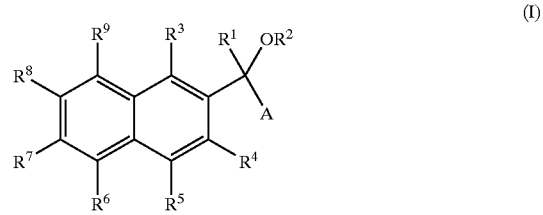

wherein

A is an unsubstituted or substituted imidazolyl group, $R^1$ is a hydrogen atom, unsubstituted or substituted hydrocarbon group or unsubstituted or substituted monocyclic aromatic heterocyclic group, $R^2$ is a hydrogen atom or a substituted or unsubstituted lower alkyl group, $R^3$, $R^4$, $R^5$, $R^6$, $R^7$, $R^8$ and $R^9$ are independently a hydrogen atom, a substituted or unsubstituted hydrocarbon group, a substituted or unsubstituted hydroxy group, a substituted or unsubstituted thiol group, an unsubstituted or substituted amino group, an acyl group or a halogen atom, a salt thereof or a prodrug thereof, optionally together with a pharmaceutically acceptable carrier, diluent or excipient, to a patient.

29. A method as claimed in claim 28 wherein the diseases whose exacerbation factor is androgen or estrogen is a cancer.

30. A method as claimed in claim 29 wherein the cancer is breast cancer or prostate cancer.

31. A method for making a steroid $C_{17-20}$ lyase inhibitory composition comprising mixing the composition with a compound of the formula:

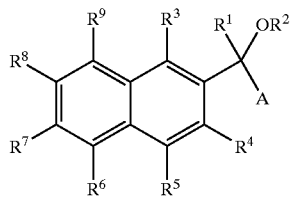

(I)

wherein A is an unsubstituted or substituted imidazolyl group, $R^1$ is a hydrogen atom, unsubstituted or substituted hydrocarbon group or substituted or unsubstituted monocyclic aromatic heterocyclic group, $R^2$ is a hydrogen atom or a substituted or unsubstituted lower alkyl group, $R^3$, $R^4$, $R^5$, $R^6$, $R^7$, $R^8$ and $R^9$ are independently a hydrogen atom, a substituted or unsubstituted hydrocarbon group, a substituted or unsubstitued hydroxy group, a substituted or unsubstituted thiol group, an unsubstituted or substituted amino group, an acyl group or a halogen atom, provided that $R^2$ is a substituted or unsubstituted lower alkyl group when $R^1$ is a hydrogen atom, a salt thereof or a prodrug thereof;

and a pharmaceutically acceptable carrier, diluent or excipient.

32. The method as claimed in claim 31, wherein the composition is for treating cancer.

33. The method as claimed in claim 31, wherein the composition is for treating breast cancer or prostate cancer.

34. A compound of the formula:

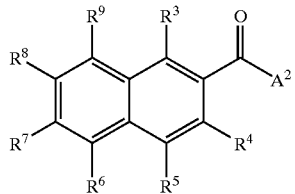

(II')

wherein $A^2$ is an unsubstituted or substituted 4-imidazolyl group, $R^3$, $R^4$, $R^5$, $R^6$, $R^7$, $R^8$ and $R^9$ are independently a hydrogen atom, a substituted or unsubstituted hydrocarbon group, a substituted or unsubstituted hydroxy group, a substituted or unsubstituted thiol group, an unsubstituted or substituted amino group, an acyl group or a halogen atom, wherein one to three groups selected from the group consisting of $R^3$, $R^4$, $R^5$, $R^6$, $R^7$, $R^8$ and $R^9$ are independently a substituted or unsubstituted lower alkyl group, a substituted or unsubstituted hydroxy group, an unsubstituted or substituted amino group, an acyl group or a halogen atom;

or a salt thereof.

35. A process for producing a compound of the formula:

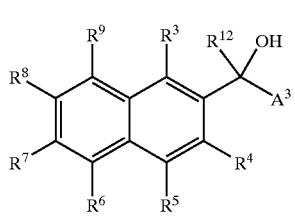

(Ib)

wherein $A^3$ is an unsubstituted or substituted imidazolyl group, $R^3$, $R^4$, $R^5$, $R^6$, $R^7$, $R^8$ and $R^9$ are independently a hydrogen atom, a substituted or unsubstituted hydrocarbon group, a substituted or unsubstituted hydroxy group, a substituted or unsubstituted thiol group, an unsubstituted or substituted amino group, an acyl group or a halogen atom, and $R^{12}$ is a substituted or unsubstituted hydrocarbon group or a substituted or unsubstituted monocyclic aromatic heterocyclic group or a salt thereof, which comprises reacting a compound of the formula:

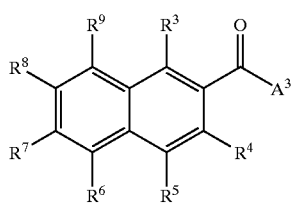

(II)

wherein each symbol has the same meaning as defined above or a salt thereof with a compound of the formula:

$$R^{12}-M \quad \text{(III)}$$

wherein M is a metal or a salt thereof and $R^{12}$ has the same meaning as defined above.

* * * * *